(12) United States Patent
Thomas et al.

(10) Patent No.: US 8,093,302 B2
(45) Date of Patent: Jan. 10, 2012

US008093302B2

(54) SUBSTITUTED TETRALINS AS SELECTIVE ESTROGEN RECEPTOR-β AGONISTS

(75) Inventors: Elizabeth Marie Thomas, Lexington, KY (US); Bryan Hurst Norman, Indianapolis, IN (US); Julian Stanley Kroin, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 254 days.

(21) Appl. No.: 11/814,806

(22) PCT Filed: Feb. 10, 2006

(86) PCT No.: PCT/US2006/004540
§ 371 (c)(1),
(2), (4) Date: Mar. 1, 2010

(87) PCT Pub. No.: WO2006/088716
PCT Pub. Date: Aug. 24, 2006

(65) Prior Publication Data
US 2010/0249075 A1    Sep. 30, 2010

(51) Int. Cl.
*A61K 31/045* (2006.01)
*A61K 31/135* (2006.01)
*A61K 31/05* (2006.01)
*A61K 31/075* (2006.01)
*C07C 211/00* (2006.01)
*C07C 43/02* (2006.01)
*C07C 43/20* (2006.01)
*C07C 35/42* (2006.01)
*C07C 39/12* (2006.01)

(52) U.S. Cl. ........ 514/729; 514/649; 514/719; 514/732; 564/338; 564/379; 568/633; 568/707; 568/714; 568/719

(58) Field of Classification Search .................. 514/729, 514/649, 732, 719; 564/379, 338; 568/633, 568/707, 714, 719
See application file for complete search history.

(56) References Cited

U.S. PATENT DOCUMENTS

| 6,436,923 | B1 | 8/2002 | Bhagwat et al. |
| 6,518,301 | B1 | 2/2003 | Barlaam et al. |
| 6,593,322 | B1 | 7/2003 | Bhagwat et al. |
| 6,630,508 | B1 | 10/2003 | Dodge et al. |
| 6,794,403 | B2 | 9/2004 | Malamas et al. |

FOREIGN PATENT DOCUMENTS

| WO | WO 03/044006 | 5/2003 |
| WO | WO 2004/094400 | 11/2004 |
| WO | WO 2004/094401 | 11/2004 |
| WO | WO 2006/044176 | 4/2006 |

OTHER PUBLICATIONS

Sun, et al., "Novel ligands that function as selective estrogens or antiestrogens for estrogen receptor-A or estrogen receptor-SS," Endocrinology, vol. 140, No. 2, pp. 800-804 (1999).
Yang, et al., "Enzyme-catalyzed asymmetric deacylation for the preparation of Lasofoxifene (CP-336156), a selective estrogen receptor modulator," Organic Letters, vol. 2, No. 25, pp. 4025-4027 (2000).
Meyers, et al., "Estrogen Receptor-b Potency-Selective Ligands: Structure-Activity Relationship Studies of Diarylpropionitriles and Their Acetylene and Polar Analogues," *J. Med. Chem.*, vol. 44, pp. 4230-4251 (2001).

*Primary Examiner* — Sreeni Padmanabhan
*Assistant Examiner* — Jody Karol
(74) *Attorney, Agent, or Firm* — John C. Demeter

(57) ABSTRACT

The present invention relates to novel tetralin ER-β agonist compounds, pharmaceutical compositions thereof, and use of these compounds to treat a ER-β mediated disease such as nocturia, obstructive uropathy, benign prostatic hypertrophy, obesity, dementia, hypertension, incontinence, colon cancer, prostate cancer, infertility, depression, leukemia, inflammatory bowel disease, and arthritis.

2 Claims, No Drawings

SEQUENCE LISTING

<160> NUMBER OF SEQ ID NOS: 3

<210> SEQ ID NO 1
<211> LENGTH: 19
<212> TYPE: DNA
<213> ORGANISM: Mus sp.

<400> SEQUENCE: 1
cgcagaccgg actccagat                                              19

-continued

```
<210> SEQ ID NO 2
<211> LENGTH: 19
<212> TYPE: DNA
<213> ORGANISM: Mus sp.

<400> SEQUENCE: 2
ccacgcacag caggagaat                                            19

<210> SEQ ID NO 3
<211> LENGTH: 21
<212> TYPE: DNA
<213> ORGANISM: Mus sp.

<400> SEQUENCE: 3
ccaaggaggc cacgccatga a                                         21
```

SUBSTITUTED TETRALINS AS SELECTIVE ESTROGEN RECEPTOR-β AGONISTS

BACKGROUND OF THE INVENTION

The present invention relates to novel tetralin ER-β agonist compounds, pharmaceutical compositions thereof, and use of these compounds to treat a ER-β mediated disease such as benign prostatic hypertrophy, obesity, dementia, hypertension, incontinence, colon cancer, prostate cancer, infertility, depression, leukemia, inflammatory bowel disease, and arthritis.

Estrogens play important roles in the development and homeostasis of the reproductive, central nervous, skeletal, and cardiovascular systems of both males and females. Recently, a new estogen receptor ("ER") isoform, ER-β is cloned from a rat prostatic cDNA library and is present in murine and human prostates. Consequently, the previously known ER is now designated as ER-α. ER-α and ER-β share high amino acid homology, have similar 17-β Estradiol (E2) binding affinities, and can hetero- or homodimerize to form a signaling complex. See, e.g., Kuiper G G, et at, Endocrinol. 138: 863-70 (1997); and Kuiper G G et al., Proc. Natl. Acad. Sci. USA 93: 5925-30 (1996). Although E2 activates both ER-α and ER-β, tissue distribution and functional differences between the two have been noted, making subtype selective ligands more attractive for various disease targets. Interestingly, 3-beta, 17-beta-androstanediol and 5-alpha-androstane have been proposed to be endogenous ligands for ER-β. See e.g., Weihua Z. et al. PNAS 98: 6330-5 (2001). 3-Beta, 17-beta-androstanediol is a major metabolite of dihydrotestosterone (DHT), the 5-alpha-reduced active intracellular androgen in male accessory sex organs. ER-β activation also stimulates increased glutathione S-transferase and quinone reductase expression. These two enzymes have been shown to possess chemoprotective detoxification properties; Chang W Y et al., Prostate 40: 115-24 (1999); Montano M M et al., J. Biol. Chem. 273: 25443-9 (1998).

With the recent identification of ER-β, and the recognition that ER-α and ER-β have different biological roles, ER-β selective modulators would similarly possess significant clinical utility. Since ER-β is strongly expressed in a number of tissues including prostate, bladder, ovary, testis, lung, small intestine, vascular endothelium, and various parts of the brain, compounds that selectively modulate ER-β have been suggested as being useful in the treatment of a variety of disease conditions, such as obesity, dementia, hypertension, incontinence, colon cancer, prostate cancer, infertility, depression, leukemia, inflammatory bowel disease, and arthritis. See e.g., J. Gustafsson, TIPS, 24 (9), p 479-485 (2003); and Endocrinology, 144, p. 4241-4249 (2003). Selective compounds should have minimal effect on tissues that contain ER-α, and thus exhibit different side-effect profiles. Thus, ER-β agonists will display different therapeutic profiles compared to ER-α antagonists or agonists, and would be preferentially beneficial in tissues relying on ER-β signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. Because these approaches are of limited therapeutic benefit, new therapies are needed.

BRIEF SUMMARY OF THE INVENTION

In a 1st embodiment, the present invention provides a compound of Formula I:

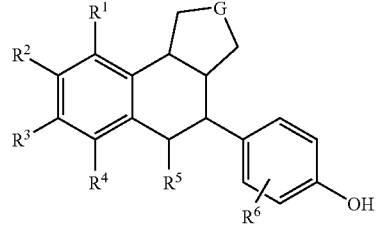

Formula I wherein:
G is —CH$_2$—, —CH$_2$CH$_2$—, —CH$_2$C(CH$_3$)$_2$— or —O—;
$R^1$ is hydrogen, hydroxy or amino;
$R^2$ is hydrogen or hydroxy;
$R^3$ is hydrogen, hydroxy, Br, methyl, n-propyl, i-propyl, n-butyl, hydroxymethyl, methoxy, CH$_3$CH(OH)—, acetyl, CH$_3$OCH$_2$—, $R^7$C(O)CH$_2$CH$_2$— or $R^8$CH$_2$CH$_2$CH$_2$—;
or $R^2$ and $R^3$ form a —CH$_2$CH$_2$—X—O— biradical, wherein the oxygen radical represents the $R^2$ end and the methylene radical represents the $R^3$ end;
X is —C(O)— or —C(=CH$_2$)—;
$R^4$ is hydrogen, hydroxy, cyano, $R^9$—CH$_2$—, vinyl, 4-chlorophenyl, carboxy, aminocarbonyl or methoxycarbonyl;
$R^5$ is hydrogen, methyl, ethyl, $R^{10}$—CH$_2$—, CH$_3$CH(OH)—, acetyl, carboxyl or methoxycarbonyl;
$R^6$ is hydrogen or fluoro;
$R^7$ is amino, methylamino, dimethylamino or piperidin-1-yl;
$R^8$ is bromo, hydroxy, dimethylamino or methoxy;
$R^9$ is bromo, cyano, hydroxy, methoxy or azido;
$R^{10}$ is bromo, hydroxy, cyano, methoxy or pyrrolidin-1-yl;
with the provisos that:
  at least one or $R^1$, $R^2$, $R^3$ and $R^4$ is hydroxy and
  at least three of $R^1$, $R^2$, $R^3$, $R^4$ and $R^5$ are hydrogen and enantiomers thereof.
In a specific embodiment, the compound is of Formula Ia:

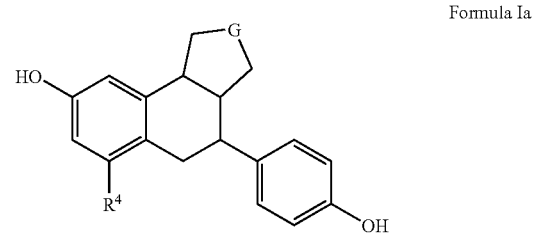

Formula Ia and enantiomers thereof.

In another specific embodiment, the compound is of formula Ia and G is —CH$_2$—.

In another specific embodiment, the compound is of formula Ia and G is —O—.

In another specific embodiment, the compound is of formula Ia and G is —CH$_2$—CH$_2$—:

In another specific embodiment, the compound is of formula Ia and G is —CH$_2$C(CH$_3$)$_2$—.

In another specific embodiment, the compound is of formula Ib:

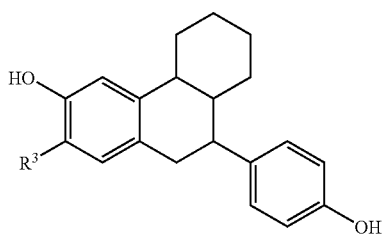

Formula Ib and enantiomers thereof.

In another specific embodiment, the compound is of formula Ib and R$^3$ is R$^7$C(O)CH$_2$CH$_2$—.

In another specific embodiment, the compound is of formula Ib and R$^3$ is R$^8$CH$_2$CH$_2$CH$_2$— or hydroxymethyl.

In another specific embodiment, the compound is of Formula Ic:

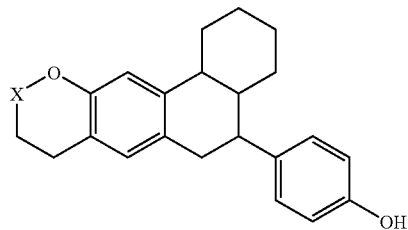

Formula Ic and enantiomers thereof.

In another specific embodiment, the compound is of Formula Id:

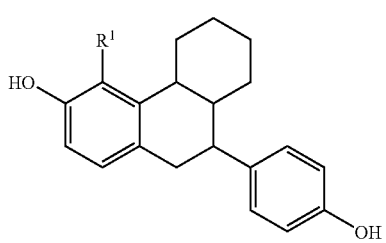

Formula Id and enantiomers thereof.

In another specific embodiment, the compound is of Formula Ie:

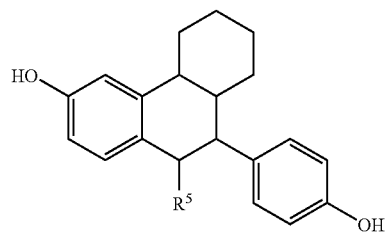

Formula Ie and enantiomers thereof.

In another specific embodiment, the compound is of Formula If:

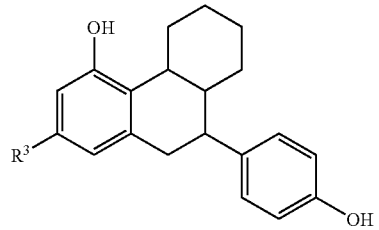

Formula If and enantiomers thereof.

In another specific embodiment, the compound is of formula Ig:

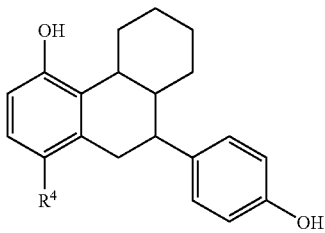

Formula Ig and enantiomers thereof.

In a 2$^{nd}$ embodiment, the present invention provides a pharmaceutical composition comprising: a compound of Formula I, or pharmaceutically acceptable salt thereof, together with a pharmaceutically acceptable carrier, diluent or excipient.

In a 3$^{rd}$ embodiment, the present invention provides a method of treating nocturia, obstructive uropathy, obesity, dementia, hypertension, incontinence, colon cancer, prostate cancer, infertility, depression, leukemia, inflammatory bowel disease, arthritis, or benign prostatic hypertrophy in a patient, comprising: administering to said patient an effective amount of a compound of Formula I, or pharmaceutically acceptable salt thereof.

In a specific embodiment, the condition being treated is benign prostatic hypertrophy.

In another specific embodiment, the condition being treated is prostate cancer.

In a 4$^{th}$ embodiment, the present invention provides a method of treating nocturia, uropathy, obesity, dementia, hypertension, incontinence, colon cancer, prostate cancer, infertility, depression, leukemia, inflammatory bowel disease, arthritis or benign prostatic hypertrophy in a patient, comprising: administering to said patient a pharmaceutical composition comprising a compound of Formula I, or pharmaceutically acceptable salt thereof, together with a pharmaceutically acceptable carrier, diluent or excipient.

In a specific embodiment, the condition being treated is benign prostatic hypertrophy.

In another specific embodiment, the condition being treated is prostate cancer.

In a 5th embodiment, the present invention provides the use of a compound, or pharmaceutically acceptable salt thereof, of Formula I for the manufacture of a medicament for the treatment of nocturia, uropathy, obesity, dementia, hypertension, incontinence, colon cancer, prostate cancer, infertility, depression, leukemia, inflammatory bowel disease, arthritis, or benign prostatic hypertrophy.

In a specific embodiment, the medicament is for the treatment of benign prostatic hypertrophy.

In another specific embodiment, the medicament is for the treatment of prostate cancer.

In a 6th embodiment, the present invention provides a method of agonizing ER-β receptor function, comprising: contacting the receptor with a compound of Formula I, or a pharmaceutically acceptable salt thereof.

In a 7th embodiment, the present invention provides a method of agonizing ER-β receptor function in a patient, comprising: administering to said patient an effective amount of a compound of Formula I, or a pharmaceutically acceptable salt thereof.

In an 8th embodiment, the present invention provides a method of treating ER-β mediated disease condition in a patient, comprising: administering to said patient an effective amount of a compound of Formula I, or a pharmaceutically acceptable salt thereof.

In a specific embodiment, the condition is nocturia, obstructive uropathy, obesity, dementia, hypertension, incontinence, colon cancer, prostate cancer, infertility, depression, leukemia, inflammatory bowel disease, arthritis, or benign prostatic hypertrophy.

In another specific embodiment, the condition is benign prostatic hypertrophy.

In another specific embodiment, the condition is prostate cancer.

DETAILED DESCRIPTION OF THE INVENTION

As used herein:

a) the term "$C_1$-$C_4$ alkyl" refers to a branched or straight chained alkyl radical containing from 1 to 4 carbon atoms, such as methyl (Me), ethyl (Et), n-propyl, isopropyl, n-butyl, isobutyl, sec butyl (s-Bu) or tert-butyl (t-Bu);

b) the term "$C_2$-$C_4$ alkenyl" refers to a straight or branched hydrocarbon chain of 2 to 4 carbon atoms with at least one carbon-carbon double bond. Examples of $C_2$-$C_4$ alkenyl groups include, but are not limited to, ethenyl(vinyl), propen-1-yl, propen-2-yl(isoprenyl), propen-3-yl(allyl), 2-methyl-propen-3-yl, 2-buten-4-yl, 2-methyl-propen-1-yl, and 1-buten-1-yl;

c) the term "$C_2$-$C_4$ alkynyl" refers to a straight or branched hydrocarbon chain of 2 to 4 carbon atoms with at least one carbon-carbon triple bond. Examples of $C_2$-$C_4$ alkynyl groups include, but are not limited to, ethynyl, propyn-1-yl, propyn-2-yl(isoprynyl), propyn-3-yl, 2-methyl-propyn-3-yl, 2-butyn-4-yl, 2-methyl-propyn-1-yl, and 1-butyn-1-yl;

d) the terms "halo" and "halide" refers to a fluorine atom, chlorine atom, bromine atom, or iodine atom;

e) the designation " ⁓ " 'refers to a bond for which the stereochemistry is not designated;

f) the designation " ▬ " refers to a bond that protrudes forward out of the plane of the page;

g) the designation " ''''' " refers to a bond that protrudes backward out of the plane of the page;

h) as used in the preparations and examples the following terms have the indicated meanings; "ng" refers to nanograms; "μg" refers to micrograms; "mg" refers to milligrams; "g" refers to grams; "kg" refers to kilograms; "nmole" refers to nanomoles; "mmol" refers to millimoles; "mol" refers to moles; "μL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^2_D{}^0$" refer to specific rotation of the D line of sodium at 20° C. obtained in a 1 decimeter cell; "c" refers to concentration in g/mL; "nM" refers to nanomolar; "μM" refers to micromolar; "mM" refers to millimolar; "M" refers to molar; "$K_i$" refers to inhibiton constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "MS" refers to mass spectrum; "tetrahydrofuran" refers to tetrahydrofuran; "brine" refers to a saturated aqueous solution of sodium chloride; "L.O.D." refers to loss on drying; "μCi" refers to microcuries; "i.p." refers to intraperitoneally; "i.v." refers to intravenously; "DPM" refers to disintegrations per minute; DMSO refers to dimethylsulfoxide; ethyl acetate refers to ethyl acetate; "TLC" refers to thin layer chromatography, DMF refers to dimethylformamide; "DMSO" refers to dimethylsulfoxide; the term "enantiomeric excess" or "ee" refers to the percent by which one enantiomer, E1, is in excess in a mixture of the two enantiomers, E1 plus E2, such that {(E1−E2)÷(E1+E2)}×100=ee;

j) the term "patient" refers to a warm blooded animal such as a mammal that is afflicted with a particular estrogen receptor-beta mediated disease. It is understood that guinea pigs, dogs, cats, rats, mice, horses, cattle, sheep, and humans are examples of animals within the scope of the meaning of the term;

k) the terms "effective amount" and "therapeutically effective amount" of a compound of Formula (I) refer to an amount which is effective in controlling diseases and conditions associated with estrogen receptor-beta mediated diseases such as obesity, dementia, hypertension, incontinence, colon cancer, prostate cancer, infertility, depression, leukemia, inflammatory bowel disease, arthritis or benign prostatic hypertrophy;

l) the term "controlling diseases" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as obesity, dementia, hypertension, incontinence, colon cancer, prostate cancer, infertility, depression, leukemia, inflammatory bowel disease, arthritis or benign prostatic hypertrophy;

m) the term "pharmaceutically acceptable salts thereof" refers to either an acid addition salt or a basic addition salt;

n) the term "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

o) the term "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Compounds of Formula I may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention.

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991).

Reaction Schemes

Compounds of Formula I, and intermediates thereof, can be prepared as described in Reaction Schemes 1-4 below. All substituents, unless otherwise indicated, are as previously defined. The reagents and starting materials are readily available to one of ordinary skill in the art.

The skilled artisan will appreciate that the present invention contemplates all enantiomers and mixtures of enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral phase gas chromatography, chiral-phase high performance liquid chromatography, or crystallizing the compound as a chiral salt complex, and resolutions may be performed at any stage or at the end of any step that is advantageous in the schemes below. Enantiomers and stereoisomers can also be obtained from stereomerically- or enantiomerically-pure intermediates, reagents, and catalysts by well known asymmetric synthetic methods.

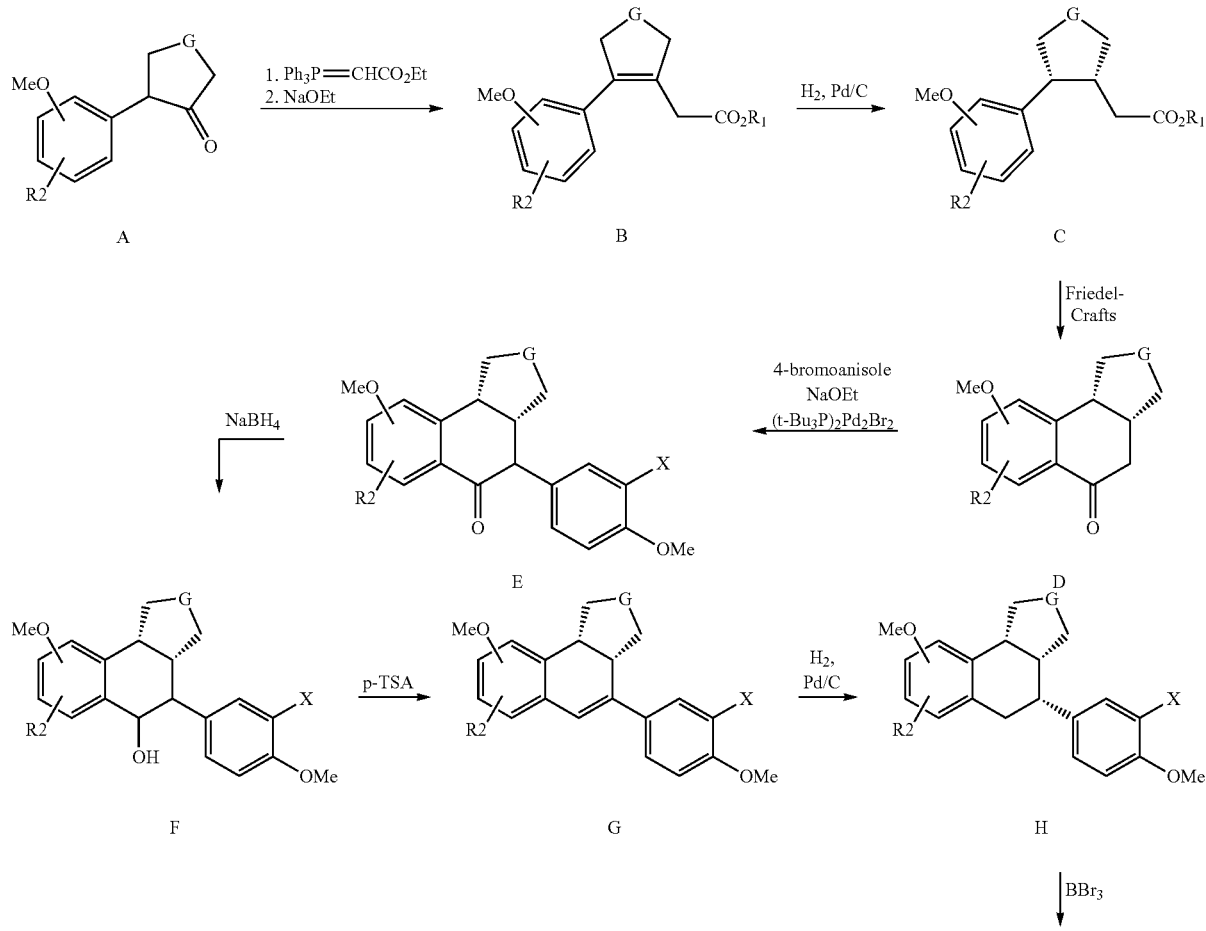

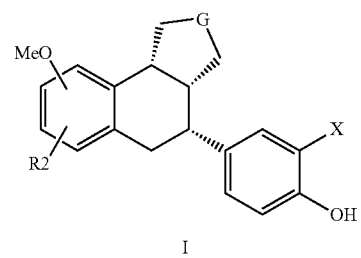

In Scheme 1, starting materials A (G=CH$_2$, CH$_2$CH$_2$, CH$_2$C(CH$_3$)2, O) are purchased or prepared by reaction of the corresponding cyclic epoxide and an appropriate aryl grignard reagent, followed by oxidation of the resulting alcohol, as would be known by one skilled in the art. Reaction of A with the phosphonium ylide results in the α,β-unsaturated ester, which is isomerized under basic conditions to B. Olefin hydrogenation under standard conditions (H$_2$, Pd on C) gives the cis substituted product C. This material (or related acid chloride) is cyclized using standard Friedel-Crafts conditions (Lewis acid) to give the tricyclic tetralone D. This material is subjected to palladium catalyzed aryl coupling conditions to form the 2-aryl-1-tetralone E. Ketone reduction to give alcohol F, followed by dehydration gave olefin G. This material is reduced using catalytic hydrogenation to yield the all cis tetralin H. Demethylation using boron tribromide provides the product bis phenol I. All products were isolated using techniques well known by those skilled in the art.

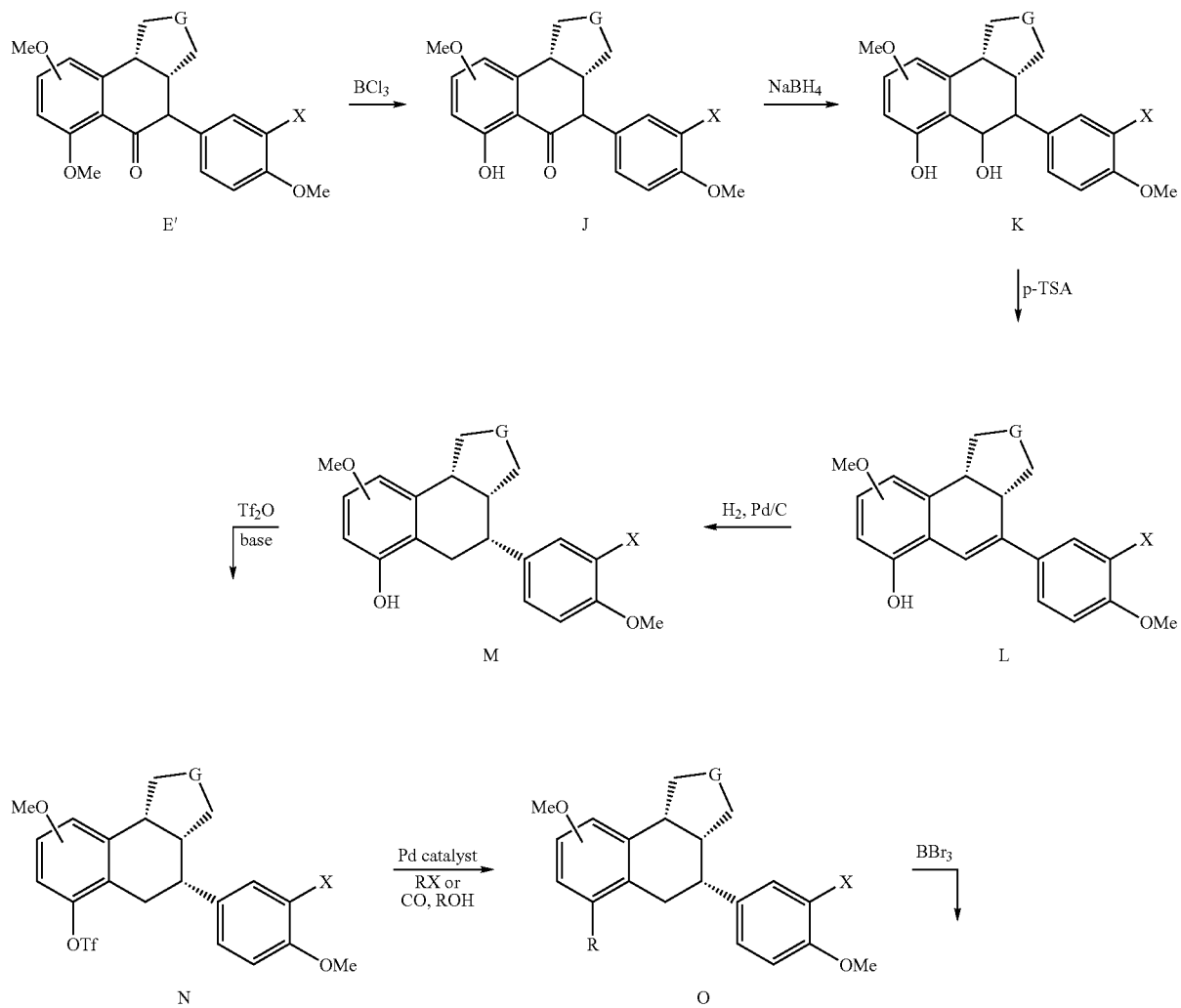

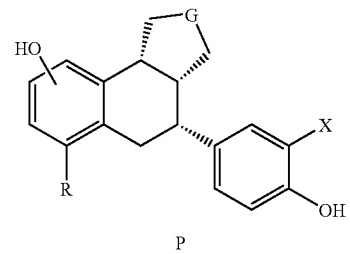

In Scheme 2, starting material E' is prepared according to Scheme 1, as previously described. Mono-demethylation is accomplished using boron trichloride to give J. Reduction give K, dehydration gives L and hydrogenation gives M, as previously described. Phenol M is converted to the aryl triflate N, which can be used to incorporate various R-substituted intermediates N through the use of palladium catalyzed coupling reactions, as are well known to those skilled in the art. Final bis phenols P are prepared by boron tribromide demethylation, as previously described. In several instances, functional group interconversions, known to those skilled in the art, are performed on intermediates O to prepare related compounds. These are described in the experimental section.

In Scheme 3, starting material H' is prepared according to Scheme 1. This material is either brominated to produce Q, or acetylated to produce R. Q is further substituted by conversion to the aryl lithium, followed by reaction with various reactive electrophilic agents, as are known to one skilled in the art. Both Q and R were subjected to various other functional group interconversions, known to those skilled in the art, to produce related compounds. These procedures are described in the experimental section. Intermediates S are demethylated with boron tribromide, as previously described, to produce bis phenol T.

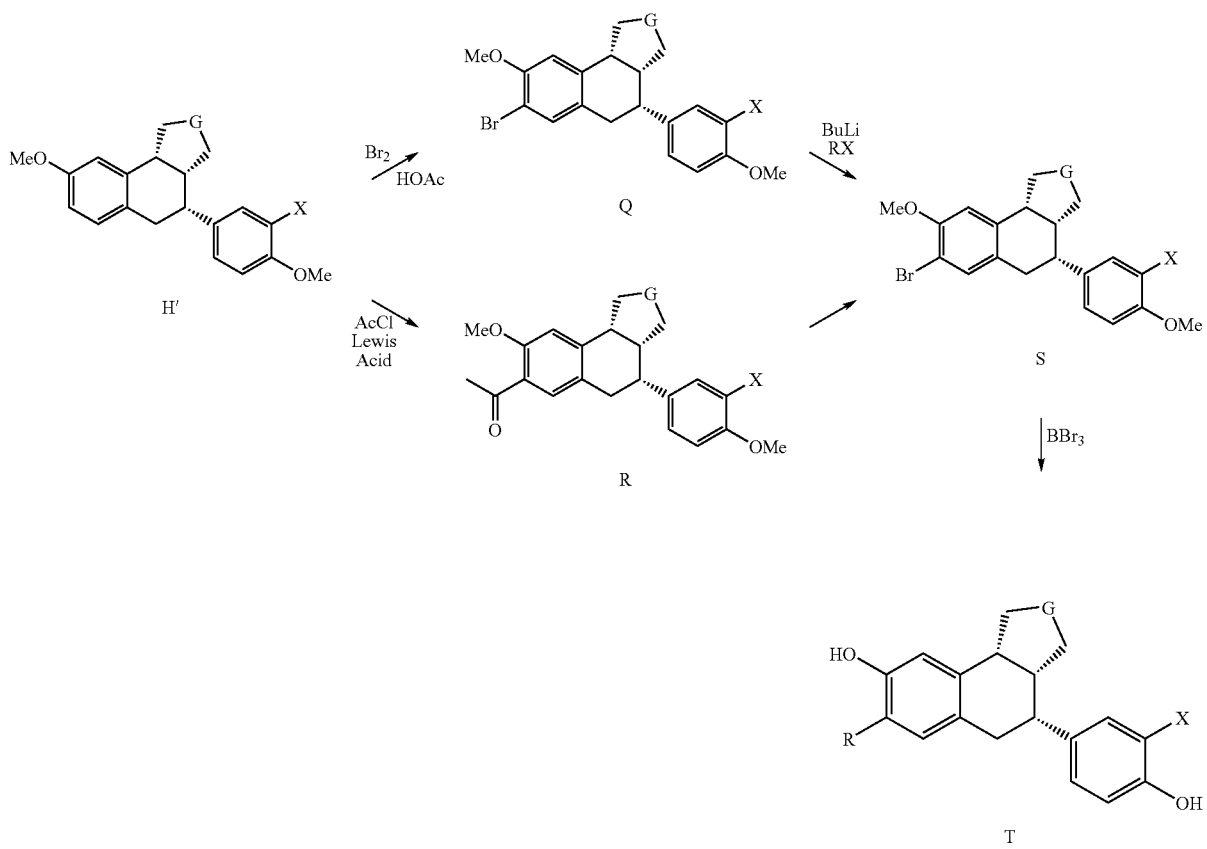

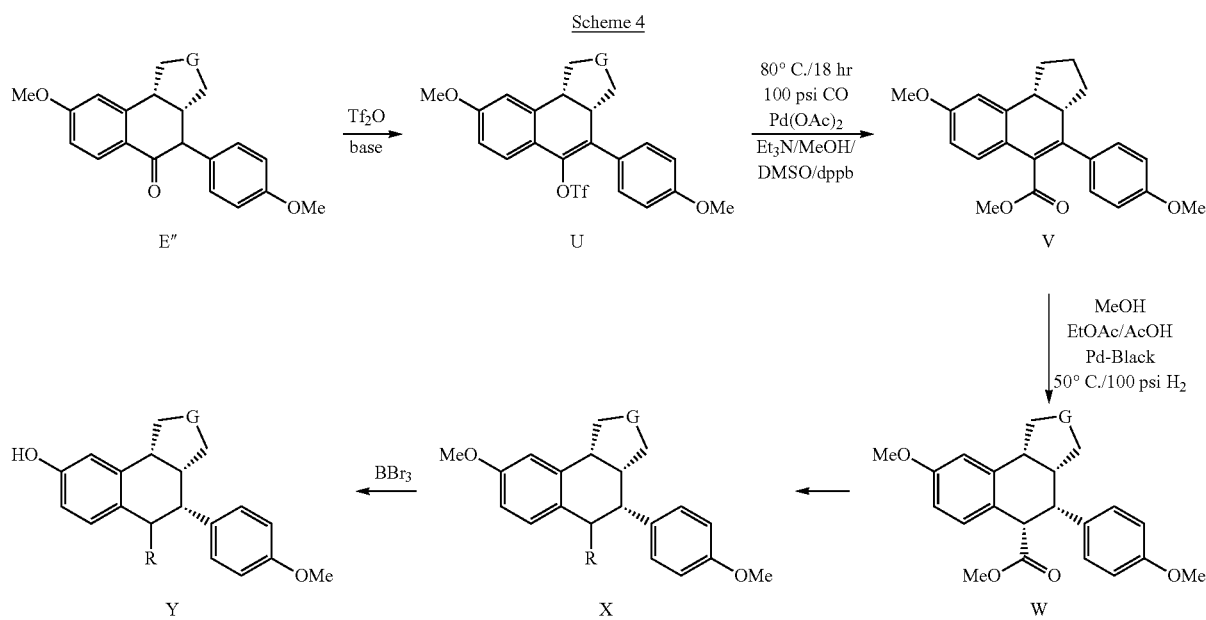

Scheme 4

In Scheme 4, starting material E" is prepared according to Scheme 1. This material is converted to vinyl triflate U and then converted to ester V via palladium catalyzed carbonylation chemistry. Compound V is hydrogenated using palladium black to give W. The ester functionality in intermediate W is used to provide various substituted analogs X, using chemistry known to one skilled in the art. Final bis phenols Y were prepared using standard boron tribromide demethylation conditions, as preciously described.

PREPARATION 1

[2-(3-Methoxy-phenyl)-cyclohexylidene]-acetic acid ethyl ester

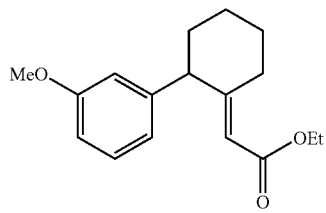

Combine 2-(3-methoxyphenyl)-cyclohexanone (5.0 g, 24.5 mmol), carbethoxymethylene triphenylphosphorane (15.4 g, 44.1 mmol), and toluene (150 mL), stir and heat at reflux. After 22 hours, cool to ambient temperature and concentrate under vacuum. Add ether and filter off the triphenylphosphine oxide precipitate and concentrate the ether filtrate. Flash chromatograph with 0% to 10% ethyl acetate/hexanes to yield the titled compound (6.71 g, 99%) as a clear oil. TLC Rf=0.58 in 8:1 hexanes:ethyl acetate. $^1$H NMR (CDCl$_3$): 7.25 (m, 1H), 6.81-6.79 (m, 3H), 6.73 (s, 1H), 5.14 (s, 1H), 4.07 (q, J=14.4, 7.2, 2H), 3.80 (s, 3H), 3.80-3.69 (m, 1H), 3.39-3.36 (m, 1H), 2.20-2.16 (m, 1H), 2.06-2.03 (m, 1H), 1.96-1.87 (m, 3H), 1.65-1.54 (m, 2H), 1.2 (t, J=1.2, 8, 3H).

PREPARATION 2

[2-(3-Methoxy-phenyl)-cyclohex-1-enyl]-acetic acid ethyl ester

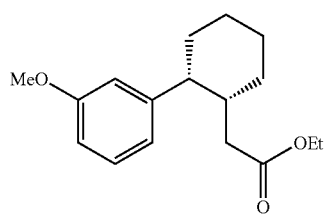

Combine [2-(3-methoxy-phenyl)-cyclohexylidene]-acetic acid ethyl ester (839.4 mg, 3.06 mmol), sodium ethoxide (62.5 mg, 0.92 mmol), and DMSO (6.0 mL), stir, and heat at 100° C. After 2 hours, cool to ambient temperature and extract the organic layer with ethyl acetate. Wash the ethyl acetate layer 5× with brine and dry the organic layer over sodium sulfate, and concentrate in vacuo to yield the titled compound (769.6 mg, 92%) as a clear oil. TLC Rf=0.58 in 8:1 hexanes: ethyl acetate. $^1$H NMR (CDCl$_3$): 7.21 (m, 1H), 6.75 (m, 3H), 4.11 (q, 2H, J=7.2 Hz), 3.79 (s, 3H), 2.91 (s, 2H), 2.28 (m, 2H), 2.12 (m, 2H), 1.72 (m, 4H), 1.24 (t, 3H, J=7.3 Hz).

PREPARATION 3

[2-(3-Methoxy-phenyl)-cyclohexyl]-acetic acid ethyl ester

Combine [2-(3-methoxy-phenyl)-cyclohex-1-enyl]-acetic acid ethyl ester (9.91 g, 36.0 mmol), 10% Pd on carbon (2.06 g, 14.4 mmol), and ethanol (90 mL) and tetrahydrofuran (5 mL), degas, and add 50 psi H$_2$ at room temperature. After 18 hours, filter off the Pd catalyst over celite eluting with ethyl acetate. Concentrate and flash chromatograph with 0% to 20% ethyl acetate/hexanes to yield the titled compound (8.89 g, 89%) as a clear oil. TLC Rf=0.42 in 6:1 hexanes:ethyl acetate. $^1$H NMR (CDCl$_3$):$^1$H NMR (CDCl$_3$): 7.21 (t, 1H, J=8.1 Hz), 6.78 (d, 2H, J=7.5 Hz), 6.72 (s, 1H), 3.98 (q, 2H, J=7.0 Hz), 3.80 (m, 3H), 2.89 (m, 1H), 2.51 (m, 1H), 2.31 (m, 1H), 1.97 (m, 1H), 1.88 (m, 1H), 1.72 (m, 4H), 1.44 (m, 3H), 1.16 (t, 3H, J=6.6 Hz).

PREPARATION 4

2-(3-Methoxy-phenyl)-cyclohexane carboxylic acid

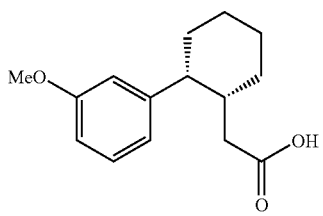

Combine [2-(3-methoxy-phenyl)-cyclohexyl]-acetic acid ethyl ester (13.3 g, 48.1 mmol), ethanol (100.0 mL), and lithium hydroxide aqueous (24 mL), stir at reflux temperature. After 48 hours, add 5N HCl until reaction is acidic, then extract with ethyl acetate and wash with brine. Dry the organic phase with anhydrous sodium sulfate then concentrate to yield the titled compound (11.31 g, 95%) as a white solid. TLC Rf=0.19 in 4:1 hexanes:ethyl acetate. $^1$H NMR (CDCl$_3$): 7.24 (m, 1H), 6.80 (d, 1H, J=7.9 Hz), 6.75 (m, 2H), 3.82 (s, 3H), 2.93 (m, 1H), 2.53 (m, 1H), 2.38 (m, 1H), 2.04 (m, 1H), 1.81 (m, 5H), 1.51 (m, 3H).

PREPARATION 5

6-Methoxy-2,3,4,4a,10,10a-hexahydro-1H-phenanthren-9-one

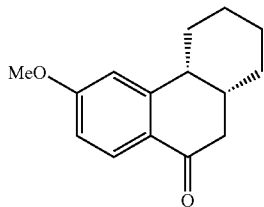

Combine 2-(3-methoxy-phenyl)-cyclohexane carboxylic acid (11.50 g, 46.3 mmol), methylene chloride (200 mL), catalytic DMF (4.0 mL) and slowly add oxalyl chloride (4.8 mL, 55.6 mmol), stir at room temperature. After 1.5 hours, at 0° C. add TiCl$_4$ (12.7 mL, 115.78 mmol) and let reaction warm to room temperature. After 3.5 hours, quench reaction with ice water and add 5N HCl. Allow reaction mixture to stir for 30 minutes then extract with ethyl acetate and wash with sodium bicarbonate solution (aq), then Brine. Dry the organic phase with anhydrous sodium sulfate then concentrate and flash chromatograph using 0% to 20% ethyl acetate/hexanes to yield the titled compound (9.91 g, 93%) as a yellow oil. TLC Rf=0.26 in 5:1 hexanes:ethyl acetate $^1$H NMR (CDCl$_3$): 8.01 (d, 1H, J=8.8 Hz), 6.83 (m, 1H), 6.72 (m, 1H), 3.86 (s, 3H), 2.89 (m, 2H), 2.45 (m, 2H), 1.60 (m, 8H).

PREPARATION 6

6-Methoxy-10-(4-methoxy-phenyl)-2,3,4,4a,10,10a-hexahydro-1H-phenanthren-9-one

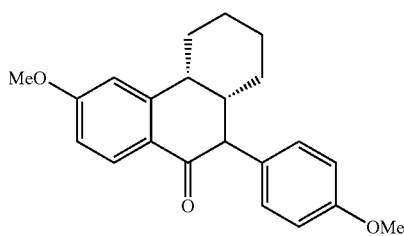

Combine 6-methoxy-2,3,4,4a,10,10a-hexahydro-1H-phenanthren-9-one (1.0 g, 4.3 mmol), 4-bromoanisole (0.81 g, 4.3 mmol), palladium acetate (49.0 mg, 0.218 mmol), t-butyl phosphine (0.133 g, 0.658 mmol), sodium t-butoxide (0.457 g, 4.7 mmol), tetrahydrofuran (38.0 mL), and stir under nitrogen atmosphere at 80° C. in a glass bomb. After 18 hours, quench reaction with acetic acid (5 mL) in a glove box and extract with ethyl acetate. Wash the ethyl acetate with sodium bicarbonate solution and then brine, dry over sodium sulfate, and concentrate in vacuo. Add diethyl ether and collect precipitate to yield the titled compound (0.78 g, 55%) as a white solid. TLC Rf=0.26 in 5:1 hexanes:ethyl acetate. $^1$H NMR (CDCl$_3$): 8.04 (d, 1H, J=8.8 Hz), 7.06 (d, 2H, J=8.4 Hz), 6.86 (m, 3H), 6.75 (m, 1H), 3.89 (m, 4H), 3.80 (s, 3H), 3.01 (m, 1H), 2.65 (m, 1H), 1.81 (m, 3H), 1.46 (m, 5H).

PREPARATION 7

6-Methoxy-10-(4-methoxy-phenyl)-1,2,3,4,4a,9,10,10a-octahydro-phenanthren-9-ol

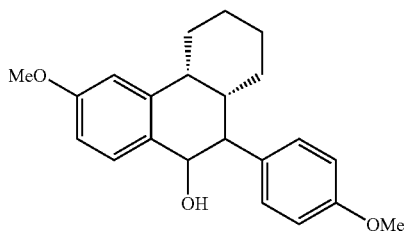

Combine 6-methoxy-10-(4-methoxy-phenyl)-2,3,4,4a,10,10a-hexahydro-1H-phenanthren-9-one (58.0 mg, 0.17 mmol), sodium borohydride (52.0 mg, 1.40 mmol), ethanol (3.0 mL), tetrahydrofuran (3.0 mL), stir, and reflux under a nitrogen atmosphere. After 2 hours, cool to ambient temperature, and concentrate in vacuo. Add ethyl acetate to reaction mixture, wash with sat ammonium chloride solution(aq), Brine, and dry over sodium sulfate. Concentrate to yield the titled compound (57.0 mg, 99%) as a white solid. TLC Rf=0.12 in 6:1 hexanes:ethyl acetate. $^1$H NMR (CDCl$_3$): 7.50

(d, 1H, J=8.8 Hz), 7.20 (d, 2H, J=8.4 Hz), 6.93 (d, 2H, J=8.4 Hz), 6.80 (dd, 1H, J=8.6, 2.4 Hz), 6.66 (m, 1H), 4.77 (d, 1H, J=9.7 Hz), 3.82 (m, 6H), 3.05 (m, 1H), 2.85 (m, 1H), 2.35 (m, 1H), 1.75 (m, 4H), 1.40 (m, 5H).

PREPARATION 8

6-Methoxy-10-(4-methoxy-phenyl)-1,2,3,4,4a,10a-hexahydro-phenanthrene

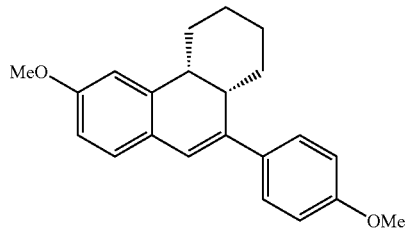

Combine 6-methoxy-10-(4-methoxy-phenyl)-1,2,3,4,4a,9,10,10a-octahydro-phenanthren-9-ol (184.3 mg, 0.54 mmol), p-toluene sulfonic acid (20.0 mg, 0.11 mmol), benzene (5 mL), stir, and reflux under nitrogen atmosphere. After 1.5 hours, cool reaction to ambient temperature, add ethyl acetate, wash sat sodium bicarbonate solution (aq), and then with brine, dry over sodium sulfate, and concentrate in vacuum. Flash chromatograph using 0% to 20% ethyl acetate/hexanes to yield the titled compound (147.6 mg, 85%) as a clear oil. TLC Rf=0.51 in 6:1 hexanes:ethyl acetate. $^1$H NMR (CDCl$_3$): 7.53 (d, 2H, J=8.8 Hz), 7.10 (d, 1H, J=7.9 Hz), 6.93 (m, 3H), 6.72 (m, 2H), 3.85 (m, 6H), 3.21 (m, 1H), 2.79 (m, 1H), 2.49 (m, 1H), 1.80 (m, 1H), 1.58 (m, 4H), 1.30 (m, 2H).

PREPARATION 9

6-Methoxy-10-(4-methoxy-phenyl)-1,2,3,4,4a,9,10,10a-octahydro-phenanthrene

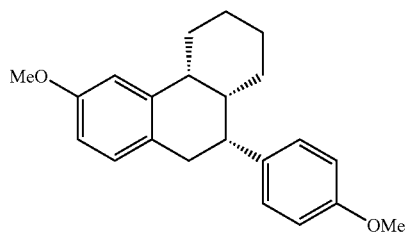

Combine 6-methoxy-10-(4-methoxy-phenyl)-1,2,3,4,4a,10a-hexahydro-phenanthrene (48.5 mg, 0.15 mmol), 10% Pd—C (5.4 mg, 0.04 mmol), and ethanol (3 mL) and tetrahydrofuran (3 mL), degas, and add H$_2$ at atmospheric pressure and at room temperature. After 18 hours, filter off the Pd catalyst over celite eluting with ethyl acetate. Concentrate and flash chromatograph with 0% to 20% ethyl acetate/hexanes to yield the titled compound (42.4 mg, 87%) as a clear oil. TLC Rf=0.51 in 6:1 hexanes:ethyl acetate. $^1$H NMR (CDCl$_3$): 7.25 (d, 2H, J=8.4 Hz), 7.11 (d, 1H, J=8.4 Hz), 6.97 (m, 1H), 6.90 (d, 2H, J=7.9 Hz), 6.75 (m, 1H), 3.82 (m, 6H), 3.19 (m, 3H), 2.87 (dd, 1H, J=15.0, 4.0 Hz), 2.49 (m, 1H), 2.04 (m, 1H), 1.65 (m, 2H), 1.45 (m, 1H), 1.29 (m, 1H), 1.15 (m, 3H).

PREPARATION 10 trans-2-(3-Methoxyphenyl)-cyclopentanol

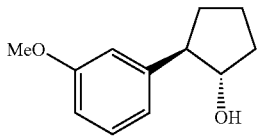

To a solution of 3-methoxyphenyl magnesium bromide 1.0M (59.4 ml, 59.4 mmoles) and copper(I) iodide (0.762 g, 4.0 mmoles), add (dropwise) a solution of cyclopentene oxide (5.2 ml, 59.4 mmoles) in tetrahydrofuran (5 ml) over 40 minutes. The reaction is exothermic and the temperature rises to 45° C. Cool the reaction to ambient temperature and quench with a 25% solution of ammonium chloride (40 ml), extract with ether and shake with brine. Dry the organic layer over sodium sulfate and concentrate in vacuo to yield an oil which is flash chromatographed on silica with 14-25% ethyl acetate/hexanes to yield 6.43 g of the titled compound. $^1$H NMR (CDCl$_3$): 7.23 (d, J=8.4, 1H), 6.86 (d, J=7.6 Hz, 1H), 6.81 (s, 1H), 6.77 (m, 1H), 4.15 (m, 1H), 3.81 (s, 3H), 2.86 (m, 1H), 2.18-2.04 (m, 2H), 1.9-1.6 (m, 5H).

PREPARATION 11

2-(3-Methoxyphenyl)-cyclopentanone

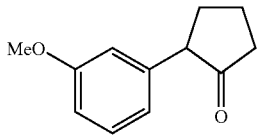

To a solution of 2-(3-methoxyphenyl)-cyclopentanol (6.4 g, 0.033 mmoles) in 140 ml of methylene chloride, add a mixture of pyridine chlorochromate (14.4 g, 0.066 mmoles), and silica gel (14.4 g). After 1.5 hours, an equivalent amount of oxidizing agent and silica gel is added and the reaction is stirred an additional 3.5 hours. Reduce the solvent in half in vacuo at 35° C. and chromatograph on silica with 3-1 hexanes-ethyl acetate to yield 4.34 g of the titled compound. $^1$H NMR (CDCl$_3$): 7.25 (m, 1H), 6.81-6.74 (m, 3H), 3.8 (s, 3H), 3.31 (m, 1H), 2.5 (m, 2H), 2.3 (m, 1H), 2.1 (m, 2H), 1.9 (m, 1H).

PREPARATION 12

[2-(3-Methoxy-phenyl)-cyclopent-1-enyl]-acetic acid ethyl ester

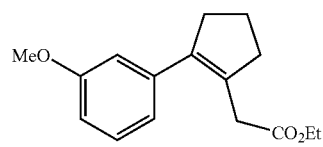

Reflux a solution of 2-(3-methoxy-phenyl)-cyclopentanone (4.34 g 22.8 mmoles), and (carboethoxymethylene)-triphenylphosphorane (14.31 g, 41.1 mmoles) in 130 ml of xylenes for 15 hours. Concentrate in vacuo at 40° C. and slurry with ether. Remove triphenyl phosphine oxide by vacuum filtration, and chromatographed on silica with 14% ethyl acetate/hexanes. to yield the 4.83 g of the titled compound. $^1$H NMR (CDCl$_3$): 7.26 (m, 1H), 6.9 (m, 2H), 6.8 (m, 1H), 4.17 (q, J=7.2, 2H), 3.81 (s, 3H), 3.22 (s, 2H), 2.76 (m, 2H), 2.58 (m, 2H), 1.95 (m, 2H) 1.28 (m, 3H).

PREPARATION 13

[2-(3-Methoxy-phenyl)-cyclopentyl]-acetic acid ethyl ester

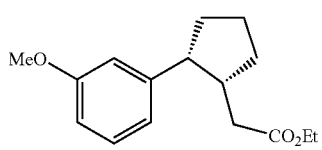

Preparation 13 is prepared from preparation 12 in a manner similar to preparation 3. $^1$H NMR (CDCl$_3$): 7.2 (m, 1H), 6.7 (m, 3H), 4.02 (q, J=7.2, 2H), 3.8 (s, 3H), 3.27 (q, J=7.2, 1H), 2.64 (m, 1H), 2.06 (m, 1H), 1.9 (m, 5H), 1.7 (m, 1H) 1.5 (m, 1H) 1.18 (t, J=7.2, 3H).

PREPARATION 14

8-Methoxy-1,2,3,3a,4,9b-hexahydro-cyclopenta[a]naphthalen-5-one

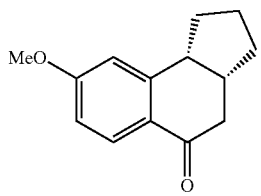

Heat a solution of [2-(3-methoxyphenyl)-cyclopentyl]-acetic acid ethyl ester (4.2 g, 16.0 mmoles) in polyphosphoric acid (27 g) at 100° C. for 3.5 hours. Cool the reaction to r.t. and add ice, water and methylene chloride cautiously. Extract the aqueous layer was 2× with additional methylene chloride, combine the organic layers and dry over anhydrous sodium sulfate. Concentrate in vacuo at 40° C. Chromatograph the crude product on silica with 11-17% ethyl acetate/hexanes to yield the titled compound (2.8 g, 81%) as a neat crystalline solid. $^1$H NMR (CDCl$_3$): 7.95 (d, J=8.8 Hz, 1H), 6.8 (dd, J=2.8 Hz, 6.4 Hz, 1H), 6.73(m, 1H), 3.86 (s, 3H), 3.19 (m, 1H), 2.72 (m, 1H), 2.53 (m, 2H), 2.18 (m, 1H), 2.0-1.75 (m, 5H).

PREPARATION 15

8-Methoxy-4-(4-methoxy-phenyl)-1,2,3,3a,4,9b-hexahydro-cyclopenta[a]naphthalen-5-one

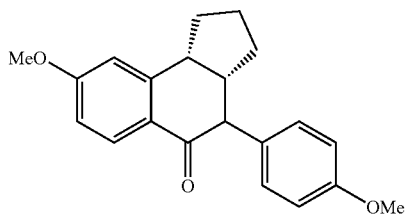

Preparation 15 is prepared from preparation 14 in a manner similar to preparation 6. $^1$H NMR (CDCl$_3$):8.0 (d, J=8.4 Hz, 1H), 7.2 (d, J=8.8 Hz, 2H), 6.9(d, J=8.8 Hz, 2H), 6.83 (m, 2H), 4.19 (d, J=4.8 Hz, 1H), 3.88 (s, 3H), 3.81 (s, 3H), 3.62 (m, 1H), 2.7 (m, 1H), 2.15 (m, 2H), 1.75 (m, 1H), 1.5 (m, 3H). MS calcd 322; MS (M+1) 323.

PREPARATION 16

8-Methoxy-4-(4-methoxy-phenyl)-2,3,3a,4,5,9b-hexahydro-1H-cyclopenta[a]naphthalen-5-ol

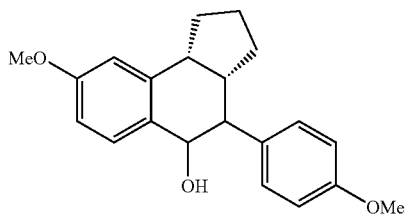

Preparation 16 is prepared from preparation 15 in a manner similar to preparation 7. $^1$H NMR (CDCl$_3$): 7.53 (d, J=8.8 Hz, 1H), 7.21 (d, J=8.8 Hz, 2H), 6.9(d, J=8.4 Hz, 2H), 6.83 (m, 3H), 4.71 (d, J=10.1 Hz, 1H), 3.82 (s, 3H), 3.81 (s, 3H), 3.2 (m, 1H), 2.6 (m, 1H), 2.45 (m, 1H), 2.25 (m, 1H), 1.6 (m, 5H).

PREPARATION 17

8-Methoxy-4-(4-methoxy-phenyl)-2,3,3a,9b-tetrahydro-1H-cyclopenta[a]naphthalene

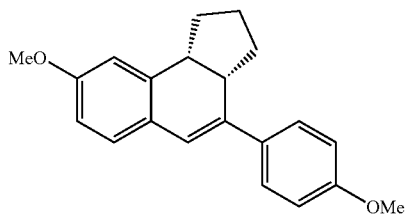

Preparation 17 is prepared from preparation 16 in a manner similar to preparation 8. $^1$H NMR (CDCl$_3$): 7.45 (d, J=8.8 Hz, 1H), 7.04 (d, J=8.4 Hz, 1H), 6.89(d, J=8.8 Hz, 2H), 6.8 (s, 1H), 6.7 (d, J=8 Hz, 1H), 6.55 (s, 1H), 3.83 (s, 3H), 3.82 (s, 3H), 3.39 (m, 1H), 3.24 (m, 1H), 2.15 (m, 2H), 2.0 (m, 1H), 1.55 (m, 3H).

PREPARATION 18

8-Methoxy-4-(4-methoxy-phenyl)-2,3,3a,4,5,9b-hexahydro-1H-cyclopenta[a]naphthalene

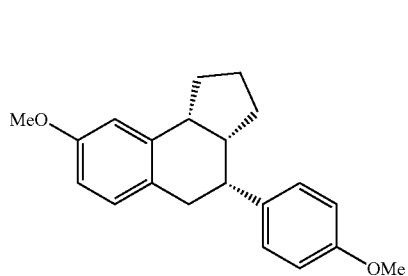

Preparation 18 is prepared from preparation 17 in a manner similar to preparation 9. $^1$H NMR (CDCl$_3$): 7.2 (d, J=8.4 Hz, 2H), 7.03 (d, J=7.9 Hz, 1H), 6.87(d, J=7.9 Hz, 2H), 6.74 (d, J=2.7 Hz, 1H), 6.75 (d, J=5.7 Hz, 1H), 3.8 (s, 6H), 3.4 (m, 1H), 3.1 (m, 2H), 2.68 (d, J=13.2 Hz, 1H), 2.56 (m, 1H), 2.2 (m, 1H), 1.2-1.6 (m, 5H).

PREPARATION 19 trans-2-(3,5-Dimethoxy-phenyl)-cyclopentanol

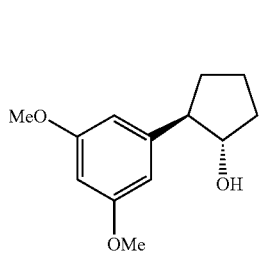

Preparation 19 is prepared from cyclopentene oxide and 1-bromo-3,5-dimethoxybenzene in a manner similar to preparation 10. $^1$H NMR (CDCl$_3$): 6.41 (s, 2H), 6.33(s, 1H), 4.15 (dd, J=7.5 Hz, 1H), 3.78 (s, 6H), 2.81 (dd, J=9.2 Hz, 1H), 2.1 (m, 2H), 1.9-1.5 (m, 6H).

PREPARATION 20

2-(3,5-Dimethoxy-phenyl)-cyclopentanone

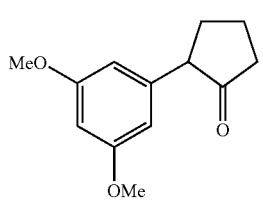

Preparation 20 is prepared from preparation 19 in a manner similar to preparation 11. $^1$H NMR (CDCl$_3$): 6.34 (s, 3H), 4.15 (dd, J=7.5 Hz, 1H), 3.77 (s, 6H), 3.25 (dd, J=11.1, 8.3 Hz, 1H), 2.45 (m, 2H), 2.3 (m, 1H), 2.1 (m, 2H), 1.8 (m, 1H).

PREPARATION 21

[2-(3,5-Dimethoxy-phenyl)-cyclopent-1-enyl]-acetic acid ethyl ester

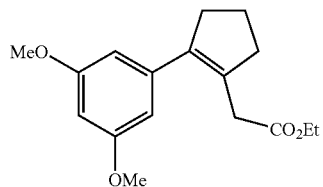

Preparation 21 is prepared from preparation 20 in a manner similar to preparations 1 and 2. $^1$H NMR (CDCl$_3$): 6.5 (s, 2H), 6.4 (s, 1H), 4.16 (q, J=7 Hz, 2H), 3.8 (s, 6H), 3.22(s, 2H), 2.73 (m, 2H), 2.57 (m, 2H), 1.94 (m, 2H), 1.27 (t, J=7 Hz, 3H).

PREPARATION 22

[2-(3,5-Dimethoxy-phenyl)-cyclopentyl]-acetic acid ethyl ester

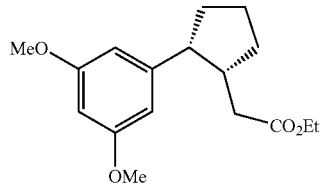

Preparation 22 is prepared from preparation 21 in a manner similar to preparation 3. $^1$H NMR (CDCl$_3$): 6.3 (s, 3H), 4.03 (q, J=7 Hz, 2H), 3.77 (s, 6H), 3.21(dd, 1H, J=7.5 Hz), 2.2-1.4 (m, 6H), 2.57 (m, 2H), 1.94 (m, 2H), 1.18 (t, J=7 Hz, 3H).

PREPARATION 23

6,8-Dimethoxy-1,2,3,3a,4,9b-hexahydro-cyclopenta[a]naphthalen-5-one

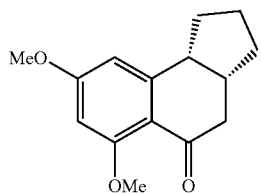

Preparation 23 is prepared from preparation 22 in a manner similar to preparation 14. MS m/z 247 (M+1).

PREPARATION 24

6,8-Dimethoxy-4-(4-methoxy-phenyl)-1,2,3,3a,4,9b-hexahydro-cyclopenta[a]naphthalen-5-one

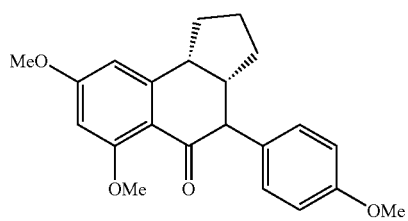

Preparation 24 is prepared from preparation 23 in a manner similar to preparation 6. MS m/z 353 (M+1).

PREPARATION 25

6,8-Dimethoxy-4-(4-methoxy-phenyl)-2,3,3a,4,5,9b-hexahydro-1H-cyclopenta[a]naphthalen-5-ol

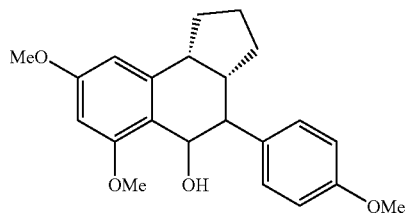

Preparation 25 is prepared from preparation 24 in a manner similar to preparation 7. ¹H NMR (CDCl₃): 7.45 (d, J=8.4 Hz, 2H), 6.95 (m, 1H), 6.88 (d, J=8.8 Hz, 1H), 6.64, 6.5(s, 1 H diasteromers), 6.4, 6.3(s, 1H, diastereomers) 3.94 (d, J=9.3 Hz, 1H)3.82 (s, 9H), 3.33-3.1 (series of m, 2H), 2.2-1.9 (m, 2H), 1.56 (m, 5H).

PREPARATION 26

6,8-Dimethoxy-4-(4-methoxy-phenyl)-2,3,3a,9b-tetrahydro-1H-cyclopenta[a]naphthalene

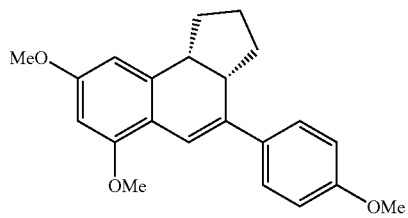

Preparation 26 is prepared from preparation 25 in a manner similar to preparation 8. MS m/z 337 (M+1).

PREPARATION 27

6,8-Dimethoxy-4-(4-methoxy-phenyl)-2,3,3a,4,5,9b-hexahydro-1H-cyclopenta[a]naphthalene

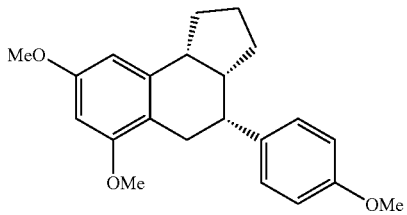

Preparation 27 is prepared from preparation 26 in a manner similar to preparation 9. ¹H NMR (CDCl₃): 7.24 (d, J=8.4 Hz, 2H), 6.86 (d, J=8.4 Hz, 2H), 6.34 (s, 1H), 3.8 (s, 6H), 3.79 (s, 3H), 3.4 (m, 1H), 3.19-2.95 (m, 2H), 2.64(dd, J=14.5, 14.1 1H) 2.5 (m, 1H), 2.19 (m, 1H), 1.7-1.3 (m, 5H).

PREPARATION 28

4-(3-Methoxy-phenyl)-dihydro-furan-3-one

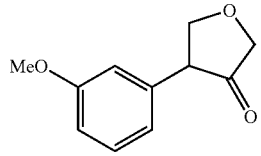

Combine 4-(3-methoxy-phenyl)-tetrahydro-furan-3-ol (10.58 g, 54.0 mmol), pyridine chlorochromate (35.22 g, 163.0 mmol), silica gel (35.0 g), and dichloromethane (200 mL), stir at room temperature. After 3 hours, add ether and filter off the silica gel through a plug of Silica using 50% ethyl acetate/hexanes eluent. Concentrate and flash chromatograph with 10% to 40% ethyl acetate/hexanes to yield the titled compound (5.74 g, 55%) as a clear oil. TLC Rf=0.23 in 3:1 hexanes:ethyl acetate. ¹H NMR (CDCl₃): 7.30 (m, 1H), 6.85 (m, 3H), 4.68 (t, 1H, J=9.0 Hz), 4.31 (t, 1H, J=8.8 Hz), 4.19 (d, 1H, J=17.2 Hz), 4.08 (d, 1H, J=17.2 Hz), 3.84 (s, 3H), 3.70 (t, 1H, J=8.1 Hz).

PREPARATION 29

[4-(3-Methoxy-phenyl)-2,5-dihydro-furan-3-yl]-acetic acid ethyl ester

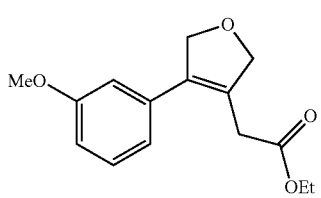

Preparation 29 is prepared from preparation 28 in a manner similar to preparations 1 and 2. TLC Rf=0.25 in 4:1 hexanes: ethyl acetate. ¹H NMR (CDCl₃): 7.32 (m, 1H), 6.90 (m, 3H), 5.01 (m, 2H), 4.90 (m, 2H), 4.21 (q, 2H, J=7.0 Hz), 3.86 (s, 3H), 3.32 (s, 2H), 1.31 (t, 3H, J=7.3 Hz).

PREPARATION 30

[4-(3-Methoxy-phenyl)-tetrahydro-furan-3-yl]-acetic acid ethyl ester

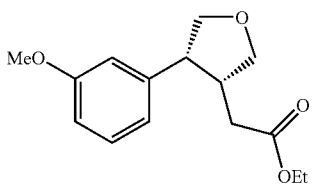

Preparation 30 is prepared from preparation 29 in a manner similar to preparation 3. TLC Rf=0.13 in 6:1 hexanes:ethyl acetate. $^1$H NMR (CDCl$_3$): 7.25 (m, 1H), 6.80 (m, 3H), 4.14 (m, 5H), 3.83 (s, 3H), 3.64 (t, 1H, J=8.4 Hz), 3.53 (dt, 1H, J=6.8, 3.8 Hz), 3.01 (dt, 1H, J=15.3, 7.6 Hz), 2.04 (m, 2H), 1.23 (t, 3H, J=7.3 Hz).

PREPARATION 31

[4-(3-Methoxy-phenyl)-tetrahydro-furan-3-yl]-acetic acid

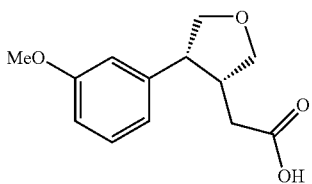

Preparation 31 is prepared from preparation 30 in a manner similar to preparation 4. TLC Rf=0.13 in 1:1 hexanes:ethyl acetate. $^1$H NMR (DMSO): 12.10 (s, 1H), 7.25 (t, 1H, J=7.9 Hz), 6.80 (m, 3H), 4.00 (m, 3H), 3.74 (s, 3H), 3.46 (m, 2H), 2.82 (m, 1H), 1.87 (m, 2H).

PREPARATION 32

8-Methoxy-1,3a,4,9b-tetrahydro-3H-naphtho[1,2-c]furan-5-one

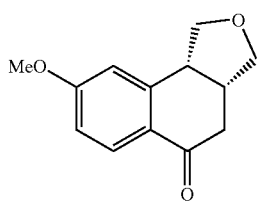

Preparation 32 is prepared from preparation 31 in a manner similar to preparation 5. TLC Rf=0.11 in 2:1 hexanes:ethyl acetate. $^1$H NMR (CDCl$_3$): 8.03 (d, 1H, J=8.8 Hz), 6.89 (dd, 1H, J=8.6, 2.4 Hz), 6.72 (d, 1H, J=2.2 Hz), 4.34 (t, 1H, J=8.4 Hz), 4.11 (dd, 1H, J=8.6, 5.5 Hz), 3.91 (m, 4H), 3.76 (dd, 1H, J=8.6, 3.3 Hz), 3.63 (q, 1H, J=7.8 Hz), 3.04 (m, 1H), 2.74 (m, 2H).

PREPARATION 33

8-Methoxy-4-(4-methoxy-phenyl)-1,3a,4,9b-tetrahydro-3H-naphtho[1,2-c]furan-5-one

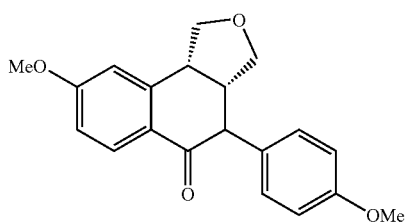

Preparation 33 is prepared from preparation 32 in a manner similar to preparation 6. TLC Rf=0.16 in 2:1 hexanes:ethyl acetate. $^1$H NMR (CDCl$_3$): 8.06 (d, 1H, J=8.8 Hz), 7.14 (d, 2H, J=8.8 Hz), 6.93 (m, 3H), 6.79 (d, 1H, J=1.8 Hz), 4.30 (m, 2H), 4.21 (m, 1H), 3.87 (m, 9H), 3.22 (m, 1H).

PREPARATION 34

8-Methoxy-4-(4-methoxy-phenyl)-1,3,3a,4,5,9b-hexahydro-naphtho[1,2-c]furan-5-ol

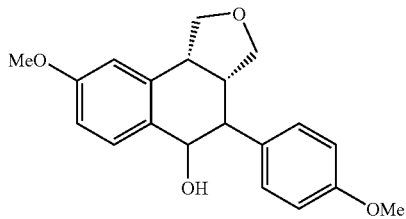

Preparation 34 is prepared from preparation 33 in a manner similar to preparation 7. TLC Rf=0.51 in 2:1 hexanes:ethyl acetate. $^1$H NMR (CDCl$_3$): 7.59 (m, 1H), 7.26 (m, 2H), 6.89 (m, 3H), 6.66 (d, 1H, J=2.6 Hz), 4.81 (d, 1H, J=10.1 Hz), 4.36 (t, 1H, J=8.4 Hz), 3.82 (m, 7H), 3.60 (m, 2H), 3.14 (m, 1H), 2.87 (m, 1H), 2.73 (t, 1H, J=11.2 Hz).

PREPARATION 35

8-Methoxy-4-(4-methoxy-phenyl)-1,3,3a,9b-tetrahydro-naphtho[1,2-c]furan

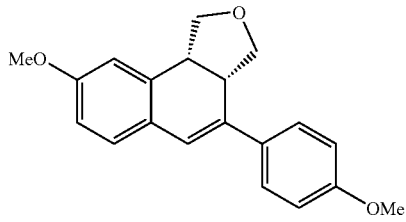

Preparation 35 is prepared from preparation 34 in a manner similar to preparation 8. TLC Rf=0.54 in 1:1 hexanes:ethyl acetate. $^1$H NMR (CDCl$_3$): 7.44 (d, 2H, J=8.8 Hz), 7.14 (d, 1H, J=8.4 Hz), 6.94 (d, 2H, J=9.2 Hz), 6.77 (m, 2H), 6.68 (s, 1H), 4.37 (t, 2H, J=7.7 Hz), 3.86 (m, 7H), 3.71 (m, 2H), 3.60 (t, 1H, J=7.3 Hz).

PREPARATION 36

8-Methoxy-4-(4-methoxy-phenyl)-1,3,3a,4,5,9b-hexahydro-naphtho[1,2-c]furan

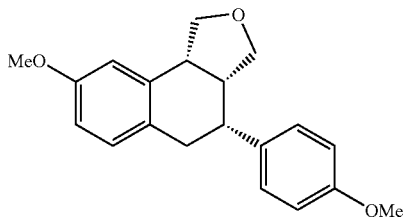

Preparation 36 is prepared from preparation 35 in a manner similar to preparation 9. TLC Rf=0.31 in 2:1 hexanes:ethyl acetate. $^1$H NMR (CDCl$_3$): 7.22 (d, 2H, J=8.4 Hz), 7.12 (d, 1H, J=8.4 Hz), 6.91 (d, 2H, J=8.8 Hz), 6.75 (m, 2H), 4.25 (t, 1H, J=8.1 Hz), 3.84 (m, 6H), 3.67 (m, 3H), 3.57 (m, 1H), 3.11 (m, 3H), 2.80 (d, 1H, J=14.5 Hz).

PREPARATION 37

10-(3-Fluoro-4-methoxy-phenyl)-6-methoxy-2,3,4,4a,10,10a-hexahydro-1H-phenanthren-9-one

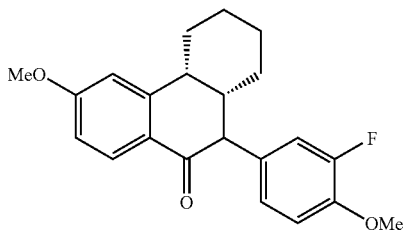

Preparation 37 is prepared from preparation 5 and 4-bromo-2-fluoroanisol in a manner similar to preparation 6. TLC Rf=0.13 in 6:1 hexanes:ethyl acetate. $^1$H NMR (CDCl$_3$): 8.06 (d, 1H, J=8.8 Hz), 6.93 (m, 4H), 6.78 (d, 1H, J=2.6 Hz), 3.91 (m, 8H), 3.04 (m, 1H), 2.67 (m, 1H), 1.85 (m, 3H), 1.54 (m, 4H).

PREPARATION 38

10-(3-Fluoro-4-methoxy-phenyl)-6-methoxy-1,2,3,4,4a,9,10,10a-octahydro-phenanthren-9-ol

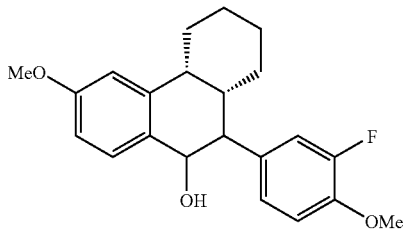

Preparation 38 is prepared from preparation 37 in a manner similar to preparation 7. TLC Rf=0.20 in 4:1 hexanes:ethyl acetate. $^1$H NMR (CDCl$_3$): 7.53 (d, 1H, J=8.8 Hz), 7.02 (m, 3H), 6.84 (dd, 1H, J=8.8, 2.6 Hz), 6.69 (d, 1H, J=2.6 Hz), 4.79 (d, 1H, J=9.7 Hz), 3.94 (s, 3H), 3.84 (s, 3H), 3.09 (t, 1H, J=11.0 Hz), 2.88 (m, 1H), 2.35 (m, 1H), 1.79 (m, 5H), 1.37 (m, 3H).

PREPARATION 39

10-(3-Fluoro-4-methoxy-phenyl)-6-methoxy-1,2,3,4,4a,9,10a-hexahydro-phenanthrene

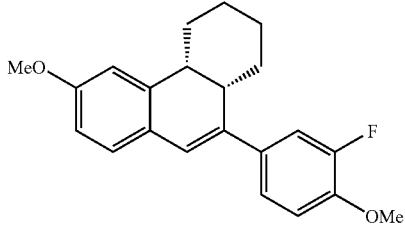

Preparation 39 is prepared from preparation 38 in a manner similar to preparation 8. TLC Rf=0.36 in 6:1 hexanes:ethyl acetate. $^1$H NMR (CDCl$_3$): 7.34 (m, 2H), 7.13 (d, 1H, J=8.4 Hz), 6.99 (m, 2H), 6.76 (m, 2H), 3.95 (s, 3H), 3.88 (s, 3H), 3.23 (d, 1H, J=4.0 Hz), 2.77 (m, 1H), 2.52 (d, 1H, J=14.1 Hz), 1.83 (m, 1H), 1.61 (m, 4H), 1.30 (m, 2H).

PREPARATION 40

10-(3-Fluoro-4-methoxy-phenyl)-6-methoxy-1,2,3,4,4a,9,10a-octahydro-phenanthrene

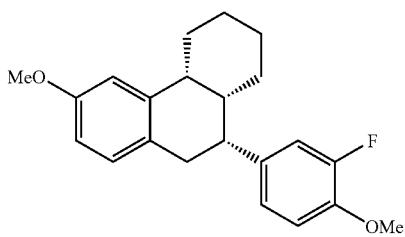

Preparation 40 is prepared from preparation 39 in a manner similar to preparation 9. TLC Rf=0.36 in 6:1 hexanes:ethyl acetate. $^1$H NMR (CDCl$_3$): 7.13 (m, 2H), 7.06 (m, 1H), 6.97 (m, 2H), 6.78 (dd, 1H, J=8.4, 2.6 Hz), 3.93 (s, 3H), 3.85 (s, 3H), 3.19 (m, 3H), 2.89 (d, 1H, J=11.5 Hz), 2.52 (d, 1H, J=14.5 Hz), 2.07 (m, 1H), 1.69 (m, 3H), 1.48 (m, 1H), 1.30 (d, 1H, J=10.6 Hz), 1.16 (m, 2H).

PREPARATION 41

2-Hydroxy-cyclohex-1-enecarboxylic acid ethyl ester

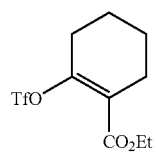

Combine 2-oxo-cyclohexanecarboxylic acid ethyl ester (10.0 g, 55.0 mmol), Hunig's base (23.0 mL, 132.0 mmol), dichloromethane (100.0 mL), and trifluoromethane sulphonic anhydride (11.1 mL, 66.0 mmol) at −78° C. and then stir at room temperarture for 18 hours under a nitrogen atmosphere. Add water, then wash with sat sodium bicarbonate solution, citric acid, then brine, and dry over sodium sulfate. Concentrate under vacuum and flash chromatograph using 10% to 40% DCM/hexanes eluent to yield the titled compound (13.6 g, 82%). TLC Rf=0.25 in 40% DCM/hexanes. $^1$H NMR (CDCl$_3$): 4.26 (q, 2H, J=7.0 Hz), 2.5 (m, 2H), 2.4 (m, 2H), 1.8 (m, 2H), 1.7 (m, 2H), 1.3 (t, 3H, J=7 Hz).

PREPARATION 42

2-(2-Methoxy-phenyl)-cyclohex-1-enecarboxylic acid ethyl ester

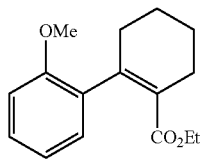

Combine 2-hydroxy-cyclohex-1-enecarboxylic acid ethyl ester (8.92 g, 29.5 mmol), 2-methoxyphenylboronic acid (5.0 g, 32.4 mmol), DMF (60.0 mL), methanol (20.0 mL), and sodium carbonate in water (40.0 g in 40 mL) at room temperature. Purge several times with nitrogen then add Pd(OAc)$_2$ (72.0 mg, 1 mmol %) and 1,4-bis(diphenyl phosphino)butane (170.0 mg) and purge again with nitrogen. Stir at 70° C. under nitrogen for 5 hours then filter reaction wash with Methanol and ethyl acetate. Concentrate reaction mixture on rotovap and add ethyl acetate. Wash 5 times with brine and dry over anhydrous sodium sulfate. Concentrate and flash chromatograph using 5 to 40% ethyl acetate/hexanes eluent to yield the titled compound (3.98 g, 52%). TLC Rf=0.25 in 10% ethyl acetate/hexanes. $^1$H NMR (CDCl$_3$): 7.2 (t, 1H, J=6.0 Hz), 6.9 (m, 3H),), 3.8 (m, 5H), 2.5 (m, 4H), 1.8 (m, 4H), 0.8 (t, 3H, J=7 Hz).

PREPARATION 43

2-(2-Methoxy-phenyl)-cyclohexanecarboxylic acid ethyl ester

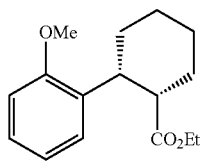

Preparation 43 is prepared from preparation 42 in a manner similar to preparation 3. TLC Rf=0.25 in 9:1 hexanes:ethyl acetate. $^1$H NMR (CDCl$_3$): 7.2 (d, 1H, J=6.0 Hz), 7.1 (t, 1H, J=8.0 Hz), 6.9 (t, 1H, J=8.0 Hz), 6.8 (d, 1H, J=7.0 Hz), 3.8 (m, 5H), 3.2 (m, 1H), 3.1 (m, 1H), 2.3 (m, 1H), 2.0 (m, 2H), 1.7 (m, 4H), 1.4 (m, 1H), 0.9 (t, 3H, J=7 Hz).

PREPARATION 44

[2-(2-Methoxy-phenyl)-cyclohexyl]-methanol

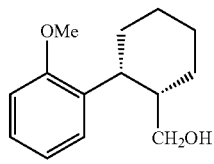

Combine 2-(2-methoxy-phenyl)-cyclohexanecarboxylic acid ethyl ester (2.34 g, 8.9 mmol), lithium aluminum hydride (1.02 g, 26.7 mmol), and tetrahydrofuran (30.0 mL) at room temperature. Stir at rm temperature under nitrogen for 2 hours then add Rochelle's salt and ethyl acetate. Stir 18 hours then separate layers and wash with brine then dry over anhydrous sodium sulfate. Concentrate to yield the titled compound (1.86 g, 95%). TLC Rf=0.08 in 10% ethyl acetate/hexanes. $^1$H NMR (CDCl$_3$): 7.2 (m, 2H), 6.9 (m, 2H), 3.8 (s, 3H), 3.5 (m, 1H), 3.4 (m, 1H), 3.3 (m, 1H), 2.3 (m, 1H), 1.8 (m, 2H), 1.5 (m, 6H).

PREPARATION 45

Methanesulfonic acid 2-(2-methoxy-phenyl)-cyclohexylmethyl ester

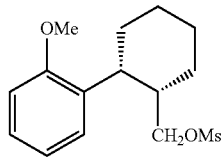

Combine [2-(2-methoxy-phenyl)-cyclohexyl]-methanol (0.725 g, 3.29 mmol), methanesulfonyl chloride (0.415 g, 3.62 mmol), 2,6-dimethylaminopyridine (80.0 mg, 0.66 mmol), Et$_3$N (1.0 mL, 7.24 mmol), and dichloromethane (30.0 mL) at 0° C. After 20 min stir at room temperature under nitrogen. Reaction stirred for 18 hours then add water and brine. Separate layers and dry over anhydrous sodium sulfate. Concentrate and flash chromatography using 5 to 30% ethyl acetate/hexanes to yield the titled compound (0.810 g, 83%). TLC Rf=0.25 in 30% ethyl acetate/hexanes. $^1$H NMR (CDCl$_3$): 7.2 (m, 1H), 7.1 (m, 1H), 6.9 (m, 2H), 4.3 (t, 1H, J=10.0 Hz), 3.9 (m, 4H), 3.3 (m, 1H), 2.8 (s, 3H), 2.6 (m, 1H), 1.8 (m, 6H), 1.5 (m, 2H).

PREPARATION 46

[2-(2-Methoxy-phenyl)-cyclohexyl]-acetonitrile

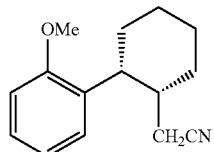

Combine 2-[2-(2-methoxy-phenyl)-cyclohexylmethoxy]-1,3,5-trimethyl-benzene (0.810 g, 2.71 mmol), sodium cyanide (2.13 g, 43.4 mmol), and $d^6$-DMSO (10.0 mL) at rm temperature. Heat and stir at 100° C. under nitrogen for 18 hours. Cool to room temperature and add ethyl acetate then add water and wash 5× with brine. Separate layers and dry over anhydrous sodium sulfate. Concentrate and flash chromatography using 0 to 30% ethyl acetate/hexanes to yield the titled compound (0.346 g, 56%). TLC Rf=0.43 in 20% ethyl acetate/hexanes. $^1$H NMR (CDCl$_3$): 7.2 (m, 1H), 7.0 (m, 1H), 6.9 (m, 2H), 3.8 (s, 3H), 3.3 (m, 1H), 2.5 (m, 1H), 2.3 (m, 1H), 2.1 (m, 1H), 1.8 (m, 6H), 1.4 (m, 2H).

PREPARATION 47

[2-(2-Methoxy-phenyl)-cyclohexyl]-acetaldehyde

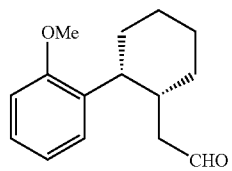

Combine [2-(2-methoxy-phenyl)-cyclohexyl]-acetonitrile (0.346 g, 1.51 mmol), diisobutylaluminum hydride (2.7 mL, 2.72 mmol), and ether (8.0 mL) at ⁻10° C. After 1 hour quenched reaction at 0° C. with 1N HCl and added ethyl acetate. Separate layers, wash with brine, and dry over anhydrous sodium sulfate. Concentrate to yield the titled compound (0.336 g, 96%). TLC Rf=0.08 in 5% ethyl acetate/hexanes. $^1$H NMR (CDCl$_3$): 9.3 (s, 1H), 7.2 (m, 1H), 7.0 (m, 1H), 6.9 (m, 2H), 3.8 (s, 3H), 3.3 (m, 1H), 2.8 (m, 1H), 2.3 (m, 1H), 2.2 (m, 2H), 1.6 (m, 7H).

PREPARATION 48

[2-(2-Methoxy-phenyl)-cyclohexyl]-acetic acid

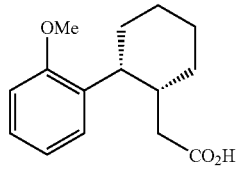

Combine [2-(2-methoxy-phenyl)-cyclohexyl]-acetaldehyde (0.336 g, 1.45 mmol), and acetone (10.0 mL). Add dropwise Jones reagent until color goes from green to orange and persists for several minutes (approximately 1.0 mL). Then concentrate on rotovap then add ethyl acetate and wash excess chromium away with brine washes. Dry over anhydrous sodium sulfate, concentrate to yield the titled compound (0.301 g, 84%). TLC Rf=0.13 in 20% ethyl acetate/hexanes. $^1$H NMR (CDCl$_3$): 7.2 (m, 1H), 7.0 (m, 1H), 6.8 (m, 2H), 3.8 (s, 3H), 3.3 (m, 1H), 2.6 (m, 1H), 2.3 (m, 1H), 2.0 (m, 1H), 1.6 (m, 8H).

PREPARATION 49

5-Methoxy-2,3,4,4a,10,10a-hexahydro-1H-phenanthren-9-one

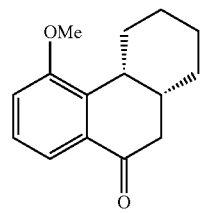

Combine [2-(2-methoxy-phenyl)-cyclohexyl]-acetic acid (0.300 g, 1.21 mmol), oxalyl chloride (0.13 mL, 1.45 mmol), and dichloromethane (6.0 mL) and catalytic DMF (0.1 mL) at room temperature. After 1 hour at 0° C. added TiCl$_4$ (0.33 mL, 3.0 mmol) and reaction gradually warmed to room temperature. After 3 hours, quenched reaction with 5N HCl and added ethyl acetate. Separate layers, wash with brine, and dry over anhydrous sodium sulfate. Concentrate and flash chromatograph using 0 to 20% ethyl acetate/hexanes eluent to yield the titled compound (0.198 g, 72%). TLC Rf=0.4 in 20% ethyl acetate/hexanes. $^1$H NMR (CDCl$_3$): 7.6 (d, 1H, J=7.0 Hz), 7.3 (m, 1H), 7.0 (m, 1H), 3.8 (s, 3H), 3.2 (m, 1H), 2.9 (m, 1H), 2.4 (m, 2H), 1.9 (m, 1H), 1.6 (m, 7H).

PREPARATION 50

5-Methoxy-10-(4-methoxy-phenyl)-2,3,4,4a,10,10a-hexahydro-1H-phenanthren-9-one

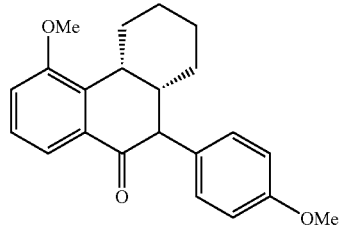

Preparation 50 is prepared from preparation 49 in a manner similar to preparation 6. TLC Rf=0.4 in 4:1 hexanes:ethyl acetate. $^1$H NMR (CDCl$_3$): 7.6 (d, 1H, J=7.0 Hz), 7.3 (m, 1H), 7.1 (m, 3H), 6.9 (m, 2H), 4.0 (d, 1H, J=13.0 Hz), 3.9 (s, 3H), 3.8 (s, 3H), 3.4 (m, 1H), 2.6 (m, 1H), 2.0 (m, 1H), 1.9 (m, 1H), 1.5 (m, 6H).

PREPARATION 51

5-Methoxy-10-(4-methoxy-phenyl)-1,2,3,4,4a,9,10,10a-octahydro-phenanthren-9-ol

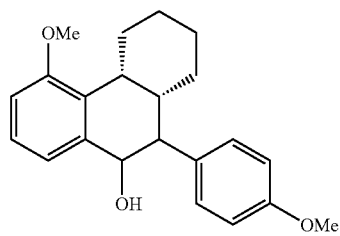

Preparation 51 is prepared from preparation 50 in a manner similar to preparation 7. TLC Rf=0.22 in 4:1 hexanes:ethyl acetate. ¹H NMR (CDCl₃): 7.2 (m, 4H), 6.9 (m, 2H), 6.8 (m, 1H), 4.8 (d, 1H, J=9.4 Hz), 3.8 (s, 6H), 3.2 (m, 2H), 2.2 (m, 1H), 2.0 (m, 1H), 1.9 (m, 1H), 1.5 (m, 6H).

PREPARATION 52

5-Methoxy-10-(4-methoxy-phenyl)-1,2,3,4,4a,10a-hexahydro-phenanthrene

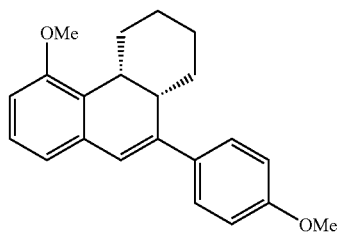

Preparation 52 is prepared from preparation 51 in a manner similar to preparation 8. TLC Rf=0.41 in 9:1 hexanes:ethyl acetate. ¹H NMR (CDCl₃): 7.3 (m, 2H), 7.2 (m, 1H), 6.9 (m, 2H), 6.7 (m, 2H), 6.4 (d, 1H, J=2.7 Hz), 3.9 (s, 3H), 3.8 (s, 3H), 3.3 (m, 1H), 3.2 (m, 1H), 2.1 (m, 1H), 1.4 (m, 7H).

PREPARATION 53

5-Methoxy-10-(4-methoxy-phenyl)-1,2,3,4,4a,9,10,10a-octahydro-phenanthrene

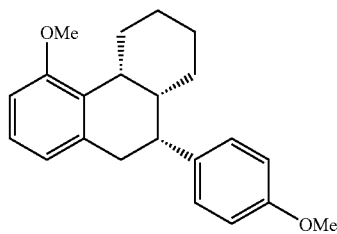

Preparation 53 is prepared from preparation 52 in a manner similar to preparation 9. TLC Rf=0.41 in 9:1 hexanes:ethyl acetate. ¹H NMR (CDCl₃): 7.2 (m, 3H), 6.8 (m, 4H), 3.8 (s, 6H), 3.3 (m, 2H), 3.1 (m, 1H), 2.9 (m, 2H), 2.1 (m, 1H), 1.4 (m, 7H).

PREPARATION 54

2-(4-Methoxyphenyl)-cyclohexanone

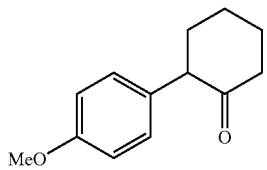

Combine 4-bromoanisole (19.6 g, 104 mmol), cyclohexanone (13.2 g, 136 mmol), sodium tert-butoxide (11.8 g, 120 mmol), palladium acetate (0.47 g, 2.1 mmol), (oxy-di-2,1-phenylene)bis-diphenylphosphine (2.28 g, 4.1 mmol) and toluene (240 mL) and heated at 90° C. under nitrogen. After 18 hours, cool to room temperature and add 1N HCl (120 mL). Extract with methylene chloride and wash the combined extracts with brine. Dry the organic layer over sodium sulfate and concentrate in vacuo. Purify by flash chromatography using silica gel and 10% ethyl acetate-hexanes to yield the titled compound (8.15 g, 38%) as a white solid. ¹H NMR (CDCl₃) δ 7.12 (d, 2H, J=7.5 Hz), 6.92 (d, 2H, J=7.5 Hz), 3.84 (s, 3 H), 3.59 (dd, 1H, J=8.0 and 3.5 Hz), 2.60-2.45 (m, 2H), 2.29 (m, 1H), 2.18 (m, 1H), 2.04 (m, 2H), 1.85 (m, 2H). MS m/z 205 (M+1).

PREPARATION 55

[2-(4-Methoxy-phenyl)-cyclohexylidene]-acetic acid ethyl ester

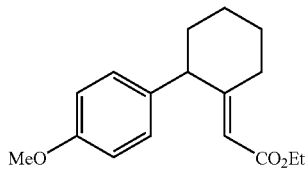

Preparation 55 is prepared from preparation 54 in a manner similar to preparation 1. ¹H NMR (CDCl₃) δ 7.15 (d, 2H, J=7.5 Hz), 6.92 (d, 2H, J=7.5 Hz), 5.15 (s, 1H), 4.11 (q, 2H, J=7.2 Hz), 3.83 (s, 3H), 3.75 (m, 1H), 3.39 (dd, 1H, J=8.0 and 3.5 Hz), 2.20 (m, 1H), 2.04 (m, 1H), 1.95-1.88 (m, 3H), 1.75-1.50 (m, 2H), 1.22 (t, 3H, J=7.2 Hz).

PREPARATION 56

[2-(4-Methoxy-phenyl)-cyclohex-1-enyl]-acetic acid ethyl ester

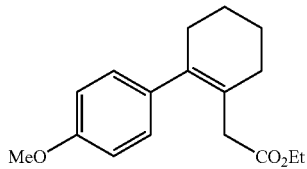

Preparation 56 is prepared from preparation 55 in a manner similar to preparation 2. ¹H NMR (CDCl₃) δ 7.15 (d, 2H, J=7.5 Hz), 6.87 (d, 2H, J=7.5 Hz), 4.16 (q, 2H, J=7.2 Hz), 3.83 (s, 3H), 2.95 (s, 2H), 2.30 (m, 2H), 2.16 (m, 2H), 1.80-1.70 (m, 4H), 1.25 (t, 3H, J=7.2 Hz).

PREPARATION 57

[2-(4-Methoxy-phenyl)-cyclohexyl]-acetic acid ethyl ester

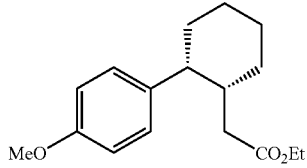

Preparation 57 is prepared from preparation 56 in a manner similar to preparation 3. $^1$H NMR (CDCl$_3$) δ 7.14 (d, 2H, J=7.5 Hz), 6.85 (d, 2H, J=7.5 Hz), 4.02 (q, 2H, J=7.2 Hz), 3.81 (s, 3H), 2.89 (m, 1H), 2.53 (m, 1H), 2.34 (dd, 1H, J=12.0 and 6.5 Hz), 1.98 (dd, 1H, J=12.0 and 2.0 Hz), 1.90 (m, 1H), 1.80-1.65 (m, 4H), 1.60-1.38 (m, 3H), 1.21 (t, 3H, J=7.2 Hz).

PREPARATION 58

[2-(4-Methoxy-phenyl)-cyclohexyl]-acetic acid

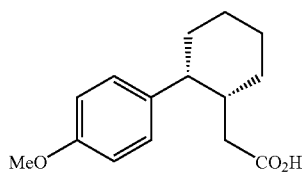

Preparation 58 is prepared from preparation 57 in a manner similar to preparation 4. $^1$H NMR (CDCl$_3$) δ 7.12 (d, 2H, J=7.5 Hz), 6.86 (d, 2H, J=7.5 Hz), 3.81 (s, 3H), 2.91 (m, 1H), 2.48 (m, 1H), 2.36 (dd, 1H, J=12.0 and 6.5 Hz), 2.01 (dd, 1H, J=12.0 and 2.0 Hz), 1.90-1.40 (m, 8H).

PREPARATION 59

7-Methoxy-2,3,4,4a,10,10a-hexahydro-1H-phenanthren-9-one

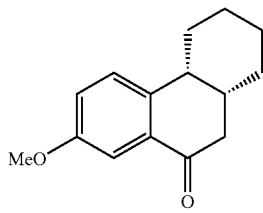

Preparation 59 is prepared from preparation 58 in a manner similar to preparation 5. $^1$H NMR (CDCl$_3$): 7.54 (d, 1H, J=1.5 Hz), 7.22 (d, 1H, J=8.0 Hz), 7.13 (dd, 1H, J=8.0 and 1.5 Hz), 3.85 (s, 3H), 2.95-2.82 (m, 2H), 2.58-2.45 (m, 2H), 1.80-1.25 (m, 8H).

PREPARATION 60

7-Methoxy-10-(4-methoxy-phenyl)-2,3,4,4a,10,10a-hexahydro-1H-phenanthren-9-one

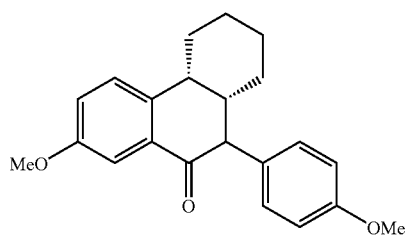

Preparation 60 is prepared from preparation 59 in a manner similar to preparation 6. $^1$H NMR (CDCl$_3$): 7.57 (d, 1H, J=1.5 Hz), 7.22 (d, 1H, J=8.0 Hz), 7.15 (dd, 1H, J=8.0 and 1.5 Hz), 7.09 (d, 2H, J=7.5 Hz), 6.93 (d, 2H, J=7.5 Hz), 3.95 (d, 1H, J=9.5 Hz), 3.88 (s, 3H), 3.82 (s, 3H), 3.04 (m, 1H), 2.68 (m, 1H), 1.81 (m, 3H), 1.55-1.42 (m, 5H).

PREPARATION 61

7-Methoxy-10-(4-methoxy-phenyl)-1,2,3,4,4a,9,10,10a-octahydro-phenanthren-9-ol

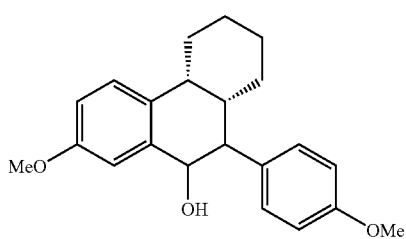

Preparation 61 is prepared from preparation 60 in a manner similar to preparation 7. $^1$H NMR (CDCl$_3$): 7.24 (d, 2H, J=7.5 Hz), 7.18 (d, 1H, J=1.5 Hz), 7.10 (d, 1H, J=8.0 Hz), 6.95 (d, 2H, J=7.5 Hz), 6.84 (dd, 1H, J=8.0 and 1.5 Hz), 4.81 (d, 1H, J=9.5 Hz), 3.85 (s, 3H), 3.82 (s, 3H), 3.12 (m, 1H), 2.87 (m, 1H), 2.39 (m, 1H), 1.95-1.75 (m, 2H), 1.67 (m, 1H), 1.50-1.22 (m, 5H).

PREPARATION 62

7-Methoxy-10-(4-methoxy-phenyl)-1,2,3,4,4a,10a-hexahydro-phenanthrene

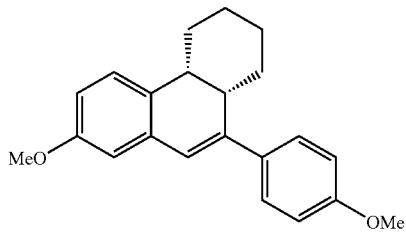

Preparation 62 is prepared from preparation 61 in a manner similar to preparation 8. $^1$H NMR (CDCl$_3$): 7.58 (d, 2H, J=7.5 Hz), 7.25 (d, 1H, J=8.0 Hz), 6.96 (d, 2H, J=7.5 Hz), 6.80 (dd, 1H, J=8.0 and 1.0 Hz), 6.76 (d, 1H, J=1.0 Hz), 6.71 (s, 1H), 3.86 (s, 3H), 3.82 (s, 3H), 3.20 (m, 1H), 2.81 (m, 1H), 2.52 (m, 1H), 1.97 (m, 1H), 1.70 (m, 2H), 1.70-1.50 (m, 4 H).

PREPARATION 63

7-Methoxy-10-(4-methoxy-phenyl)-1,2,3,4,4a,9,10,10a-octahydro-phenanthrene

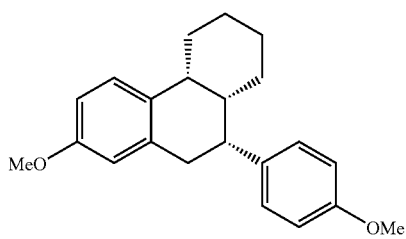

Preparation 63 is prepared from preparation 62 in a manner similar to preparation 9. $^1$H NMR (CDCl$_3$): 7.35 (d, 1H, J=7.5 Hz), 7.28 (d, 2H, J=7.5 Hz), 6.92 (d, 2H, J=7.5 Hz), 8.82 (dd, 1H, J=7.5 and 1.0 Hz), 6.76 (d, 1H, J=1.0 Hz), 3.85 (s, 3H), 3.83 (s, 3H), 3.35-3.18 (m, 3H), 2.91 (dd, 1H), 2.50 (m, 1H), 2.05 (m, 1H), 1.80-1.40 (m, 4H), 1.30 (m, 1H), 1.18 (m, 2H).

PREPARATION 64

2-(3-Methoxy-phenyl)-4,4-dimethyl-cyclohex-2-enone

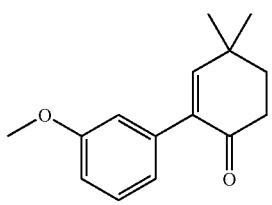

Dissolve 2-iodo-4,4-dimethyl-cyclohex-2-enone(Tetrahedron Letters (1994), 35(37), 6787-90) (11 g, 44 mmol) in tetrahydrofuran (200 ml). Add 3-methoxyphenyl boronic acid (10 g, 65.8 mmol), triphenyl arsine (808 mg, 2.64 mmol), silver oxide (15.3 g, 66 mmol) in water (25 ml), bis(benzonitrile)dichloropalladium(II) (506 mg, 1.32 mmol). Stir at room temperature for 1 h. Quench with saturated aqueous ammonium chloride (200 ml), and stir 1 h. Filter reaction mixture through a bed of celite rinsing celite with ether (200 ml). Separate filtrate layers and extract the aqueous layer with additional ether (200 ml), combine organic extracts, and wash with water 2×(200 ml), brine (100 ml), dry, and concentrate. Chromatograph residue on a Biotage eluting with 10% ethyl acetate in hexanes to give (10.1 g, 99%) of the title compound as a yellow oil: $^1$H NMR (CDCl$_3$) δ 7.26-7.23 (m, 1H), 6.88-6.84 (m, 3H), 6.69 (s, 1H), 3.81 (s, 3H), 2.62 (t, 2H), 1.96 (t, 2H), 1.25 (s, 6H).

PREPARATION 65

2-(3-Methoxy-phenyl)-4,4-dimethyl-cyclohexanone

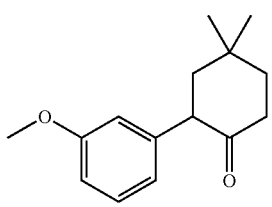

Dissolve 2-(3-methoxy-phenyl)-4,4-dimethyl-cyclohex-2-enone (13 g, 56.4 mmol) in ethanol (500 ml), exchange with N$_2$ 3×, and add 10% palladium on activated carbon (0.3 g, 2.82 mmol). Stir under atmospheric pressure of H$_2$ over night. Filter off catalyst and concentrate to give the title compound (13.1 g, 99%): $^1$H NMR (CDCl$_3$) δ 7.24-7.19 (m, 1H), 6.85-6.64 (m, 3H), 3.78 (s, 3H), 1.97-1.89 (m, 1H), 1.82-1.75 (m, 3H), 1.64-1.55 (m, 1H), 1.25-1.14 (m, 2H), 1.0 (s, 3H), 0.96 (s,3H).

PREPARATION 66

[2-(3-Methoxy-phenyl)-4,4-dimethyl-cyclohexylidene]-acetic acid methyl ester

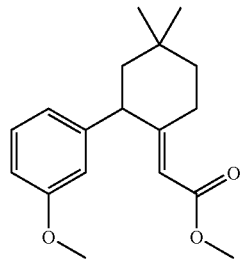

Dissolve 2-(3-methoxy-phenyl)-4,4-dimethyl-cyclohexanone (13.1 g, 56.4 mmol) in toluene (135 ml), add (triphenyl-λ5-phosphanylidene)-acetic acid methyl ester (28.3 g, 84.6 mmol). Heat reaction mixture at reflux stirring over night. Dilute with ether, filter and concentrate. Chromatograph on a biotage eluting with 10% ethyl acetate in hexanes to give the title compound (5.3 g 33%): $^1$H NMR (CDCl$_3$) δ 7.27-7.23 (m, 1H), 6.88-6.77 (m, 3H),5.01 (s, 1H), 3.77 (s, 3H), 3.56 (s, 3H), 3.53-3.48 (m, 1H), 2.19-2.10 (m, 1H), 1.78-1.58 (m, 3H), 1.46-1.38 (m, 1H), 1.25-1.20 (m, 1H), 1.11 (s, 3H), 0.96 (s, 3H).

PREPARATION 67

[2-(3-Methoxy-phenyl)-4,4-dimethyl-cyclohex-1-enyl]-acetic acid methyl ester

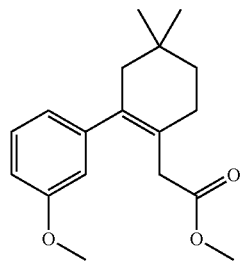

Dissolve sodium methoxide (0.99 g, 18.4 mmol) in DMSO (37 ml) add methyl acetate (1 ml), add [2-(3-methoxy-phenyl)-4,4-dimethyl-cyclohexylidene]-acetic acid methyl ester (5.3 g, 18 mmol). Heat at 100° C. stirring over night. Dilute with ethyl acetate (50 ml), wash with brine 4× (30 ml), dry, and concentrate to give the title compound (5.2 g 98%): $^1$H NMR (CDCl$_3$) δ 7.24-7.18 (m, 1H), 6.78-6.68 (m, 3H), 3.79 (s, 3H), 3.65 (s, 2H), 3.59 (s,1H), 2.95 (s,1H), 2.15-2.07 (m, 3H), 1.55(s, 3H), 1.49-1.46 (m,1H), 0.98 (s, 6H).

PREPARATION 68

[2-(3-Methoxy-phenyl)-4,4-dimethyl-cyclohexyl]-acetic acid methyl ester

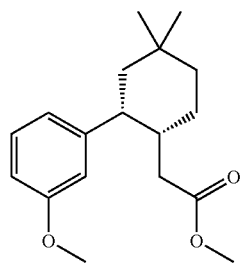

Dissolve [2-(3-methoxy-phenyl)-4,4-dimethyl-cyclohex-1-enyl]-acetic acid methyl ester (4.3 g, 15 mmol) in methanol (135 ml), exchange with N₂ 3×, add palladium hydroxide 20% on activated carbon (0.84 g, 5.9 mmol). Add 60 psi of H₂ at room temperature for 18 h. Filter off catalyst rinsing with methanol, concentrate filtrate to give the title compound (3.8 g, 88%): $^1$H NMR (CDCl₃) δ 7.23-7.17 (m, 1H), 6.79-6.71 (m, 3H), 3.80 (s, 3H), 3.55-3.49 (t, 3H), 2.52-2.19 (m, 1H), 1.95-1.83 (m, 2H), 1.72-1.21 (m, 6H), 1.02 (s,3H), 0.99, (s, 3H), 0.93 (s, 1H).

PREPARATION 69

[2-(3-Methoxy-phenyl)-4,4-dimethyl-cyclohexyl]-acetic acid

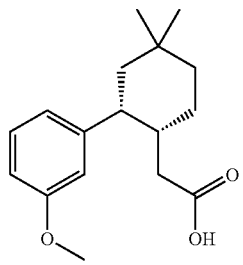

Preparation 69 is prepared from preparation 68 in a manner similar to preparation 4. (3.3 g, 91%): $^1$H NMR (CDCl₃) δ 7.22-7.17 (m, 1H), 6.79-6.71 (m, 3H), 3.79 (s, 3H), 2.50-2.22 (m, 1H), 1.95-1.77 (m, 2H), 1.67-1.21 (m, 6H), 1.02 (s, 3H), 0.99 (s, 3H), 0.93 (s, 1H).

PREPARATION 70

6-Methoxy-3,3-dimethyl-2,3,4,4a,10,10a-hexahydro-1H-phenanthren-9-one

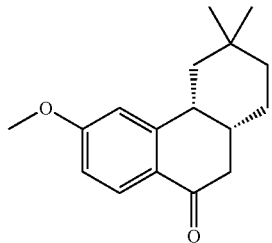

Preparation 70 is prepared from preparation 69 in a manner similar to preparation 5. (1.3 g, 41%): $^1$H NMR (CDCl₃) δ 8.01-7.99 (d, 1H), 6.83-6.78 (dd, 1H), 6.66-6.65 (d, 1H), 3.86 (s, 3H), 3.03-2.98 (m, 1H), 2.89-2.82 (m, 1H), 2.52-2.49 (m, 1H), 2.32-2.26 (m, 1H), 1.94-1.87 (m, 1H), 1.53-1.37 (m, 4H), 1.30-1.24 (m, 1H), 1.09 (s, 3H), 0.94 (s, 3H).

PREPARATION 71

6-Methoxy-10-(4-methoxy-phenyl)-3,3-dimethyl-2,3,4,4a,10,10a-hexahydro-1H-phenanthren-9-one

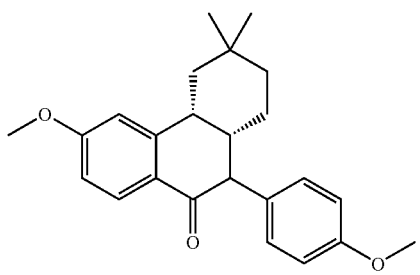

Using a 2 neck v shaped flask, combine 6-Methoxy-3,3-dimethyl-2,3,4,4a,10,10a-hexahydro-1H-phenanthren-9-one (1.3 g, 4.9 mmol), and 4 bromoanisole (0.16 ml, 4.9 mmol) in dioxane (40 ml) exchange with N₂ add sodium t-butoxide, Add Pd[P(C₄H₉)₃]₂ exchange with N₂. Heat at 80° stirring over night. Keeping reaction under N₂ quench with acetic acid (6 ml). Dilute with ethyl acetate (50 ml), wash with saturated aqueous sodium bicarbonate 3× (50 ml), with brine (40 ml), dry, and concentrate. Chromatograph residue on an biotage eluting with 0-10% ethyl acetate in hexanes to give the title compound (1.6 g, 90%): $^1$H NMR (CDCl₃) δ 8.02-7.99 (d, 1H), 7.07-7.05 (d, 2H), 6.9-6.88 (d, 2H), 6.85-6.82 (dd, 1H), 6.69-6.68 (d, 1H), 3.88 (s, 3H), 3.81 (s, 3H), 3.17-3.12 (m, 1H), 2.68-2.62 (m, 1H), 1.68-1.60 (m, 1H), 1.52-1.44 (m, 3H), 1.41-1.37 (m, 1H), 1.30-1.24 (m, 1H), 1.18-1.13 (m, 1H), 1.1 (s, 3H), 0.99 (s, 3H).

PREPARATION 72

6-Methoxy-10-(4-methoxy-phenyl)-3,3-dimethyl-1,2,3,4,4a,9,10,10a-octahydro-phenanthren-9-ol

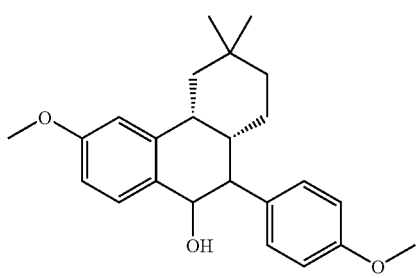

Preparation 72 is prepared from preparation 71 in a manner similar to preparation 7. (0.8 g, 72%): $^1$H NMR (CDCl₃) δ 7.51-7.49 (d, 1H), 7.12-7.19 (d, 2H), 6.94-6.91 (d, 2H), 6.81-6.78 (dd, 1H), 3.83 (s, 3H), 3.81 (s,3H), 3.07-2.98 (m, 1H), 1.65-1.49 (m, 7H), 1.43-1.18 (m, 3H), 1.03 (s, 3H), 0.93 (s, 3H).

PREPARATION 73

6-Methoxy-10-(4-methoxy-phenyl)-3,3-dimethyl-1,2,3,4,4a,10a-hexahydro-phenanthrene

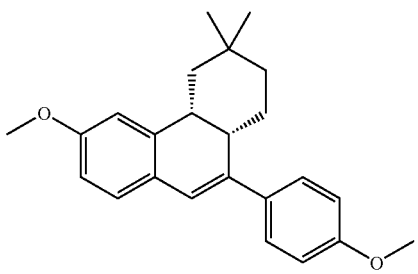

Preparation 73 is prepared from preparation 72 in a manner similar to preparation 8. (0.7 g, 92%)%): $^1$H NMR (CDCl$_3$) δ 7.33-7.31 (d, 2H), 7.02-6.99 (d, 1H), 6.90-6.88 (d, 2H), 6.79 (m, 1H), 6.70-6.67 (dd, 1H), 6.47 (bs, 1H), 3.83 (s, 3H), 3.82 (s, 3H), 3.09-2.99 (m, 1H), 1.45-1.25 (m, 3H), 1.06-1.03 (m, 2H), 1.0 (s, 3H), 0.95-0.89 (m, 2H), 082 (s 3H).

PREPARATION 74

6-Methoxy-10-(4-methoxy-phenyl)-3,3-dimethyl-1,2,3,4,4a,9,10,10a-octahydro-phenanthrene

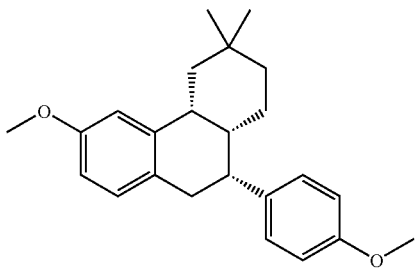

Preparation 74 is prepared from preparation 73 in a manner similar to preparation 9. (0.38 g, 54%): $^1$H NMR (CDCl$_3$) δ 7.24-7.22 (d,2H), 7.11-7.05 (m, 1H), 6.98-6.97 (m, 1H), 6.90-6.88 (d, 2H), 6.72-6.69 (dd, 1H), 3.82 (s,3H), 3.81 (s, 3H), 3.3-3.26 (m, 1H), 2.81-2.75 (m, 1H), 1.43-1.17 (m, 6), 1.11-0.99 (m, 3H), 0.88 (s, 3H), 0.49 (s, 3H).

PREPARATION 75

5,5-Dimethyl-cyclohex-2-enone

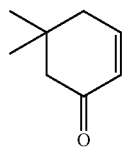

Dissolve 3-methoxy-5,5-dimethyl-cyclohex-2-enone (Tetrahedron 57 (2001) 217-225) (10.6 g, 68.7 mmol) in ether (500 ml) cool to 0° C., add dropwise a 1.5M solution of diisobutyl aluminum hydride (68.7 ml, 103 mmol), and stir for 30 minutes. Add saturated aqueous ammonium chloride (25 ml), stir 1 hour, add anhydrous magnesium sulfate (10 g), stir 1 hour. Filter through celite and concentrate. Dissolve the residue in ether (500 ml), add toluene-4-sulfonic acid monohydrate (650 mg, 3.44 mmol) and water (6.2 ml), and stir 1 hour. Wash with saturated aqueous sodium bicarbonate, brine, dry and concentrate to give the title compound as a clear oil (5.0 g, 58%): $^1$H NMR (CDCl$_3$) δ 6.89-6.84 (m, 1H), 2.28 (s, 2H), 2.26-2.24 (q, 2H), 1.06 (s, 6H).

PREPARATION 76

2-(3-Methoxy-phenyl)-5,5-dimethyl-cyclohex-2-enone

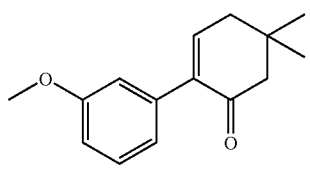

Preparation 76 is prepared from preparation 75 in a manner similar to preparation 64. (6.6 g, 43 mmol) to give the title compound (5.8 g, 87%): $^1$H NMR (CDCl$_3$) δ 7.27-7.24 (m, 1H), 6.92-6.84 (m, 4H), 3.81 (s,3H), 2.45 (s, 2H), 2.43-2.42 (d, 2H), 1.11 (s, 6H).

PREPARATION 77

2-(3-Methoxy-phenyl)-5,5-dimethyl-cyclohexanone

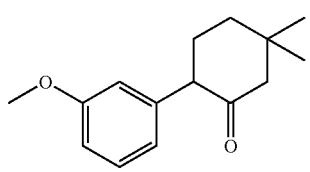

Preparation 77 is prepared from preparation 76 in a manner similar to preparation 65. (5.8 g, 99%): $^1$H NMR (CDCl$_3$) δ 7.27-7.24 (m, 1H), 6.82-6.79 (dd, 1H), 6.75-6.73 (d, 1H), 6.70-6.69 (m, 1H), 3.79 (s, 3H),3.53-3.48 (m, 1H), 2.37-2.24 (m, 2H), 2.19-2.13 (m, 2H), 1.83-1.69 (m, 2H), 1.11 (s, 3H), 1.00 (s, 3H).

PREPARATION 78

[2-(3-Methoxy-phenyl)-5,5-dimethyl-cyclohexylidene]-acetic acid methyl ester

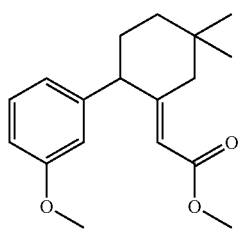

Preparation 78 is prepared from preparation 77 in a manner similar to preparation 66. (5.3 g, 74%): ¹H NMR (CDCl₃) δ 7.24-7.20 (m, 1H), 6.77-6.69 (m, 3H), 5.19 (s, 1H), 3.77 (s, 3H), 3.58 (s, 3H), 3.47-3.43 (d, 1H), 3.28-3.24 (dd, 1H), 2.06-2.01 (m, 2H), 1.94-1.87(m, 1H), 1.56-1.51(m, 2H), 1.03 (s, 3H), 0.91 (s, 3H).

PREPARATION 79

[2-(3-Methoxy-phenyl)-5,5-dimethyl-cyclohex-1-enyl]-acetic acid methyl ester

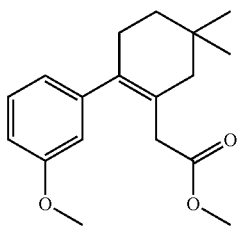

Preparation 79 is prepared from preparation 78 in a manner similar to preparation 67. (4.8 g, 100%): ¹H NMR (CDCl₃) δ 7.20-7.17 (m, 1H), 6.76-6.68 (m, 3H), 3.76 (s, 3H), 3.61 (s, 3H), 2.89 (s, 2H), 2.29-2.26 (t, 2H), 1.86 (s, 2H), 1.46-1.43(t, 2H), 0.95 (s, 6H).

PREPARATION 80

[2-(3-Methoxy-phenyl)-5,5-dimethyl-cyclohexyl]-acetic acid methyl ester

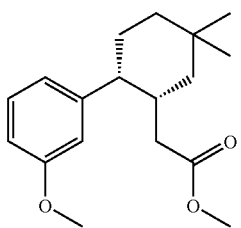

Preparation 80 is prepared from preparation 79 in a manner similar to preparation 3. (2 g, 99%): ¹H NMR (CDCl₃) δ 7.21-7.17 (t, 1H), 6.83-6.81 (d, 1H), 6.79-6.79 (t, 1H), 6.75-6.73 (dd, 1H), 2.96-2.92 (m, 1H), 2.56-2.48 (m, 1H), 2.09-2.07 (d, 2H), 1.92-173 (m, 2H), 1.66-1.52 (m, 3H), 1.43-1.39 (m, 1H), 1.33-1.26 (m, 1H), 1.02 (s, 3H), 1.0 (s, 3H).

PREPARATION 81

[2-(3-Methoxy-phenyl)-5,5-dimethyl-cyclohexyl]-acetic acid

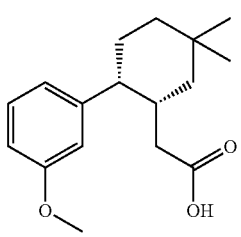

Preparation 81 is prepared from preparation 80 in a manner similar to preparation 4. (0.95 g, 99%): ¹H NMR (CDCl₃) δ 7.21-7.17 (t, 1H), 6.84-6.82 (d, 1H), 6.79-6.78 (t, 1H), 676-6.73 (dd, 1H), 3.79 (s, 3H), 2.98-2.93 (q, 1H), 2.55-2.46 (m, 1H), 2.13-2.09 (dd, 2H), 1.93-1.73 (m, 2H), 1.66-1.55 (m, 2H), 1.46-1.41 (m, 1H), 1.33-1.27 (m, 1H), 1.04 (s, 3H), 1.00 (s, 3H).

PREPARATION 82

6-Methoxy-2,2-dimethyl-2,3,4,4a,10,10a-hexahydro-1H-phenanthren-9-one

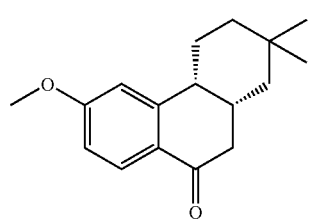

Preparation 82 is prepared from preparation 81 in a manner similar to preparation 5. (0.72 g, 81%): ¹H NMR (CDCl₃) δ 8.06-8.04 (d, 1H), 6.87 (s, 1H), 6.84-6.81 (dd, 1H), 3.87 (s, 3H), 3.21-3.17 (m, 1H), 2.77-2.72 (m, 1H), 2.55-2.47 (m, 2H), 2.28-2.22 (m, 1H), 1.98-1.88 (m, 1H), 1.21-1.13 (m, 4H), 0.98 (s, 3H), 0.79 (s, 3H).

PREPARATION 83

6-Methoxy-10-(4-methoxy-phenyl)-2,2-dimethyl-2,3,4,4a,10,10a-hexahydro-1H-phenanthren-9-one

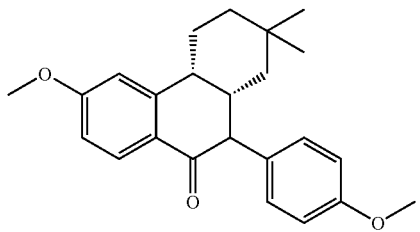

Preparation 83 is prepared from preparation 82 in a manner similar to preparation 6. (0.43 g 49%): ¹H NMR (CDCl₃) δ 8.16-8.14 (d, 1H), 7.01-6.99 (d, 2H), 6.89-6.86 (m, 2H), 6.80-6.78 (d, 2H), 3.89 (s, 3H), 3.75 (s, 3H), 3.61-3.60 (m, 1H), 3.13-3.11 (m, 1H), 2.56-2.51 (m, 1H), 2.23-2.18 (m, 1H), 1.84-1.77 (m, 1H), 1.49-1.46 (d, 2H), 1.33-1.21 (m, 2H), 0.98 (s, 3H), 0.82 (s, 3H).

PREPARATION 84

6-Methoxy-10-(4-methoxy-phenyl)-2,2-dimethyl-1,2,3,4,4a,9,10,10a-octahydro-phenanthren-9-ol

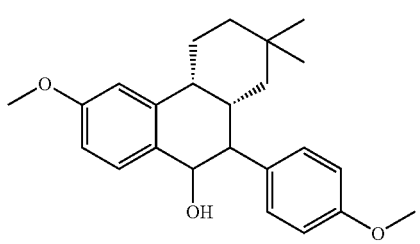

Preparation 84 is prepared from preparation 83 in a manner similar to preparation 7. (0.34 g, 55%): ¹H NMR (CDCl₃) δ 7.51-7.49 (d, 1H), 7.19-7.17 (d, 2H), 6.93-6.88 (m, 3H), 6.83-6.78 (m, 2H), 4.63-4.59 (m, 1H), 3.83 (s, 3H), 3.82 (s, 3H), 2.90-2.85 (m, 1H), 2.78-2.73 (m, 1H), 2.43-2.40 (m,1H), 2.04-1.96 (m, 1H), 1.52-1.45 (m, 2H), 1.38-1.34 (m, 2H), 1.26-1.24 (m, 2H), 0.82 (s, 3H), 0.79 (s,3H).

PREPARATION 85

6-Methoxy-10-(4-methoxy-phenyl)-2,2-dimethyl-1,2,3,4,4a,10a-hexahydro-phenanthrene

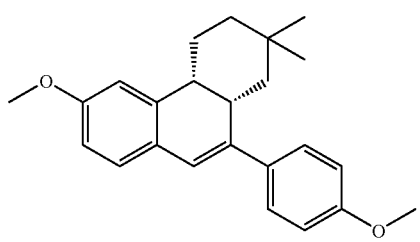

Preparation 85 is prepared from preparation 84 in a manner similar to preparation 8. (0.3 g 93%): ¹H NMR (CDCl₃) δ 7.49-7.46 (d, 2H), 7.05-7.03 (d, 1H), 6.89-6.86 (m, 3H) 6.69-6.66 (m, 2H), 3.80 (s, 3H), 3.79 (s, 3H), 3.15-3.12 (m, 1H), 2.98-2.92 (m, 1H), 2.33-2.28 (m, 1H), 2.0-1.92 (m, 1h), 1.47-1.39 (m, 2H), 1.23-1.12 (M, 2H), 1.04 (s, 3H), 0.74 (s, 3H).

PREPARATION 86

6-Methoxy-10-(4-methoxy-phenyl)-2,2-dimethyl-1,2,3,4,4a,9,10,10a-octahydro-phenanthrene

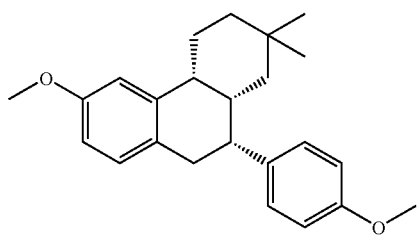

Preparation 86 is prepared from preparation 85 in a manner similar to preparation 9. (0.3 g, 99%): ¹H NMR (CDCl₃) δ 7.17-7.15 (d, 2H), 7.03-7.01 (d, 1H), 6.88-6.87 (m, 1H), 6.83-6.81 (d, 2H), 6.80-6.65 (dd, 1H), 3.75 (s, 3H), 3.74 (s, 3H), 3.10-3.08 (m, 3H), 2.83-2.76 (m, 1H), 2.24-2.16 (m, 2H), 1.91-1.83 (m, 1H), 1.04-1.0 (m, 2H), 0.94-0.80 (m, 2H), 0.76 (s, 3H), 0.66 (s, 3H).

PREPARATION 87

2-(2,5-Dimethoxy-phenyl)-cyclopentanecarboxylic acid ethyl ester

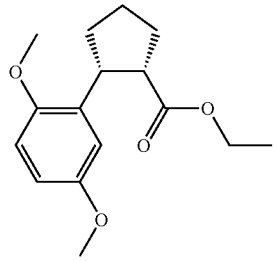

Dissolve 2-(2,5-dimethoxy-phenyl)-cyclopent-1-enecarboxylic acid ethyl ester (5 g, 18 mmol) in methanol (150 ml) exchange with N2 3×, add platinum oxide (1.6 g 7.2 mmol), add 60 psi of H₂ for 24 hours at room temperature. Filter off catalyst, concentrate the filtrate to give the title compound (4.5 g, 89%): ¹H NMR (CDCl₃) δ 6.77-6.67 (m, 3H), 3.81 (s, 3H), 3.74 (s, 3H), 3.71-3.57 (m, 3H), 3.32-3.27 (m, 1H), 2.13-1.96 (m, 4H), 1.89-1.83 (m, 1H), 1.70-1.62 (m, 1H), 0.83-0.79 (t, 3H).

PREPARATION 88

[2-(2,5-Dimethoxy-phenyl)-cyclopentyl]-methanol

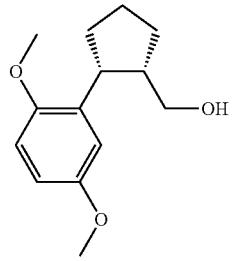

Dissolve 2-(2,5-dimethoxy-phenyl)-cyclopentanecarboxylic acid ethyl ester (4.5 g, 16 mmol) in tetrahydrofuran (80 ml), add a 1.0M solution of lithium aluminum hydride in tetrahydrofuran (49 ml, 49 mmol), and stir at room temperature for 1 hour. Pour slowly into a mixture of ether and aqueous Rochelle's Salt, stir over night, separate layers, wash organic with brine, dry and concentrate to give the title compound (3.6 g, 94%): ¹H NMR (CDCl₃) δ 6.82-6.70 (m, 3H), 3.82 (s, 3H), 3.77 (s, 3H), 3.66-3.60 (m, 1H), 3.30-3.23 (m, 1H), 3.07-3.01 (m, 1H), 2.53-2.43 (m, 1H), 2.14-2.11 (m, 1H), 2.03-1.98 (m, 1H), 1.94-1.89 (m, 2H), 1.81-1.71 (m, 2H), 1.43-1.38 (m, 1H).

PREPARATION 89

Methanesulfonic acid 2-(2,5-dimethoxy-phenyl)-cyclopentylmethyl ester

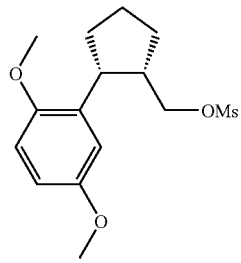

Dissolve [2-(2,5-dimethoxy-phenyl)-cyclopentyl]-methanol (3.6 g, 15 mmol) in dichloromethane (94 ml), add 2,6-dimethylaminopyridine (0.4 g, 0.31 mmol), add triethylamine (4.7 ml, 33.5 mmol), cool to 0° C., add methanesulfonyl chloride (1.9 g, 17 mmol), remove ice bath and stir 2 hours at room temperature. Quench with water and ethyl acetate, separate layers, wash with brine, dry and concentrate to give the title compound (4.8 g, 100%): $^1$H NMR (CDCl$_3$) δ 6.78-6.69 (m, 3H), 3.86-3.82 (m, 1H), 3.79 (s, 3H), 3.76 (s, 3H), 3.68-3.64 (m,1H), 3.53-3.47 (m, 1H), 2.83-2.76 (m, 1H), 2.69 (s,3H), 1.97-1.88 (m, 3H), 1.67-1.60 (m,3H).

PREPARATION 90

[2-(2,5-Dimethoxy-phenyl)-cyclopentyl]-acetonitrile

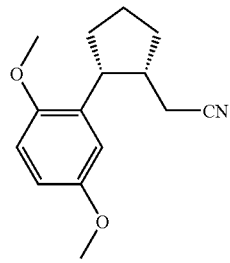

Dissolve methanesulfonic acid 2-(2,5-dimethoxy-phenyl)-cyclopentylmethyl ester (4.8 g, 15 mmol) in DMSO (25 ml), add sodium cyanide (12 g, 16 mmol), and heat at 100° C. overnight. Cool to room temperature and quench with water and ethyl acetate. Separate layers, wash organic with water 3×, brine 2×, dry and concentrate to give the title compound (3.4 g 91%): $^1$H NMR (CDCl$_3$) δ 6.79-6.72 (m,3H), 3.79 (s, 3H), 3.77 (s, 3H), 3.54-3.48 (m, 1H), 2.77-2.70 (m, 1H), 2.17-2.09 (m, 1H), 1.96-1.89 (m, 4H), 1.78-1.59 (m, 3H).

PREPARATION 91

[2-(2,5-Dimethoxy-phenyl)-cyclopentyl]-acetaldehyde

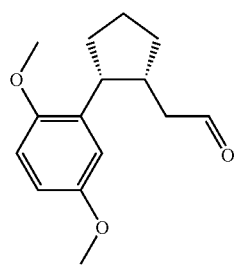

Dissolve [2-(2,5-dimethoxy-phenyl)-cyclopentyl]-acetonitrile (3.9 g, 16 mmol) in ether (85 ml), cool to −10° C., add diisobutylaluminum hydride 1.5M in toluene (19 ml, 29 mmol), and stir at −10° C. for 1 hour. Quench with 1N hydrochloric acid, and add ethyl acetate. Separate layers, wash organic with brine, dry, and concentrate to give the title compound (3 g, 76%): $^1$H NMR (CDCl$_3$) δ 9.50-9.49 (m, 1H), 6.77-6.69 (m, 3H), 3.77 (s, 3H), 3.76 (s, 3H), 3.58-3.54 (m, 1H), 2.88-2.83 (m, 1H), 2.08-1.87 (m, 5H), 1.74-1.65 (m, 2H), 1.44-1.39 (m, 1H).

PREPARATION 92

[2-(2,5-Dimethoxy-phenyl)-cyclopentyl]-acetic acid

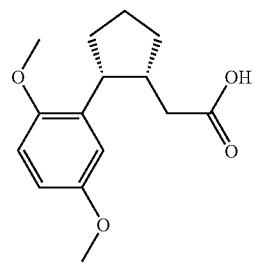

Prepare according to: Organic letters (2003) Vol. 5, No. 7 1031-1034 using [2-(2,5-Dimethoxy-phenyl)-cyclopentyl]-acetaldehyde (1 g, 4 mmol) and Oxone (2.5 g, 4 mmol) to give the title compound (1 g, 94%): $^1$H NMR (CDCl$_3$) δ 6.77-6.67 (m, 3H), 3.76 (s, 3H), 3.75 (s, 3H), 3.59-3.53 (m, 1H), 2.79-2.73 (m, 1H), 2.0-1.81 (m, 5H), 1.73-1.66 (m, 2H), 1.50-1.43 (m, 1H).

PREPARATION 93

6,9-Dimethoxy-1,2,3,3a,4,9b-hexahydro-cyclopenta[a]naphthalen-5-one

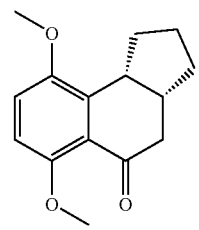

Preparation 93 is prepared from preparation 92 in a manner similar to preparation 5. (0.9 g, 97%): $^1$H NMR (CDCl$_3$) δ 6.99-6.96 (d, 1H), 6.78-6.76 (d, 1H), 3.84 (s, 3H), 3.82 (s, 3H), 3.41-3.35 (q, 1H), 2.73-2.65 (m, 1H), 2.6-2.46 (m, 2H), 2.44-2.36 (m, 1H), 1.97-1.88 (m, 1H), 1.85-1.69 (m, 2H), 1.55-1.47 (m, 1H).

PREPARATION 94

6,9-Dimethoxy-4-(4-methoxy-phenyl)-1,2,3,3a,4,9b-hexahydro-cyclopenta[a]naphthalen-5-one

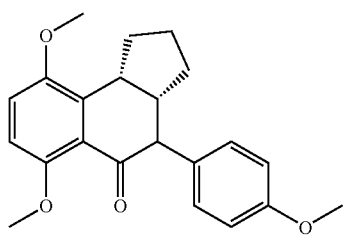

Preparation 94 is prepared from preparation 93 in a manner similar to preparation 71. (0.79 g, 61%): $^1$H NMR (CDCl$_3$) δ 7.08-7.06 (d, 6.97-6.95 (d, 1H), 6.87-6.85 (d, 2H), 6.77-6.75 (d, 1H), 3.83 (s, 3H), 3.79 (s, 1H), 3.72-3.69 (d, 1H), 3.54-3.48 (q, 1H), 2.93-2.86 (m, 1H), 2.56-2.47 ((m, 1H), 1.85-1.58 (m, 4H), 1.5-1.4 (m, 1H).

PREPARATION 95

6,9-Dimethoxy-4-(4-methoxy-phenyl)-2,3,3a,4,5,9b-hexahydro-1H-cyclopenta[a]naphthalen-5-ol

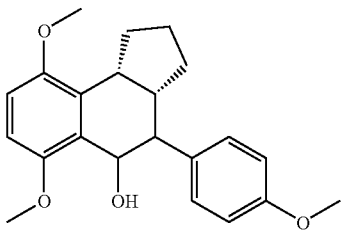

Preparation 95 is prepared from preparation 94 in a manner similar to preparation 7. (0.57 g, 72%): $^1$H NMR (CDCl$_3$) δ 7.30-7.23 (m, 2H), 6.92-6.89 (m, 2H), 6.78-6.68 (m, 2H), 4.97-4.95 (m, 1H), 4.03-3.98 (m, 1H), 3.82 (s, 3H), 3.81 (s, 3H), 3.78 (s, 3H), 3.34-3.28 (m, 1H), 3.0-2.93 (m, 1H), 2.78-2.66 (m, 1H), 2.50-2.38 (m, 2H), 1.83-1.76 (m, 1H), 1.68-1.62 (m, 2H), 1.43-1.36 (m, 1H).

PREPARATION 96

6,9-Dimethoxy-4-(4-methoxy-phenyl)-2,3,3a,9b-tetrahydro-1H-cyclopenta[a]naphthalene

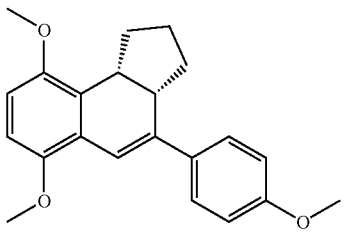

Preparation 96 is prepared from preparation 95 in a manner similar to preparation 8. (0.20 g, 37%): $^1$H NMR (CDCl$_3$) δ 7.41-7.39 (d, 2H), 6.92-6.87 (m, 3H), 6.67-6.66 (d, 2H), 3.83 (s, 3H), 3.82 (s, 3H), 3.79 (s, 3H), 3.48-3.46 (m, 2H), 2.89-2.22 (m, 1H), 2.14-2.06 (m, 1H), 1.67-1.60 (m, 1H), 1.53-1.42 (m, 4H).

PREPARATION 97

6,9-Dimethoxy-4-(4-methoxy-phenyl)-2,3,3a,4,5,9b-hexahydro-1H-cyclopenta[a]naphthalene

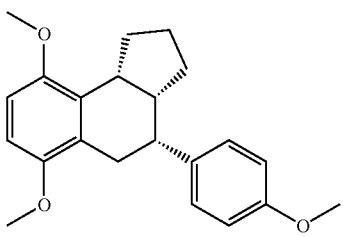

Preparation 97 is prepared from preparation 96 in a manner similar to preparation 9. (0.19 g, 94%): $^1$H NMR (CDCl$_3$) δ 7.24-07.22 (d, 2H), 6.88-6.85 (d, 2H), 6.66-6.65 (d, 2H), 3.81 (s, 3H), 3.80 (s, 3H), 3.78 (s, 3H), 3.62-3.56 (m, 1H), 3.13-3.08 (m, 1H), 3.02-2.97 (m, 1H), 2.71-2.64 (m, 1H), 2.60-2.52 (m, 1H), 2.40-2.33 (m, 1H), 1.53-1.23 (m, 5H).

PREPARATION 98

6-Hydroxy-8-methoxy-4-(4-methoxy-phenyl)-1,2,3,3a,4,9b-hexahydro-cyclopenta[a]naphthalen-5-one

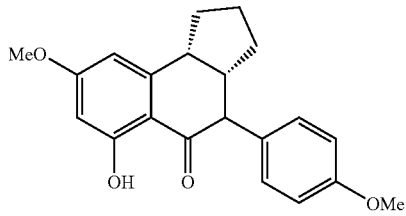

Combine 6,8-Dimethoxy-4-(4-methoxy-phenyl)-1,2,3,3a,4,9b-hexahydro-cyclopenta[a]naphthalen-5-one (0.15 g, 0.43 mmol), boron trichloride (2.1 ml, 1.0M in methylene chloride), and Ch$_2$Cl$_2$ (10 ml). Stir 3.5 hours at r.t. Quench with methanol, add water and extract with ethyl acetate. Wash with water, dry and concentrate in vacuo to give the titled compound (0.148 g, 100%). MS m/z 339 (M−1).

PREPARATION 99

8-Methoxy-4-(4-methoxy-phenyl)-2,3,3a,9b-tetrahydro-1H-cyclopenta[a]naphthalen-6-ol

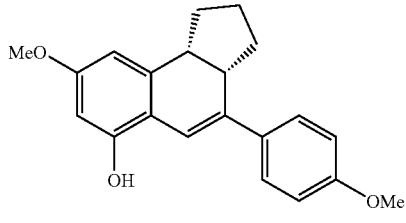

Preparation 99 is prepared from preparation 98 in a manner similar to preparations 7 and 8. $^1$H NMR (CDCl$_3$): 7.43 (m, 2H), 6.9 (d, J=8.8 Hz, 2H), 6.85 (m, 1H), 6.45(m, 1H), 6.2 (s, 1H), 3.83 (s, 3H), 3.8 (m, 3H), 3.4-3 (m, 1H), 2.2-1.95 (m, 3H), 1.7-1.4 (m, 4H).

PREPARATION 100

8-Methoxy-4-(4-methoxy-phenyl)-2,3,3a,4,5,9b-hexahydro-1H-cyclopenta[a]naphthalen-6-ol

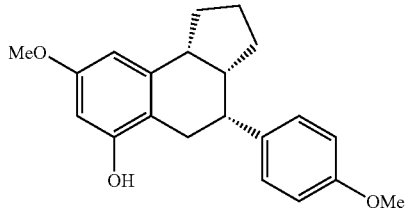

Preparation 100 is prepared from preparation 99 in a manner similar to preparation 9. ¹H NMR (CDCl₃): 7.23 (d, J=8.8 Hz, 2H), 6.87 (d, J=8.8 Hz, 2H), 6.38 (s, 1H), 6.24 (s, 1 H), 3.81 (s, 3H), 3.78(s, 3H), 3.4 (m, 1H), 3.1 (m, 1H), 2.85(m, 1H), 2.7 (m, 1H), 2.5 (m, 1H), 2.19 (m, 1H), 1.7-1.1 (m, 5H).

PREPARATION 101

Trifluoromethanesulfonic acid 8-methoxy-4-(4-methoxy-phenyl)-2,3,3a,4,5,9b-hexahydro-1H-cyclopenta[a]naphthalen-6-yl ester

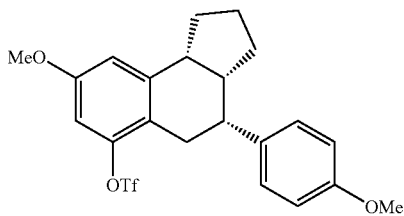

Combine 8-Methoxy-4-(4-methoxy-phenyl)-2,3,3a,4,5,9b-hexahydro-1H-cyclopenta[a]naphthalen-6-ol (0.43 g, 1.33 mmol), triflic anyhydride (0.56 ml, 3.31 ml), 2,6-di-t-butyl-4-methylpyridine (1.36 g, 6.63 mmol) in methylene chloride (40 ml) and stir 15 hours at r.t. Wash 2× with 1N HCl, 2× with water, dry over anhydrous sodium sulfate and concentrate to a residue which is chromatographed on silica gel with hexanes/ethyl acetate, 9-1 to yield the titled compound (0.38 g, 63%). ¹H NMR (CDCl₃): 7.2 (d, J=8.8 Hz, 2H), 6.88 (d, J=8.8 Hz, 2H), 6.77 (s, 1H), 6.65 (s, 1 H), 3.81 (s, 6H), 3.45 (m, 1H), 3.1 (m, 1H), 2.95(m, 1H), 2.85 (m, 1H), 2.59 (m, 1H), 2.21 (m, 1H), 1.6-1.35 (m, 5H).

PREPARATION 102

6-(4-Chloro-phenyl)-8-methoxy-4-(4-methoxy-phenyl)-2,3,3a,4,5,9b-hexahydro-1H-cyclopenta[a]naphthalene

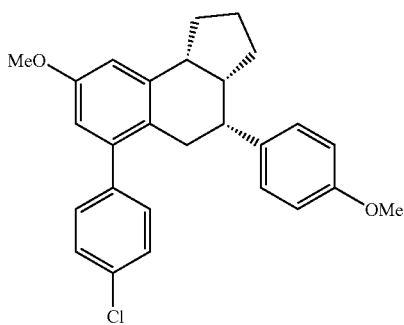

Combine trifluoro-methanesulfonic acid 8-methoxy-4-(4-methoxy-phenyl)-2,3,3a,4,5,9b-hexahydro-1H-cyclopenta[a]naphthalen-6-yl ester (0.046 g, 0.1 mmol), 4-chlorophenyboronic acid (0.019 g, 0.12 mmol), tetrakis (triphenylphosphine)palladium(0) (0.006 g, 5 mole %), sodium carbonate (0.12 ml 2N), and toluene/ethanol (4-1). Purge in vacuo briefly, and heat at 90° C. for 12 hours. Remove solvent, take in ethyl acetate and wash with water. Dry over anhydrous sodium sulfate and chromatograph the residue on silica gel with 5% ethyl acetate in hexanes to yield the titled compound (0.13 g, 31%). ¹H NMR (CDCl₃): 7.34 (d, J=8.8 Hz, 2H), 7.26 (d, J=8.8 Hz, 2 H), 7.1 (d, J=8.87 Hz, 2H), 6.8 (d, J=8.8 Hz, 2H), 6.78 (s, 1H), 6.62 (s, 1H), 3.82 (s, 3H), 3.77 (s, 3H), 3.45 (m, 1H), 2.98 (m, 1H), 2.85(m, 1H), 2.57 (m, 1H), 2.3 (m, 1H), 2.21 (m, 1H), 1.65-1.2 (m, 5H).

PREPARATION 103

8-Methoxy-4-(4-methoxy-phenyl)-2,3,3a,4,5,9b-hexahydro-1H-cyclopenta[a]naphthalene-6-carboxylic acid methyl ester

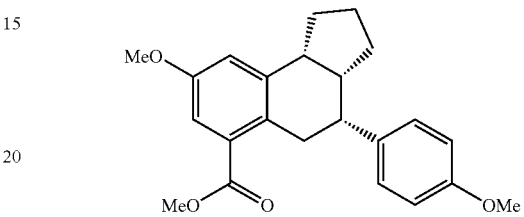

Combine trifluoro-methanesulfonic acid 8-methoxy-4-(4-methoxy-phenyl)-2,3,3a,4,5,9b-hexahydro-1H-cyclopenta[a]naphthalen-6-yl ester (0.1 g, 0.22 mmol), palladium acetate (0.0393 g, 0.18 mmol), 1,3-bis(diphenylphosphino)-propane (0.0723 g, 0.18 mmol), with dDMSO (6 ml) and methanol (2 m), and heat at 80-85° C. for 12 hours under an atmosphere of carbon monoxide. Remove solvent in vacuo, take in ethyl acetate and wash 5× with water. Dry over anhydrous sodium sulfate and chromatograph the residue on silica gel with 10% ethyl acetate in hexanes to yield the titled compound (0.07 g, 88%). ¹H NMR (CDCl₃): 7.21 (d, J=7.9, Hz, 2H), 7.19 (s, 1H), 6.9(s, 1H), 6.86 (d, J=7.9 Hz, 2H), 3.86 (s, 3H), 3.82 (s, 3H), 3.8 (s, 3H), 3.45 (m, 1H), 3.22 (m, 1H), 3.1 (m, 2H), 2.58 (m, 1H), 2.2 (m, 1H), 1.6-1.3 (m, 5H).

PREPARATION 104

[8-Methoxy-4-(4-methoxy-phenyl)-2,3,3a,4,5,9b-hexahydro-1H-cyclopenta[a]naphthalen-6-yl]-methanol

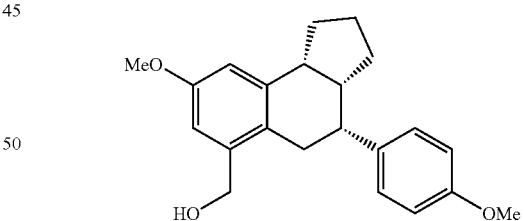

Combine 8-Methoxy-4-(4-methoxy-phenyl)-2,3,3a,4,5,9b-hexahydro-1H-cyclopenta[a]naphthalene-6-carboxylic acid methyl ester (0.16 g, 0.44 mmol), lithium aluminum hydride (0.08 g, 1.31 mmol) in tetrahydrofuran (10 ml) and stir for 2.5 hours. Add water (0.05 g), add 15% NaOH (0.05 g), add water (0.15 g) and stir 30 minutes. Add EtOAC, filter ppt. Rinse organic layer with water, then 1 n HCl, then water. Dry over anhydrous sodium sulfate and remove solvent in vacuo to yield the titled compound (0.153 g, 100%). H NMR (CDCl₃): 7.22 (d, J=8.8, Hz, 2H), 6.87 (d, J=8.4 Hz, 2H), 6.82 (s, 1H), 6.71(s, 1H), 4.7 (s, 2H), 3.81 (s, 3H), 3.45 (m, 1H), 3.1 (m, 1H), 2.85 (m, 2H), 2.55 (m, 1H), 2.2 (m, 1H), 1.6-1.3 (m, 5H).

PREPARATION 105

8-Hydroxy-4-(4-hydroxy-phenyl)-2,3,3a,4,5,9b-hexahydro-1H-cyclopenta[a]naphthalene-6-carbaldehyde

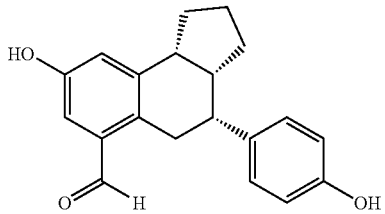

Combine 6-Bromomethyl-4-(4-hydroxy-phenyl)-2,3,3a,4,5,9b-hexahydro-1H-cyclopenta[a]naphthalen-8-ol (0.037 g, 0.1 mmol), trimethylamine N-oxide (0.03 g, 0.4 mmol), DMSO (1.5 ml), and methylene chloride (0.5 ml) and stir at 0-5° C. for 30 minutes. Add water and ethyl acetate. Wash organic layer 5× with water, dry over anhydrous sodium sulfate and concentrate to a residue which yields after separation on silica gel with 33% EtOAC/hexanes, the titled compound (0.12 g, 39%). $^1$H NMR (CD$_3$OD) 10.26 (s, 1H), 7.18 (d, J=8.4, Hz, 2H), 7.12 (s, 1H), 6.97 (s, 1H), 6.77 (d, J=7.9 Hz, 2H), 3.4 (m, 1H), 3.15 (m, 1H), 3.0 (m, 2H), 2.55(m, 1H) 2.2 (m, 1H), 1.6-1.2. MS m/z 307 (M−1).

PREPARATION 106

2-(3,5-Dimethoxy-phenyl)-cyclohexanol

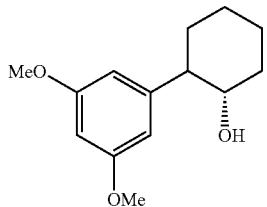

Preparation 106 is prepared from cyclohexene oxide and 1-bromo-3,5-dimethoxybenzene in a manner similar to preparation 10. $^1$H NMR (CDCl$_3$): 6.41 (s, 2H), 6.35(s, 1H), 3.79 (s, 6H), 3.65 (m, 1H), 2.37 (m, 1H), 2.1 (m, 1H), 1.85 (m, 2H), 1.75 (m, 1H)1.6-1.2 (m, 4H).

PREPARATION 107

2-(3,5-Dimethoxy-phenyl)-cyclohexanone

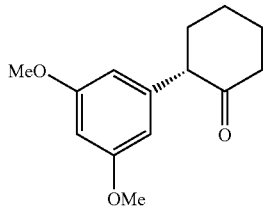

Preparation 107 is prepared from preparation 106 in a manner similar to preparation 11. $^1$H NMR (CDCl$_3$): 6.4 (s, 1H), 6.33(s, 2H), 3.81 (s, 6H), 3.59 (m, 1H), 2.5 (m, 2H), 2.3 (m, 1H), 2.2-1.95 (m, 3H), 1.85 (m, 2H).

PREPARATION 108

[2-(3,5-Dimethoxy-phenyl)-cyclopent-1-enyl]-acetic acid ethyl ester

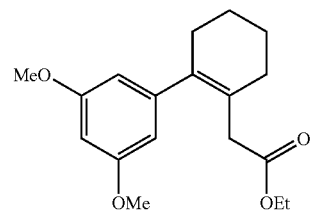

Preparation 108 is prepared from preparation 107 in a manner similar to preparations 1 and 2. $^1$H NMR (CDCl$_3$): 6.38 (s, 3H), 4.14 (q, J=7 Hz, 2H), 3.8 (s, 6H), 3-2.8 (m, 2H), 2.3 (s, 2H), 2.15 (s, 2H), 1.75 (m, 4H), 1.6 (s, 2H), 1.25 (q, J=7 Hz, 3H).

PREPARATION 109

[2-(3,5-Dimethoxy-phenyl)-cyclopentyl]-acetic acid ethyl ester

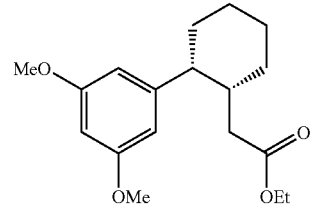

Preparation 109 is prepared from preparation 108 in a manner similar to preparation 3. $^1$H NMR (CDCl$_3$): 6.38 (s, 2H), 6.33 (s, 1H), 4.04 (q, J=7 Hz, 2H), 3.81 (s, 6H), 2.9 (m, 1H), 2.55 (m, 1H), 2.35 (m, 1H), 2.3-1.3 (series of m, 9H), 1.25 (q, J=7 Hz, 3H).

PREPARATION 110

6,8-Dimethoxy-2,3,4,4a,10,10a-hexahydro-1H-phenanthren-9-one

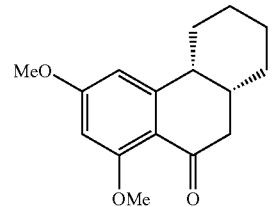

Preparation 110 is prepared from preparation 109 in a manner similar to preparation 5. MS m/z 261 (M+1).

PREPARATION 111

6,8-Dimethoxy-10-(4-methoxy-phenyl)-2,3,4,4a,10,10a-hexahydro-1H-phenanthren-9-one

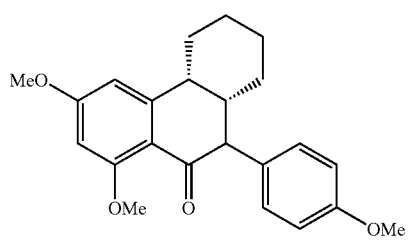

Preparation 111 is prepared from preparation 110 in a manner similar to preparation 6. MS m/z 367 (M+1).

PREPARATION 112

8-Hydroxy-6-methoxy-10-(4-methoxy-phenyl)-2,3,4,4a,10,10a-hexahydro-1H-phenanthren-9-one

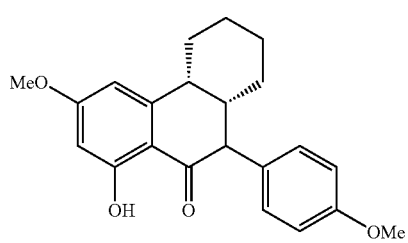

Preparation 112 is prepared from preparation 111 in a manner similar to preparation 98. MS m/z 353 (M+1).

PREPARATION 113

3-Methoxy-9-(4-methoxy-phenyl)-4b,5,6,7,8,8a,9,10-octahydro-phenanthrene-1,10-diol

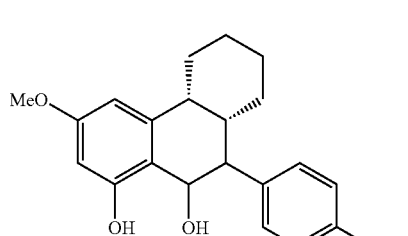

Preparation 113 is prepared from preparation 112 in a manner similar to preparation 7. MS m/z 353 (M−1).

PREPARATION 114

3-Methoxy-9-(4-methoxy-phenyl)-4b,5,6,7,8,8a-hexahydro-phenanthren-1-ol

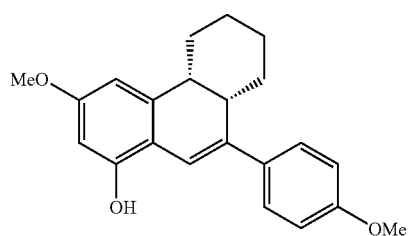

Preparation 114 is prepared from preparation 113 in a manner similar to preparation 8. MS m/z 335 (M−1).

PREPARATION 115

3-Methoxy-9-(4-methoxy-phenyl)-4b,5,6,7,8,8a,9,10-octahydro-phenanthren-1-ol

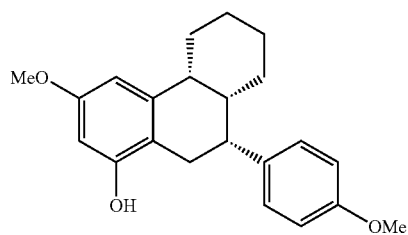

Preparation 115 is prepared from preparation 114 in a manner similar to preparation 9. MS m/z 337 (M−1).

PREPARATION 116

Trifluoro-methanesulfonic acid 3-methoxy-9-(4-methoxy-phenyl)-4b,5,6,7,8,8a,9,10-octahydro-phenanthren-1-yl ester

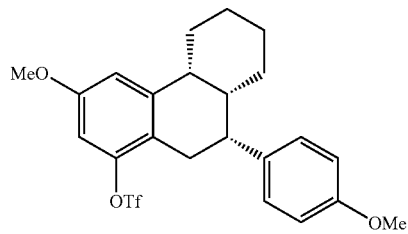

Preparation 116 is prepared from preparation 115 in a manner similar to preparation 101. $^1$H NMR (CDCl$_3$): 7.26 (d, J=8.4 Hz, 2H), 7.03 (s, 1H), 6.94 (d, J=8.8 Hz, 2H), 6.74 (s, 1H), 3.86 (s, 6H), 3.25 (s, 1H), 3.1 (m, 3H), 2.5 (m, 1H), 2.1 (m, 1H), 1.8-0.9 (m, 7H).

PREPARATION 117

3-Methoxy-9-(4-methoxy-phenyl)-4b,5,6,7,8,8a,9,10-octahydro-phenanthrene-1-carboxylic acid methyl ester

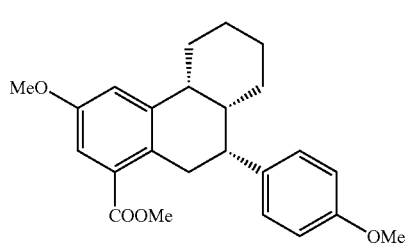

Preparation 117 is prepared from preparation 116 in a manner similar to preparation 103. $^1$H NMR (CDCl$_3$): 7.3 (m, 2H), 7.2 (s, 1H), 6.93 (d, J=8.4 Hz, 2H), 3.92 (s, 3H), 3.88(s, 3H), 3.85 (s, 3H), 3.5-3.05 (m, 4H), 2.5 (m, 1H), 2.05 (m, 1H), 1.75 (m, 1H), 1.7-1.05 (m, 6H).

PREPARATION 118

[3-Methoxy-9-(4-methoxy-phenyl)-4b,5,6,7,8,8a,9,10-octahydro-phenanthren-1-yl]-methanol

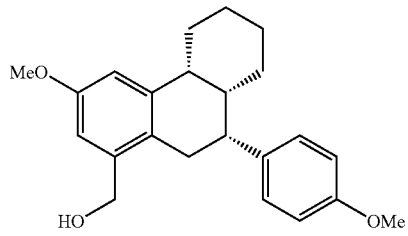

Preparation 118 is prepared from preparation 117 in a manner similar to preparation 104. $^1$H NMR (CDCl$_3$): 7.3 (m, 2H), 6.95 (m, 4H), 4.77 (s, 2H), 3.87 (s, 3H), 3.88(s, 3H), 3.85 (s, 3H), 3.25 (s, 1H), 3.15 (m, 1H), 3.05 (m, 1H), 2.9 (m, 1H), 2.5 (m, 1H), 2.05 (m, 1H), 1.8-1.05 (m, 7H).

PREPARATION 119

3-Methoxy-9-(4-methoxy-phenyl)-4b,5,6,7,8,8a,9,10-octahydro-phenanthrene-1-carboxylic acid

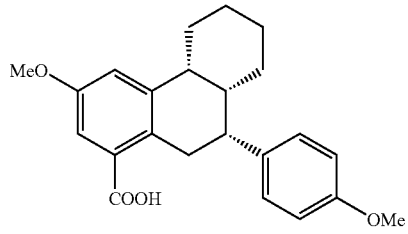

Preparation 119 is prepared from preparation 117 in a manner similar to example 13. MS m/z 365 (M−1).

PREPARATION 120

3-Methoxy-9-(4-methoxy-phenyl)-4b,5,6,7,8,8a,9,10-octahydro-phenanthrene-1-carbonyl chloride

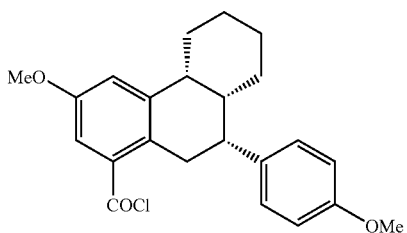

Combine 3-Methoxy-9-(4-methoxy-phenyl)-4b,5,6,7,8,8a,9,10-octahydro-phenanthrene-1-carboxylic acid (0.12 g, 0.33 mmol) and thionyl chloride (4 ml) and heat at 60° C. for 2 hours. Remove thionyl chloride in vacuo at 40° C. Take the residue into ethyl acetate and wash with sodium bicarbonate solution 1×, followed by water. Dry the organic layer over anhydrous sodium sulfate and remove solvent in vacuo at 40° C. to yield preparation 120 (0.133 g, 100%). $^1$H NMR (CDCl$_3$): 7.62 (s, 1H), 7.3 (m, 3H), 6.93 (d, J=8.4, 2H), 3.92 (s, 3H), 3.85 (s, 3H), 3.3(m, 2H), 3.1 (m, 2H), 3.05 (m, 1H), 2.5 (m, 1H), 2.1 (m, 1H), 1.8 (m, 1H), 1.5 (m, 1H), 1.4-0.8 (m, 4H).

PREPARATION 121

3-Methoxy-9-(4-methoxy-phenyl)-4b,5,6,7,8,8a,9,10-octahydro-phenanthrene-1-carboxylic acid amide

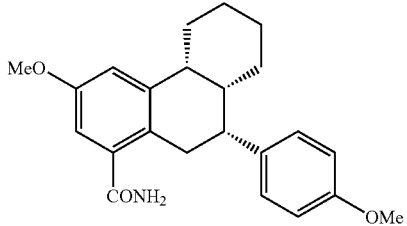

Combine 3-Methoxy-9-(4-methoxy-phenyl)-4b,5,6,7,8,8a,9,10-octahydro-phenanthrene-1-carbonyl chloride (0.08 g, 0.18 mmol), NH$_4$OH (2 ml), and diethyl ether (1 ml) at 0-5° C. and stir as such 2 hours. Dilute with ethyl acetate and wash with water. Dry over anhydrous sodium sulfate, and remove solvent in vacuo at 40° C. to yield preparation 121 (0.069 g, 100%). MS m/z 366 (M+1).

PREPARATION 122

3-Methoxy-9-(4-methoxy-phenyl)-4b,5,6,7,8,8a,9,10-octahydro-phenanthrene-1-carbonitrile

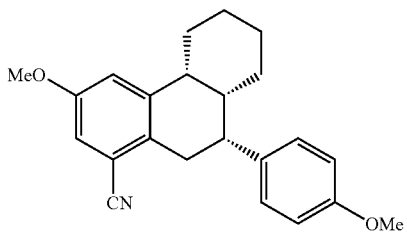

Combine 3-Methoxy-9-(4-methoxy-phenyl)-4b,5,6,7,8,8a,9,10-octahydro-phenanthrene-1-carboxylic acid amide (0.69 g, 0.19 mmol), and triethylamine (0.038 g, 0.38 mmol) in methylene chloride (2.5 ml) at 0-5° C. and add trifluoroacetic anhydride (0.044 g, 0.21 mmol). Let stir at r.t. for 15 minutes. Add water, separate organic layer. Dry over anhydrous sodium sulfate and remove solvent in vacuo to yield preparation 122 (0.066 g, 100%). ¹H NMR (CDCl₃): 7.24 (d, J=8.8 Hz, 2H), 7.22 (s, 1H), 7.06 (s, 1H), 6.94 (d, J=8.8, 2H), 3.86 (m, 6H), 3.2 (m, 4H), 2.5 (m, 1H), 2.1 (m, 1H), 1.8-0.8 (m, 7H).

PREPARATION 123

7-Bromo-6-methoxy-10-(4-methoxy-phenyl)-1,2,3,4,4a,9,10,10a-octahydro-phenanthrene

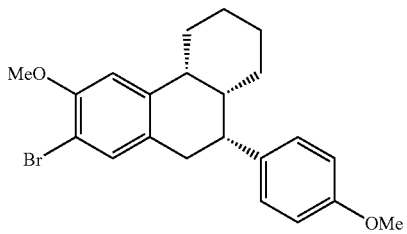

Combine 6-Methoxy-10-(4-methoxy-phenyl)-1,2,3,4,4a,9,10,10a-octahydro-phenanthrene (chiral) (0.02 g, 0.32 mmol) and methylene chloride (10 ml) and add bromine (0.0162 ml, 0.32 mmol) at 0-5° C. over 15 minutes. Stir as such one hour. Remove volatiles in vacuo at 40° C. to yield the titled compound (0.16 g, 100%). ¹H NMR (CDCl₃): 7.38 (s, 1H), 7.25 (d, J=8.8 Hz, 2H), 6.9 (m, 3H), 3.93 (s, 3H), 3.85 (s, 3H), 3.2 (m, 3H), 2.85 (dd, J=4 and 11, 1H), 2.48 (d, J=14 Hz, 1H), 2.06 (m, 1H), 1.8-0.8 (m, 7H).

PREPARATION 124

1-[3-Methoxy-9-(4-methoxy-phenyl)-4b,5,6,7,8,8a,9,10-octahydro-phenanthren-2-yl]-ethanone

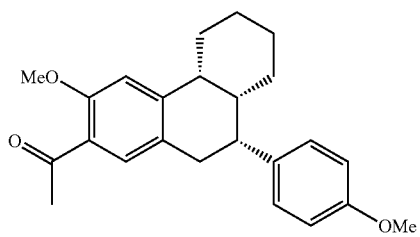

Combine 6-Methoxy-10-(4-methoxy-phenyl)-1,2,3,4,4a,9,10,10a-octahydro-phenanthrene (0.13 g, 0.4 mmol) and methylene chloride (6 ml). Cool to −5° C. and add aluminum chloride (0.11, 0.81 mmol) followed by acetyl chloride (0.032 g, 0.4 mmol). After 2 hours, add ice, water and 1N HCl. Filter precipitate and rinse filtrate with sodium bicarbonate solution solution followed by brine. Remove solvent in vacuo, and chromatograph on silica gel with 17% ethyl acetate/hexanes to yield the titled compound (0.081 g, 55%). ¹H NMR (CDCl₃). MS m/z 365, (M+1).

PREPARATION 125

6,7-Dimethoxy-10-(4-methoxy-phenyl)-1,2,3,4,4a,9,10,10a-octahydro-phenanthrene

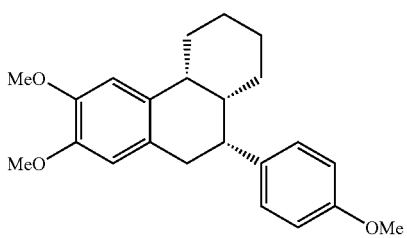

Combine 7-Bromo-6-methoxy-10-(4-methoxy-phenyl)-1,2,3,4,4a,9,10,10a-octahydro-phenanthrene (chiral) (0.025 g, 0.06 mmol), NaOMe 5N (1.4 ml, 7 mmol), CuIBr (0.005 g, 0.034 mmol) and ethyl acetate (0.005 ml, 0.05 mmol) and heat at 115° C. for 1.5 hours. Cool, and add 1N HCl and extract with ethyl acetate. Wash organic layer with water, dry over anhydrous sodium sulfate and remove solvent in vacuo. Chromatograph on silica gel with 9% ethyl acetate/hexanes to yield the titled compound (0.012 g, 55%). ¹H NMR (CDCl₃). MS m/z 352.9 (M+1).

PREPARATION 126

6-Methoxy-10-(4-methoxy-phenyl)-7-methyl-1,2,3,4,4a,9,10,10a-octahydro-phenanthrene

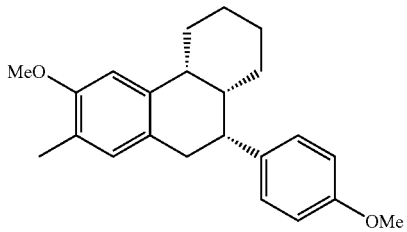

At −78° C., combine 7-Bromo-6-methoxy-10-(4-methoxy-phenyl)-1,2,3,4,4a,9,10,10a-octahydro-phenanthrene (chiral) (0.027 g, 0.067 mmol), and CH₃Li (0.09 ml, 1.6M), then add t-BuLi (0.1 ml, 1.7M). After 30 minutes add CH₃I (0.04 ml, 0.61 mmol) and remove cooling. After 1 hour at r.t., add ammonium chloride solution solution and ethyl acetate. Wash organic layer with water, dry over anhydrous sodium sulfate, remove solvent in vacuo to yield the titled compound (0.026 g, 100%). ¹H NMR (CDCl₃):): 7.27 (d, J=8.8 Hz, 2H), 6.99 (s, 1H), 6.93 (d, J=8.8 HZ, 2H), 6.89 (s, 1H), 3.87 (s, 3H), 3.86 (s, 3H), 3.2 (m, 2H), 2.85 (dd, J=4 and 11, 1H), 2.48 (d, J=14 Hz, 1H), 2.06 (m, 1H), 1.8-0.8 (m, 8H).

PREPARATION 127

6-Methoxy-10-(4-methoxy-phenyl)-7-propyl-1,2,3,4,4a,9,10,10a-octahydro-phenanthrene

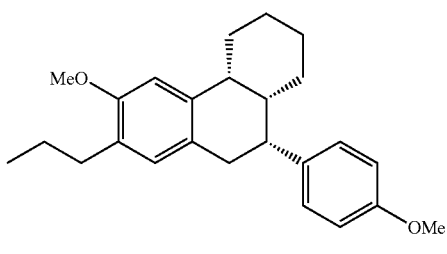

Preparation 127 is prepared from preparation 123 in a manner similar to preparation 126. $^1$H NMR (CDCl$_3$): 7.2 (d, J=8.8 Hz, 2H), 6.99 (s, 1H), 6.93 (d, J=8.8 Hz, 2H), 6.89 (s, 1H) 3.87 (s, 3H), 3.86 (s, 3H), 3.2 (m, 3H), 2.85 (m, 1H), 2.65 (m, 1H), 2.5 (m, 2H), 2.06 (m, 2H), 1.8-1.1 (m, 8H), 1.05 (t, J=7.5 and 5.7 Hz, 3H).

PREPARATION 128

7-Isopropenyl-6-methoxy-10-(4-methoxy-phenyl)-1,2,3,4,40,10,10a-octahydro-phenanthrene

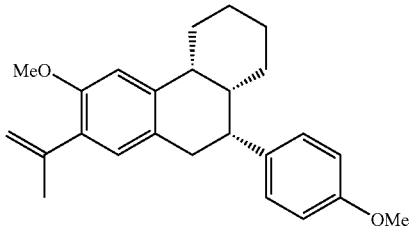

Preparation 128 is prepared from preparation 124 in a manner similar to example 18. MS m/z 363(M+1).

PREPARATION 129

7-Isopropyl-6-methoxy-10-(4-methoxy-phenyl)-1,2,3,4,4a,9,10,10a-octahydro-phenanthrene

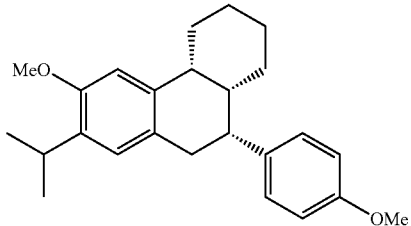

Combine 7-Isopropenyl-6-methoxy-10-(4-methoxy-phenyl)-1,2,3,4,4a,9,10,10a-octahydro-phenanthrene (0.14 g, 0.39 mmol) and 10% Pd/C (0.13 g) and reduce at 50 psi of H$_2$O.N. Filter catalyst and remove solvent in vacuo to yield the titled compound (0.13 g, 93%). $^1$H NMR (CDCl$_3$): 7.28 (d, J=8.4 Hz, 2H), 7.02 (s, 1H), 6.92 (d, J=8.8 HZ, 2H), 6.89 (s, 1H), 3.87 (s, 3H), 3.85 (s, 3H), 3.25 (m, 4H), 2.85 (m, 1H), 2.5 (m, 1H), 2.06 (m, 1H), 1.8-1.1 (m, 13H).

PREPARATION 130

3-Methoxy-9-(4-methoxy-phenyl)-4b,5,6,7,8,8a,9,10-octahydro-phenanthrene-2-carbaldehyde

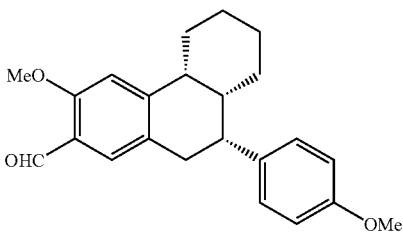

Preparation 130 is prepared from preparation 123, using dimethylformamide as the electrophile, in a manner similar to preparation 126. MS m/z 351 (M+1).

PREPARATION 131

3-[3-Methoxy-9-(4-methoxy-phenyl)-4b,5,6,7,8,8a,9,10-octahydro-phenanthren-2-yl]-acrylic acid ethyl ester

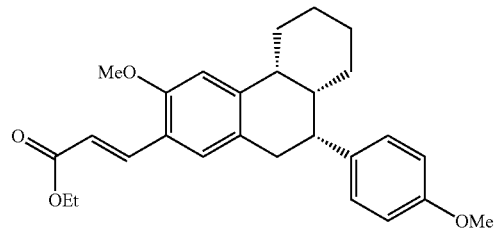

Combine 3-Methoxy-9-(4-methoxy-phenyl)-4b,5,6,7,8,8a,9,10-octahydro-phenanthrene-2-carbaldehyde (1.77 g, 5.13 mmol), carboethoxy-methylene triphenylphosphorane (03.19 g, 9.03 mmol) in toluene (53 ml) and reflux 15 hours. Remove solvent in vacuo, slurry with diethyl ether and chromatograph the residue from the concentrated filtrate on silica gel with 20% ethyl acetate/hexanes, then 25% ethyl acetate/hexanes to yield the titled compound (1.61 g, 76%). MS m/z 421(M+1).

PREPARATION 132

3-[3-Methoxy-9-(4-methoxy-phenyl)-4b,5,6,7,8,8a,9,10-octahydro-phenanthren-2-yl]-propionic acid ethyl ester

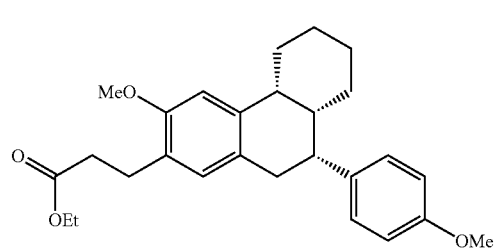

Preparation 132 is prepared from preparation 131 in a manner similar to preparation 129. $^1$H NMR (CDCl$_3$) 7.27 (d, J=7.1 Hz, 2H), 6.98 (s, 1H), 6.93 (d, J=7 HZ, 2H), 6.88 (s, 1H) 4.19 (q, J=5 and 7 Hz, 2H), 3.86 (s, 6H), 3.2 (m, 3H), 2.95 (m, 1H), 2.85 (m, 1H), 2.65 (m, 3H), 2.55 (m, 1H), 2.06 (m, 1H), 1.8-1.1 (m, 10H).

PREPARATION 133

Methanesulfonic acid 9-(4-methanesulfonyloxy-phenyl)-2-(3-methanesulfonyloxy-propyl)-4b,5,6,7,8,8a,9,10-octahydro-phenanthren-3-yl ester

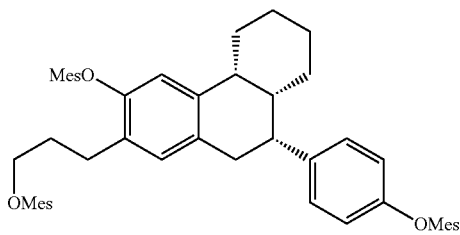

Combine 9-(4-Hydroxy-phenyl)-2-(3-hydroxy-propyl)-4b,5,6,7,8,8a,9,10-octahydro-phenanthren-3-ol (0.1 g, 0.284 mmol), methanesulfonyl chloride (0.11 g, 0.94 mmol), triethylamine (0.19 g, 1.9 mmol), 2,6-dimethylaminopyridine (0.02 g, cat.) and methylene chloride (5 ml) and stir 15 hours. Remove solvent in vacuo and add ethyl acetate and water. Wash 1× with sodium bicarbonate solution solution followed by water. Dry over anhydrous sodium sulfate and remove solvent in vacuo to yield preparation 133 (0.16 g, g, 96%). $^1$H NMR (CDCl$_3$): 7.34 (d, J=8.8 Hz, 2H), 7.28 (d, J=8 Hz, 2H), 7.26 (s, 1H), 7.09 (s, 1H), 4.28 (t, J=7.1 and 6.2 Hz, 2H), 3.24 (m, 6H), 3.16 (s, 3H), 3.03 (s, 3H), 2.9 (d, J=11.9 Hz, 1H), 2.82 (t, J=7.5 and 8.4 Hz, 3H), 2.45 (d, J=13.7 Hz, 1H), 2.1 (m, 3H), 1.8-1.0 (m, 6H).

PREPARATION 134

Methanesulfonic acid 9-(4-methanesulfonyloxy-phenyl)-2-(3-methoxy-propyl)-4b,5,6,7,8,8a,9,10-octahydro-phenanthren-3-yl ester

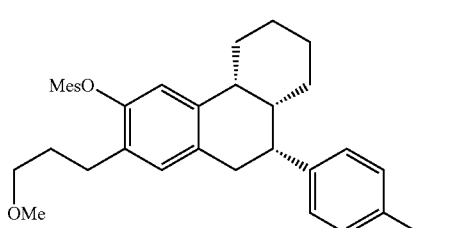

Preparation 134 is prepared in a manner similar to Example 16. MS m/z 523 (M+1).

PREPARATION 135

3-Methoxy-9-(4-methoxy-phenyl)-4b,5,6,7,8,8a,9,10-octahydro-phenanthrene-2-carboxylic acid methyl ester

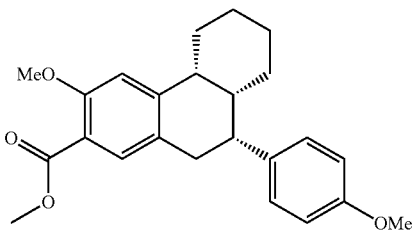

At −78° C., combine 7-Bromo-6-methoxy-10-(4-methoxy-phenyl)-1,2,3,4,4a,9,10,10a-octahydro-phenanthrene (0.2 g, 0.5 mmol), tetrahydrofuran (4 ml), CH$_3$Li (0.623 ml, 1.6M), then add t-BuLi (0.59 ml, 1.7M). After 30 minutes add methyl chloroformate (0.19 g, 2.0 mmol) and remove cooling. After 2 hours at r.t., add ammonium chloride solution solution and ethyl acetate. Wash organic layer with water, dry over anhydrous sodium sulfate, remove solvent in vacuo to yield the titled compound (0.21 g, 100%). MS m/z 381 (M−1).

PREPARATION 136

3-Hydroxy-9-(4-hydroxy-phenyl)-4b,5,6,7,8,8a,9,10-octahydro-phenanthrene-2-carboxylic acid

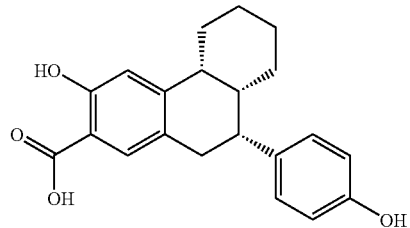

Preparation 136 is prepared from preparation 135 in a manner similar to Example 1. MS m/z 337 (M−1).

PREPARATION 137

3-Hydroxy-9-(4-methoxy-phenyl)-4b,5,6,7,8,8a,9,10-octahydro-phenanthrene-2-carbaldehyde

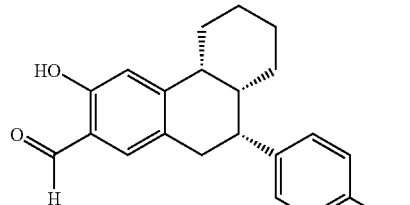

Preparation 137 is prepared from preparation 130 in a manner similar to Example 1. MS m/z 321 (M−1).

PREPARATION 138

Trifluoro-methanesulfonic acid 6-methoxy-10-(4-methoxy-phenyl)-1,2,3,4,4a,10a-hexahydro-phenanthren-9-yl ester

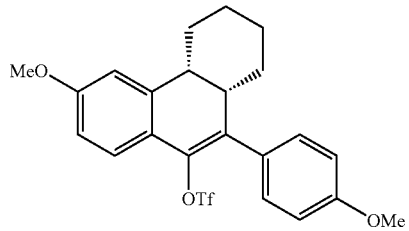

Combine 6-methoxy-10-(4-methoxy-phenyl)-2,3,4,4a,10,10a-hexahydro-1H-phenanthren-9-one (1.11 g, 3.18 mmol), 2,6-di-tert-butyl-(4-methylpyridine) (1.34 g, 6.54 mmol), triflic anhydride (1.0 mL, 5.94 mmol), and methylene chloride (30.0 mL), and stir under nitrogen atmosphere at room temperature. After 18 hours, quench reaction with 1N HCl (5 mL) and extract with ethyl acetate. Wash the ethyl acetate with brine, then dry the organic phase with anhydrous sodium sulfate and concentrate. Flash chromatograph using 0% to 30% ethyl acetate/hexanes to yield the titled compound (1.33 g, 89%) as a yellow foam. TLC Rf=0.24 in 6:1 hexanes:ethyl acetate. $^1$H NMR (CDCl$_3$): 7.44 (d, 1H, J=8.8 Hz), 7.37 (d, 2H, J=8.4 Hz), 6.96 (m, 3H), 6.84 (d, 1H, J=8.4 Hz), 3.88 (m, 6H), 3.38 (s, 1H), 2.78 (m, 1H), 2.50 (d, 1H, J=13.7 Hz), 1.82 (m, 1H), 1.57 (m, 3H), 1.36 (m, 2H), 1.24 (m, 2H), 1.10 (m, 1H), 1.23 (m, 1H).

PREPARATION 139

6-Methoxy-10-(4-methoxy-phenyl)-1,2,3,4,4a,10a-hexahydro-phenanthren-9-carboxylic acid methyl ester

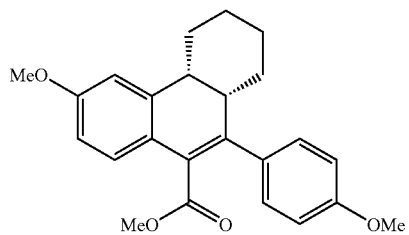

Combine trifluoro-methanesulfonic acid 6-methoxy-10-(4-methoxy-phenyl)-1,2,3,4,4a,10a-hexahydro-phenanthren-9-yl ester (19.83 g, 42.3 mmol), palladium acetate (1.93 g), dppb (4.58 g), Et$_3$N (60.0 mL), methanol (265 mL), and DMSO (400.0 mL), and stir under 100 psi of CO atmosphere at 80° C. After 18 hours, add ethyl acetate and wash the ethyl acetate 5× with brine, then dry the organic phase with anhydrous sodium sulfate and concentrate. Flash chromatograph using 5% to 30% ethyl acetate/hexanes to yield the titled compound (10.06 g, 63%) as a pinkish-white solid. TLC Rf=0.25 in 6:1 hexanes:ethyl acetate. $^1$H NMR (CDCl$_3$): 7.31 (m, 2H), 7.25 (d, 1H, J=8.4 Hz), 6.92 (m, 3H), 6.76 (dd, 1H, J=8.6, 2.4 Hz), 3.86 (m, 6H), 3.60 (s, 3H), 3.25 (d, 1H, J=4.4 Hz), 2.70 (m, 1H), 2.40 (m, 1H), 1.75 (m, 1H), 1.53 (m, 4H), 1.31 (m, 2H).

PREPARATION 140

6-Methoxy-10-(4-methoxy-phenyl)-1,2,3,4,4a,9,10,10a-octahydro-phenanthren-9-carboxylic acid methyl ester

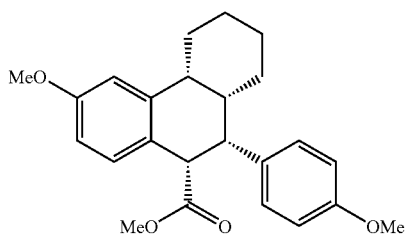

Combine 6-methoxy-10-(4-methoxy-phenyl)-1,2,3,4,4a,10a-hexahydro-phenanthren-9-carboxylic acid methyl ester (10.06 g, 26.6 mmol), 10% Pd—C (1.014 g), acetic acid (100 mL), methanol (150 mL), and ethyl acetate (150 mL), and stir under 100 psi of hydrogen atmosphere at 50° C. After 18 hours, filter reaction through Celite using ethyl acetate and concentrate to yield the titled compound (9.97 g, 99%) as a white solid. TLC Rf=0.25 in 6:1 hexanes:ethyl acetate. $^1$H NMR (CDCl$_3$): 7.28 (m, 1H), 7.22 (d, 2H, J=8.8 Hz), 6.98 (d, 1H, J=2.2 Hz), 6.84 (d, 2H, J=8.8 Hz), 6.80 (d, 1H, J=2.6 Hz), 4.33 (d, 1H, J=7.9 Hz), 3.86 (s, 3H), 3.82 (s, 3H), 3.55 (m, 1H), 3.51 (s, 3H), 3.06 (m, 1H), 2.36 (m, 2H), 1.78 (m, 3H), 1.38 (m, 4H).

PREPARATION 141

6-Methoxy-10-(4-methoxy-phenyl)-1,2,3,4,4a,9,10,10a-octahydro-phenanthren-9-carboxylic acid methyl ester

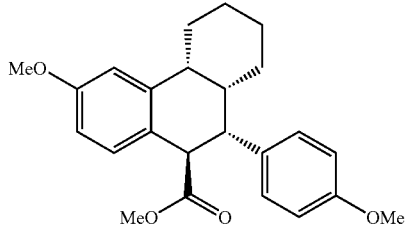

Combine methoxy-10-(4-methoxy-phenyl)-1,2,3,4,4a,9,10,10a-octahydro-phenanthren-9-carboxylic acid methyl ester (9.95 g, 26.15 mmol), NaOMe (0.283 g, 5.23 mmol), methanol (32 mL), and tetrahydrofuran (125 mL), and stir under nitrogen atmosphere at 40° C. After 3 hours, concentrate reaction to dryness and add ethyl acetate. Wash with water and then brine, dry the organic phase with anhydrous sodium sulfate and concentrate to yield the titled compound (10.03 g, 99%) as a yellow-white solid. TLC Rf=0.25 in 6:1 hexanes:ethyl acetate. $^1$H NMR (CDCl$_3$): 7.27 (d, 2H, J=8.8 Hz), 7.20 (d, 1H, J=8.4 Hz), 6.99 (m, 1H), 6.90 (d, 2H, J=8.4 Hz), 6.77 (dd, 1H, J=8.4, 2.6 Hz), 4.36 (d, 1H, J=12.3 Hz), 3.84 (m, 6H), 3.60 (s, 3H), 3.54 (dd, 1H, J=12.6, 2.9 Hz), 3.36 (s, 1H), 2.51 (d, 1H, J=14.1 Hz), 2.01 (m, 1H), 1.72 (m, 2H), 1.45 (m, 2H), 1.11 (m, 3H).

PREPARATION 142

[6-Methoxy-10-(4-methoxy-phenyl)-1,2,3,4,4a,9,10,10a-octahydro-phenanthren-9-yl]-methanol

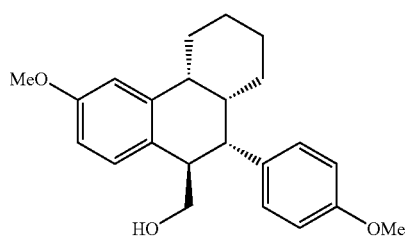

Combine 6-methoxy-10-(4-methoxy-phenyl)-1,2,3,4,4a,9,10,10a-octahydro-phenanthren-9-carboxylic acid methyl ester (4.25 g, 11.17 mmol), lithium aluminum hydride (1.20 g, 32.39 mmol), and tetrahydrofuran (150 mL), and reflux under nitrogen atmosphere. After 3 hours, quench reaction by adding reaction to a stirred solution of Rochelle's salt (Na K Tartrate) and ethyl acetate. After several hours, separate the organic phase and wash with brine. Dry the organic phase with anhydrous sodium sulfate and flash chromatograph using 5% to 30% ethyl acetate/hexanes to yield the titled compound (3.54 g, 90%) as a white solid. TLC Rf=0.13 in 4:1 hexanes:ethyl acetate. $^1$H NMR (CDCl$_3$): 7.43 (d, 1H, J=8.8 Hz), 7.26 (d, 2H, J=8.4 Hz), 7.00 (m, 1H), 6.93 (d, 2H, J=8.8 Hz), 6.84 (dd, 1H, J=8.4, 2.6 Hz), 4.05 (dd, 1H, J=11.2, 3.3 Hz), 3.86 (m, 6H), 3.62 (dd, 1H, J=11.0, 2.6 Hz), 3.34 (m, 3H), 2.49 (d, 1H, J=13.7 Hz), 1.95 (m, 1H), 1.65 (m, 2H), 1.45 (m, 2H), 1.30 (m, 1H), 1.16 (m, 2H).

PREPARATION 143

Toluene-4-sulfonic acid 6-methoxy-10-(4-methoxyphenyl)-1,2,3,4,4a,9,10,10a-octahydro-phenanthren-9-ylmethyl ester

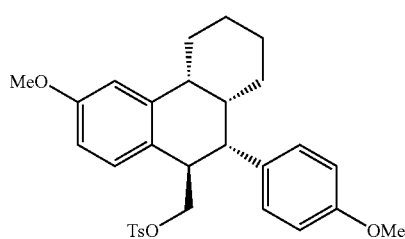

Combine [6-methoxy-10-(4-methoxy-phenyl)-1,2,3,4,4a,9,10,10a-octahydro-phenanthren-9-yl]-methanol (1.45 g, 3.81 mmol), TosCl (0.80 g, 4.19 mmol), Et$_3$N (1.2 mL, 8.38 mmol), 2,6-dimethylaminopyridine (140.0 mg, 1.14 mmol), and methylene chloride (30 mL), and stir under nitrogen atmosphere at room temperature. After 18 hours, concentrate reaction under vacuum and add ethyl acetate. Wash with water and then brine. Dry the organic phase with anhydrous sodium sulfate and concentrate to yield the titled compound (1.83 g, 95%) as a yellowish-white solid. TLC Rf=0.30 in 2:1 hexanes:ethyl acetate. $^1$H NMR (CDCl$_3$): 7.53 (d, 2H, J=8.4 Hz), 7.22 (d, 2H, J=8.4 Hz), 7.16 (d, 1H, J=8.8 Hz), 7.06 (d, 2H, J=8.8 Hz), 6.92 (d, 1H, J=2.2 Hz), 6.83 (d, 2H, J=8.4 Hz), 6.66 (dd, 1H, J=8.8, 2.6 Hz), 4.34 (dd, 1H, J=9.7, 2.6 Hz), 4.03 (dd, 1H, J=9.7, 4.0 Hz), 3.85 (s, 6H), 3.48 (d, 1H, J=11.9 Hz), 3.20 (s, 1H), 3.09 (dd, 1H, J=12.1, 3.3 Hz), 2.46 (s, 3H), 1.89 (m, 1H), 1.61 (m, 3H), 1.41 (d, 2H, J=9.7 Hz), 1.14 (m, 3H).

PREPARATION 144

6-Methoxy-10-(4-methoxy-phenyl)-9-methyl-1,2,3,4,4a,9,10,10a-octahydro-phenanthrene

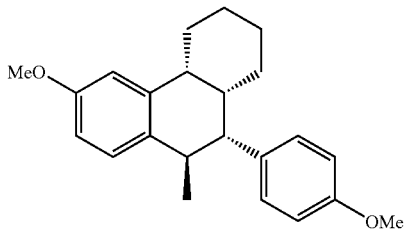

Combine toluene-4-sulfonic acid 6-methoxy-10-(4-methoxy-phenyl)-1,2,3,4,4a,9,10,10a-octahydro-phenanthren-9-ylmethyl ester (0.471 g, 0.93 mmol), lithium aluminum hydride (0.069 g, 1.86 mmol), and tetrahydrofuran (8.0 mL), and reflux under nitrogen atmosphere. After 5 hours, quench reaction by adding reaction to a stirred solution of Rochelle's salt (Na K Tartrate) and ethyl acetate. After several hours, separate the organic phase and wash with brine. Dry the organic phase with anhydrous sodium sulfate and flash chromatograph using 0% to 20% ethyl acetate/hexanes to yield the titled compound (0.267 g, 85%) as a white solid. TLC Rf=0.43 in 3:1 hexanes:ethyl acetate. $^1$H NMR (CDCl$_3$): 7.35 (d, 1H, J=8.4 Hz), 7.23 (d, 2H, J=8.4 Hz), 6.94 (m, 3H), 6.82 (dd, 1H, J=8.8, 2.6 Hz), 3.86 (s, 6H), 3.31 (m, 2H), 2.82 (dd, 1H, J=11.9, 2.6 Hz), 2.50 (d, 1H, J=13.7 Hz), 1.89 (m, 1H), 1.64 (m, 2H), 1.44 (m, 2H), 1.16 (m, 6H).

PREPARATION 145

6-Methoxy-10-(4-methoxy-phenyl)-1,2,3,4,4a,9,10,10a-octahydro-phenanthrene-9-carboxylic acid

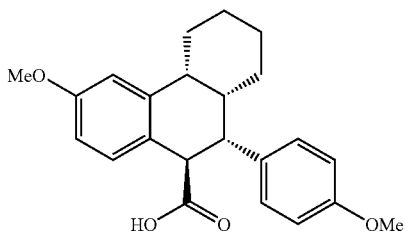

Combine 6-methoxy-10-(4-methoxy-phenyl)-1,2,3,4,4a,9,10,10a-octahydro-phenanthren-9-carboxylic acid methyl ester (1.03 g, 2.71 mmol), Methanol (20.0 mL), tetrahydrofuran (2 mL), and lithium hydroxide aqueous (5 mL), stir at reflux. After 18 hours, add 5N HCl until reaction is acidic, then extract with ethyl acetate and wash with brine. Dry the organic phase with anhydrous sodium sulfate then concentrate to yield the titled compound (0.97 g, 97%) as a white solid. TLC Rf=0.41 in 3% methanol in DCM. ¹H NMR (DMSO): 12.30 (s, 1H), 7.25 (m, 3H), 6.92 (m, 3H), 6.82 (dd, 1H, J=8.6, 2.4 Hz), 4.18 (d, 1H, J=12.3 Hz), 3.76 (m, 6H), 3.42 (dd, 1H, J=12.6, 2.4 Hz), 3.27 (s, 1H), 2.50 (m, 1H), 1.89 (m, 1H), 1.59 (m, 2H), 1.40 (m, 1H), 1.23 (m, 1H), 0.99 (m, 3H); MS m/z 322 (M−44, decarbonylation).

PREPARATION 146

[6-Methoxy-10-(4-methoxy-phenyl)-1,2,3,4,4a,9,10,10a-octahydro-phenanthren-9-yl]-methanol

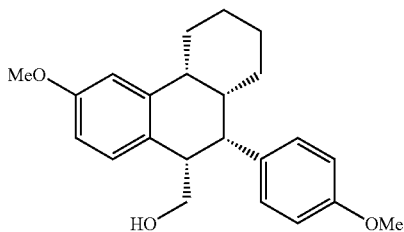

Preparation 146 is prepared from preparation 140 in a manner similar to preparation 142. TLC Rf=0.17 in 4:1 hexanes:ethyl acetate. ¹H NMR (CDCl₃): 7.33 (d, 1H, J=8.4 Hz), 7.00 (m, 3H), 6.81 (m, 3H), 3.93 (dd, 1H, J=10.8, 5.9 Hz), 3.87 (s, 3H), 3.78 (m, 4H), 3.56 (t, 1H, J=6.4 Hz), 3.37 (dd, 1H, J=12.6, 5.9 Hz), 3.05 (m, 1H), 2.52 (m, 1H), 2.28 (m, 1H), 1.79 (m, 1H), 1.39 (m, 4H), 1.05 (m, 2H).

PREPARATION 147

[6-Methoxy-10-(4-methoxy-phenyl)-1,2,3,4,4a,9,10,10a-octahydro-phenanthren-9-yl]-acetonitrile

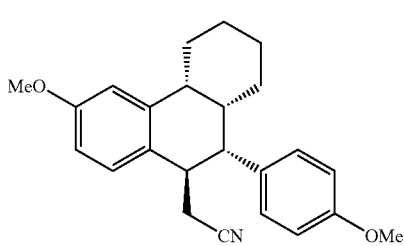

Combine toluene-4-sulfonic acid 6-methoxy-10-(4-methoxy-phenyl)-1,2,3,4,4a,9,10,10a-octahydro-phenanthren-9-ylmethyl ester (0.224 g, 0.44 mmol), KCN (0.172 g, 2.65 mmol), and DMF (4 mL), and stir under nitrogen atmosphere at 100° C. After 2 hours, add ethyl acetate and water. Separate the organic phase and wash with brine. Dry the organic phase with anhydrous sodium sulfate and flash chromatograph using 0% to 20% ethyl acetate/hexanes to yield the titled compound (0.139 g, 87%) as a white foam. TLC Rf=0.46 in 4:1 hexanes:ethyl acetate. ¹H NMR (CDCl₃): 7.31 (m, 1H), 7.24 (d, 2H, J=8.8 Hz), 6.96 (m, 3H), 6.84 (dd, 1H, J=8.4, 2.6 Hz), 3.86 (m, 6H), 3.59 (m, 1H), 3.34 (s, 1H), 3.18 (dd, 1H, J=12.3, 3.1 Hz), 2.90 (dd, 1H, J=17.2, 4.4 Hz), 2.51 (m, 2H), 1.98 (m, 1H), 1.66 (m, 2H), 1.48 (m, 2H), 1.14 (m, 3H).

PREPARATION 148

1-[6-Methoxy-10-(4-methoxy-phenyl)-1,2,3,4,4a,9,10,10a-octahydro-phenanthren-9-ylmethyl]-pyrrolidine

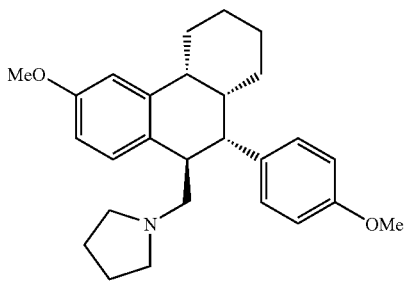

Combine toluene-4-sulfonic acid 6-methoxy-10-(4-methoxy-phenyl)-1,2,3,4,4a,9,10,10a-octahydro-phenanthren-9-ylmethyl ester (0.087 g, 0.175 mmol), pyrrolidine (0.09 mL, 1.05 mmol), and benzene (5 mL), and reflux under nitrogen atmosphere. After 18 hours, concentrate reaction under vacuum then add ethyl acetate and wash with sodium bicarbonate solution (aq). Separate the organic phase and wash with brine. Dry the organic phase with anhydrous sodium sulfate and flash chromatograph using 2% to 4% (2M NH₃ methanol)/methylene chloride to yield the titled compound (0.060 g, 86%) as a white solid. TLC Rf=0.25 in 4% 2M NH₃ methanol:DCM. ¹H NMR (CDCl₃): 7.95 (d, 1H, J=8.4 Hz), 7.24 (d, 2H, J=8.4 Hz), 6.91 (m, 3H), 6.79 (dd, 1H, J=8.6, 2.4 Hz), 3.85 (s, 6H), 3.34 (t, 1H, J=9.2 Hz), 3.22 (s, 1H), 3.07 (dd, 1H, J=11.7, 3.3 Hz), 2.74 (dd, 1H, J=12.3, 7.5 Hz), 2.42 (m, 4H), 2.20 (m, 2H), 1.89 (m, 1H), 1.66 (m, 6H), 1.43 (m, 2H), 1.17 (m, 3H); MS m/z 406 (M+1).

PREPARATION 149

9-Ethyl-6-methoxy-10-(4-methoxy-phenyl)-1,2,3,4,4a,9,10,10a-octahydro-phenanthrene

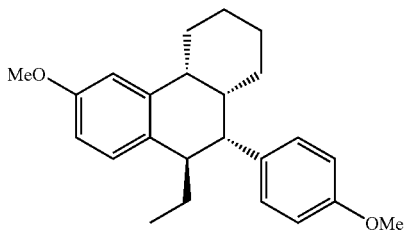

Combine toluene-4-sulfonic acid 6-methoxy-10-(4-methoxy-phenyl)-1,2,3,4,4a,9,10,10a-octahydro-phenanthren-9-ylmethyl ester (0.151 g, 0.30 mmol), methyl magnesium bromide (0.46 mL, 1.40 mmol), Li₂CuCl₄ (150 uL), and tetrahydrofuran (3 mL), and stir under nitrogen atmosphere. After 18 hours, concentrate reaction under vacuum and flash chromatograph using 0% to 10% ethyl acetate/hexanes to yield the titled compound (0.085 g, 81%) as a white foam. TLC Rf=0.60 in 8:1 hexanes:ethyl acetate. ¹H NMR (CDCl$_3$): 7.32 (s, 1H), 7.24 (d, 2H, J=8.4 Hz), 6.94 (m, 3H), 6.81 (dd, 1H, J=8.4, 2.6 Hz), 3.86 (m, 6H), 3.42 (m, 1H), 3.23 (s, 1H), 3.08 (dd, 1H, J=12.1, 3.3 Hz), 2.49 (d, 1H, J=13.7 Hz), 1.93 (m, 2H), 1.67 (m, 1H), 1.57 (m, 2H), 1.44 (d, 2H, J=8.8 Hz), 1.19 (m, 3H), 0.62 (t, 3H, J=7.3 Hz).

PREPARATION 150

6-Benzyloxy-10-(4-benzyloxy-phenyl)-1,2,3,4,40, 10,10a-octahydro-phenanthrene-9-carboxylic acid benzyl ester

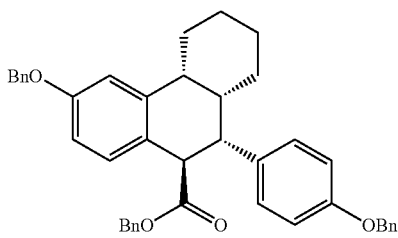

Combine 6-hydroxy-10-(4-hydroxy-phenyl)-1,2,3,4,4a,9, 10,10a-octahydro-phenanthrene-9-carboxylic acid (0.627 g, 1.71 mmol), benzyl bromide (0.73 mL, 6.67 mmol), potassium carbonate (0.992 g, 7.18 mmol), TBAI (2.46 g, 6.67 mmol), and DMF (40.0 mL), and reflux under nitrogen atmosphere. After 18 hours, add ethyl acetate and water, separated the organic phase and wash 4× with brine. Dry the organic phase over anhydrous sodium sulfate. Concentrate the organic phase under vacuum and flash chromatograph using 0% to 20% ethyl acetate/hexanes to yield the titled compound (0.550 g, 53%) as a white solid. TLC Rf=0.17 in 8:1 hexanes: ethyl acetate. $^1$H NMR (CDCl$_3$): 7.44 (m, 10H), 7.27 (m, 5H), 7.18 (d, 1H, J=8.4 Hz), 7.08 (m, 3H), 6.96 (d, 2H, J=8.4 Hz), 6.81 (dd, 1H, J=8.6, 2.4 Hz), 5.06 (m, 6H), 4.41 (d, 1H, J=12.3 Hz), 3.58 (dd, 1H, J=12.3, 2.6 Hz), 3.36 (s, 1H), 2.47 (d, 1H, J=14.1 Hz), 2.02 (m, 1H), 1.70 (m, 1H), 1.46 (m, 2H), 1.11 (m, 4H).

PREPARATION 151

[6-Benzyloxy-10-(4-benzyloxy-phenyl)-1,2,3,4,4a, 10,10a-octahydro-phenanthrene-9-yl]-methanol

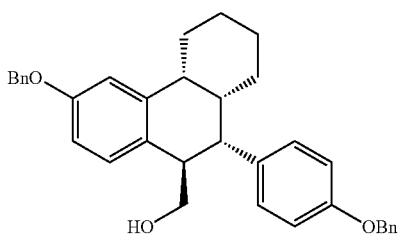

Combine 6-benzyloxy-10-(4-benzyloxy-phenyl)-1,2,3,4, 4a,9,10,10a-octahydro-phenanthrene-9-carboxylic acid benzyl ester (0.129 g, 0.212 mmol), lithium aluminum hydride (0.024 g, 0.64 mmol), and tetrahydrofuran (4 mL), and stir under nitrogen atmosphere. After 2 hours, quench reaction by adding reaction to a stirred solution of Rochelle's salt (Na K Tartrate) and ethyl acetate. After several hours, separate the organic phase and wash with Brine. Dry the organic phase with anhydrous sodium sulfate and flash chromatograph using 5% to 50% ethyl acetate/hexanes to yield the titled compound (0.071 g, 66%) as a white solid. TLC Rf=0.43 in 1:1 hexanes:ethyl acetate. $^1$H NMR (CDCl$_3$): 7.42 (m, 11H), 7.25 (d, 2H, J=8.8 Hz), 7.06 (s, 1H), 7.00 (d, 2H, J=8.8 Hz), 6.91 (dd, 1H, J=8.6, 2.4 Hz), 5.11 (m, 4H), 4.74 (s, 1H), 4.06 (dd, 1H, J=11.2, 3.3 Hz), 3.63 (dd, 1H, J=11.2, 2.4 Hz), 3.33 (m, 3H), 2.44 (d, 1H, J=14.1 Hz), 1.92 (m, 1H), 1.63 (m, 2H), 1.43 (m, 2H), 1.11 (m, 2H).

PREPARATION 152

6-Methoxy-9-methoxymethyl-10-(4-methoxy-phenyl)-1,2,3,4,4a,9,10,10a-octahydro-phenanthrene

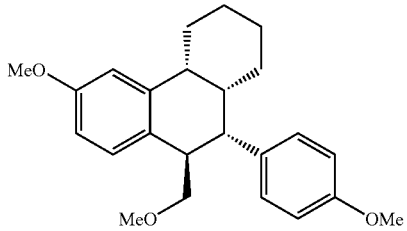

Combine [6-methoxy-10-(4-methoxy-phenyl)-1,2,3,4,4a, 9,10,10a-octahydro-phenanthren-9-yl]-methanol (0.084 g, 0.24 mmol), NaH (0.014 mg, 0.29 mmol), and DMF (3.0 mL) and stir under nitrogen atmosphere at −10° C. After 1 hour, add MeI (50 uL, 0.072 mmol) and stir at room temperature for 18 hours. Concentrate reaction under vacuum then add ethyl acetate and water, separated the organic phase and wash 2× with brine. Dry the organic phase over anhydrous sodium sulfate. Concentrate the organic phase under vacuum and flash chromatograph using 0% to 25% ethyl acetate/hexanes to yield the titled compound (0.057 g, 65%) as a white solid. TLC Rf=0.40 in 3:1 hexanes:ethyl acetate. $^1$H NMR (CDCl$_3$): 7.58 (d, 1H, J=8.8 Hz), 7.25 (d, 2H, J=8.8 Hz), 6.93 (m, 3H), 6.81 (dd, 1H, J=8.4, 2.6 Hz), 3.85 (m, 6H), 3.66 (m, 1H), 3.38 (m, 2H), 3.23 (m, 4H), 3.11 (dd, 1H, J=11.9, 3.1 Hz), 2.48 (d, 1H, J=13.7 Hz), 1.92 (m, 1H), 1.42 (m, 2H), 1.18 (m, 3H), 1.77 (m, 2H).

PREPARATION 153

1-[6-Methoxy-10-(4-methoxy-phenyl)-1,2,3,4,4a,9, 10,10a-octahydro-phenanthren-9-yl]-ethanone

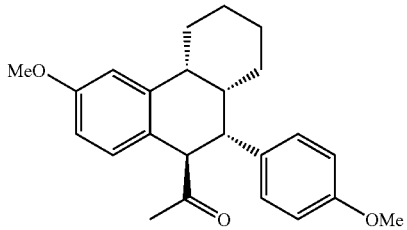

Combine 6-methoxy-10-(4-methoxy-phenyl)-1,2,3,4,4a, 9,10,10a-octahydro-phenanthren-9-carboxylic acid methyl ester (0.252 g, 0.662 mmol), methyl magnesium Bromide (1.76 mL, 5.3 mmol), and tetrahydrofuran (8 mL), and reflux under nitrogen atmosphere. After 18 hours, cool the reaction to room temperature and add ethyl acetate, wash with sat ammonium chloride solution (aq), then brine. Concentrate, and chromatograph eluting with 0% to 20% ethyl acetate/hexanes to yield the titled compound (0.068 g, 28%) as a white solid. TLC Rf=0.19 in 8:1 hexanes:ethyl acetate. $^1$H NMR (CDCl$_3$): 7.26 (d, 2H, J=8.8 Hz), 7.04 (s, 1H), 7.01 (d, 1H, J=8.8 Hz), 6.91 (d, 2H, J=7.9 Hz), 6.77 (dd, 1H, J=8.4, 2.6 Hz), 4.31 (d, 1H, J=12.8 Hz), 3.84 (m, 6H), 3.37 (m, 2H), 2.53 (d, 1H, J=14.1 Hz), 2.05 (m, 1H), 1.92 (s, 3H), 1.74 (m, 1H), 1.62 (m, 2H), 1.47 (m, 2H), 1.31 (m, 2H).

PREPARATION 154

6-Methoxy-10-(4-methoxy-phenyl)-9-methyl-1,2,3,4,4a,10a-hexahydro-phenanthrene

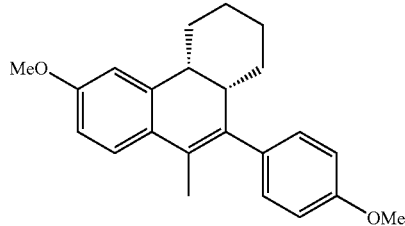

Combine trifluoro-methanesulfonic acid 6-methoxy-10-(4-methoxy-phenyl)-1,2,3,4,4a,10a-hexahydro-phenanthren-9-yl ester (0.523 g, 1.12 mmol), Pd-tetrakis (45.0 mg, 0.04 mmol), and tetrahydrofuran (10.0 mL), and stir under nitrogen atmosphere at 0° C. After 15 minutes, add dimethylzinc (3.5 mL, 3.44 mmol) dropwise. Allow the reaction to warm to room temperature and stir for 18 hours, then heat reaction at 40° C. for 3 hours. Add ethyl acetate and water. Wash the organic phase with brine, dry over anhydrous sodium sulfate, concentrate, and chromatograph eluting with 0% to 20% ethyl acetate/hexanes to yield the titled compound (0.224 g, 60%) as a white solid. TLC Rf=0.30 in 5:1 hexanes: ethyl acetate. $^1$H NMR (CDCl$_3$): 7.32 (s, 1H), 7.20 (d, 2H, J=8.8 Hz), 6.95 (m, 3H), 6.79 (m, 1H), 3.88 (m, 6H), 3.21 (m, 1H), 2.46 (m, 2H), 1.97 (s, 3H), 1.74 (m, 1H), 1.55 (m, 3H), 1.38 (m, 1H), 1.15 (m, 2H).

PREPARATION 155

6-Methoxy-10-(4-methoxy-phenyl)-9-methyl-1,2,3,4,4a,9,10,10a-octahydro-phenanthrene

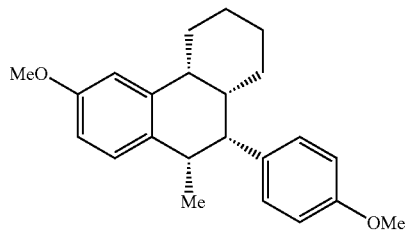

Combine 6-methoxy-10-(4-methoxy-phenyl)-9-methyl-1,2,3,4,4a,10a-hexahydro-phenanthrene (0.116 g, 0.347 mmol), Pd-Black (14.7 mg, 0.139 mmol) and acetic acid/methanol/tetrahydrofuran (1.0 mL, 10.0 mL, 3.0 mL) at 50 psi Hydrogen pressure. After 18 hours, filter off the Pd catalyst over celite eluting with ethyl acetate. Concentrate and flash chromatograph with 0% to 10% ethyl acetate/hexanes to yield the titled compound (0.108 g, 93%) as a clear oil. TLC Rf=0.30 in 5:1 hexanes:ethyl acetate. $^1$H NMR (CDCl$_3$): 7.26 (d, 1H, J=8.4 Hz), 7.03 (m, 3H), 6.83 (m, 3H), 3.90 (s, 3H), 3.83 (s, 3H), 3.36 (m, 2H), 3.12 (m, 1H), 2.52 (m, 1H), 2.35 (m, 1H), 1.87 (m, 1H), 1.51 (m, 4H), 1.30 (m, 2H), 1.18 (d, 3H, J=6.6 Hz).

PREPARATION 156

6-Methoxy-5-nitro-2,3,4,4a,10,10a-hexahydro-1H-phenanthren-9-one

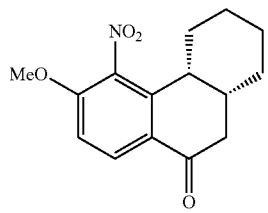

Combine 6-methoxy-2,3,4,4a,10,10a-hexahydro-1H-phenanthren-9-one (0.936 g, 4.06 mmol), Ac$_2$O (5.0 mL), and a solution of 90% HNO$_3$/acetic acid (0.8 mL), and stir under Nitrogen atmosphere at 0° C. After 3 hours, add ethyl acetate. Wash the ethyl acetate with sodium bicarbonate solution and then brine, dry over sodium sulfate, and concentrate in vacuum. Flash chromatograph using dichloromethane (isocratic) to yield the titled compound (0.378 g, 34%) as a solid. TLC Rf=0.25 in dichlormethane. $^1$H NMR (CDCl$_3$): 8.22 (d, 1H, J=8.8 Hz), 7.04 (d, 1H, J=8.8 Hz), 3.99 (s, 3H), 2.96 (m, 2H), 2.49 (m, 2H), 1.63 (m, 8H).

PREPARATION 157

6-Methoxy-10-(4-methoxy-phenyl)-5-nitro-2,3,4,4a,10,10a-hexahydro-1H-phenanthren-9-one

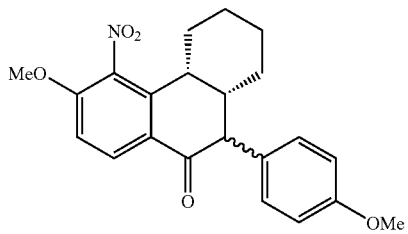

Combine 6-Methoxy-5-nitro-2,3,4,4a,10,10a-hexahydro-1H-phenanthren-9-one (0.377 g, 1.37 mmol), 4-bromoanisole (0.258 g, 1.37 mmol), palladium acetate (15.5 mg, 0.07 mmol), t-butyl phosphine (0.042 g, 0.208 mmol), sodium t-butoxide (0.145 g, 1.51 mmol), tetrahydrofuran (12.0 mL), and stir under nitrogen atmosphere at 80° C. in a glass bomb. After 18 hours, quench reaction with acetic acid (5 mL) in a glove box and extract with ethyl acetate. Wash the ethyl acetate with sodium bicarbonate solution and then brine, dry over sodium sulfate, and concentrate in vacuum. Flash chromatograph using 0% to 20% ethyl acetate/hexanes to yield the titled compound (0.455 g, 87%) as a yellow foam. TLC Rf=0.16 in 6:1 hexanes:ethyl acetate. $^1$H NMR (CDCl$_3$): 8.23

(d, 1H, J=8.8 Hz), 7.06 (m, 3H), 6.92 (m, 2H), 4.01 (m, 4H), 3.83 (s, 3H), 3.10 (dt, 1H, J=8.4, 4.3 Hz), 2.76 (m, 1H), 1.82 (m, 4H), 1.47 (m, 4H).

PREPARATION 158

6-Methoxy-10-(4-methoxy-phenyl)-5-nitro-1,2,3,4,4a,10,10a-octahydro-phenanthren-9-ol

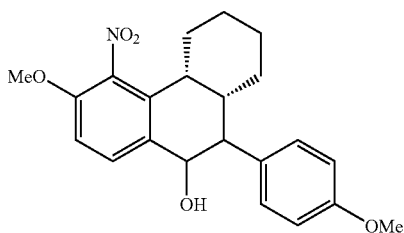

Combine 6-methoxy-10-(4-methoxy-phenyl)-5-nitro-2,3,4,4a,10,10a-hexahydro-1H-phenanthren-9-one (455.0 mg, 1.19 mmol), sodium borohydride (130.0 mg, 3.46 mmol), ethanol (7.0 mL), tetrahydrofuran (2.0 mL), stir, and reflux under a nitrogen atmosphere. After 3 hours, cool to ambient temperature, and concentrate in vacuo. Add ethyl acetate to reaction mixture, wash with sat ammonium chloride solution (aq), brine, and dry over sodium sulfate. Concentrate to yield the titled compound (378.0 mg, 83%). TLC Rf=0.18 in 2:1 hexanes:ethyl acetate. $^1$H NMR (CDCl$_3$): 7.68 (m, 1H), 7.26 (m, 1H), 7.08 (m, 1H), 6.94 (m, 2H), 6.81 (m, 1H), 3.89 (m, 6H), 3.30 (m, 1H), 2.90 (m, 1H), 2.51 (m, 2H), 1.64 (m, 8H).

PREPARATION 159

6-Methoxy-10-(4-methoxy-phenyl)-5-nitro-1,2,3,4,4a,10a-hexahydro-phenanthrene

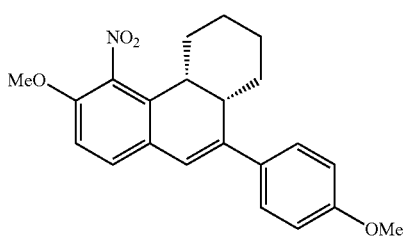

Combine 6-methoxy-10-(4-methoxy-phenyl)-5-nitro-1,2,3,4,4a,9,10,10a-octahydro-phenanthren-9-ol (378.6 mg, 0.987 mmol), p-toluene sulfonic acid (38.0 mg, 0.197 mmol), toluene (8 mL), stir, and reflux under nitrogen atmosphere. After 1 hour, cool reaction to ambient temperature, add ethyl acetate, wash sat sodium bicarbonate solution (aq), and then with brine, dry over sodium sulfate, and concentrate in vacuum. Flash chromatograph using 0% to 30% ethyl acetate/hexanes to yield the titled compound (234.5 mg, 68%) as a clear oil. TLC Rf=0.40 in 2:1 hexanes:ethyl acetate. $^1$H NMR (CDCl$_3$): 7.25 (d, 2H, J=8.4 Hz), 6.91 (d, 2H, J=8.4 Hz), 6.67 (d, 1H, J=8.4 Hz), 6.58 (d, 1H, J=8.4 Hz), 6.37 (d, 1H, J=2.6 Hz), 3.88 (m, 6H), 3.18 (s, 1H), 2.90 (m, 1H), 2.19 (d, 1H, J=14.1 Hz), 1.60 (m, 4H), 1.33 (m, 2H), 0.99 (m, 1H).

PREPARATION 160

3-Methoxy-9-(4-methoxy-phenyl)-4b,5,6,7,8,8a,9,10-octahydro-phenanthren-4-ylamine

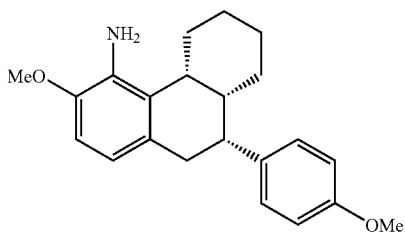

Preparation 160 is prepared from preparation 159 in a manner similar to preparation 9. (0.689 g, 46%) TLC Rf=0.55 in 2:1 hexanes:ethyl acetate. $^1$H NMR (CDCl$_3$): 7.24 (d, 2H, J=8.8 Hz), 6.87 (d, 2H, J=8.8 Hz), 6.70 (m, 2H), 3.86 (m, 7H), 3.31 (m, 1H), 3.09 (m, 2H), 2.90 (m, 1H), 2.33 (m, 2H), 1.53 (m, 6H).

EXAMPLE 1

9-(4-Hydroxy-phenyl)-4b,5,6,7,8,8a,9,10-octahydro-phenanthren-3-ol

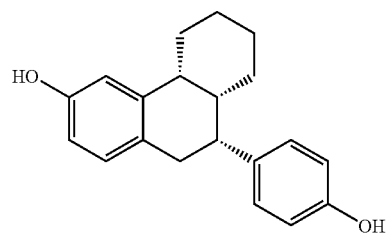

Combine 6-methoxy-10-(4-methoxy-phenyl)-1,2,3,4,4a,9,10,10a-octahydro-phenanthrene (132.1 mg, 0.41 mmol), methylene chloride (4.0 mL), boron tribromide (0.16 mL, 1.64 mmol) at 0° C., and stir under a nitrogen atmosphere. After 1.5 hours, add ethyl acetate to reaction mixture, quench reaction with sat ammonium chloride solution (aq). Wash organic layer with brine, dry over sodium sulfate, and concentrate in vacuo. Flash chromatograph to yield the titled compound (86.7 mg, 72%) as a white solid. $^1$H NMR (DMSO): 9.15 (s, 1H), 9.00 (s, 1H), 7.08 (d, 2H, J=8.8 Hz), 6.93 (d, 1H, J=8.4 Hz), 6.70 (m, 3H), 6.52 (dd, 1H, J=8.4, 2.2 Hz), 3.05 (m, 3H), 2.65 (m, 1H), 2.34 (d, 1H, J=12.8 Hz), 1.88 (m, 1H), 1.55 (m, 2H), 1.37 (m, 1H), 1.05 (m, 4H); MS m/z 293 (M−1).

EXAMPLEs 1A and 1B

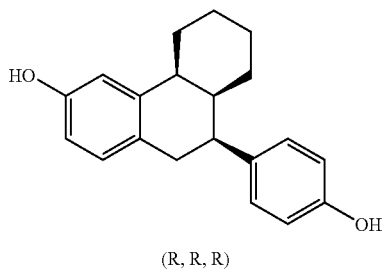
(R, R, R)

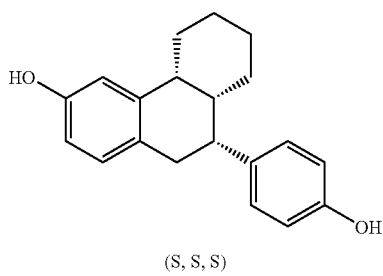
(S, S, S)

Using standard HPLC equipment, chromatograph the product of Example 1 (86.7 mg, Chiralpak AD 0.46×25 cm column, 85% Heptane/Ethanol eluent, 1.0 mL/min, 225 nm). Concentration of pure fractions yields (R,R,R) (33.0 mg, 100% ee, 6.3 min) and (S,S,S) (48.0 mg, 100% ee, 9.6 min) as white solids.

EXAMPLE 2

4-(4-Hydroxy-phenyl)-2,3,3a,4,5,9b-hexahydro-1H-cyclopenta[a]naphthalen-8-ol

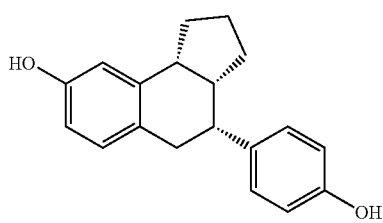

Example 2 is prepared from preparation 18 in a manner similar to example 1. $^1$H NMR (DMSO): 9.11 (s, 1H), 8.98 (s, 1H), 7.06 (d, 2H, J=8.4 Hz), 6.86 (d, 1H, J=7.9 Hz), 6.67 (d, 2H, J=7.9 Hz), 6.53 (s, 1H), 6.46 (m, 1H), 2.89 (m, 2H), 2.49 (m, 2H), 2.07 (m, 2H), 1.36 (m, 4H), 1.16 (m, 1H). MS m/z (279 (M−1).

Separate example 2 into its enantiomers using the conditions described for the separation of example 1 into its enantiomers (examples 1A and 1B).

EXAMPLE 3

4-(4-Hydroxy-phenyl)-2,3,3a,4,5,9b-hexahydro4H-cyclopenta[a]naphthalene-6,8-diol

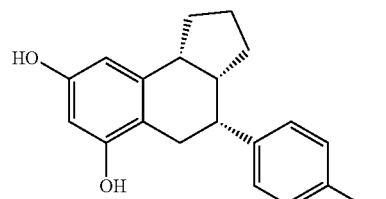

Example 3 is prepared from preparation 27 in a manner similar to example 1. $^1$H NMR (DMSO-d$_6$) 9.09(s, 1H), 8.98 (s, 1H), 8.77 (s, 1H), 7.06 (d, J=8.4 HZ, 2H), 6.66 (d, J=8.4 Hz, 2H), 6.06 (s, 1H), 6.02 (s, 1H), 3.15 (m, 2H), 2.85 (m, 1H), 2.64(dd, J=14.4, 14, 1H), 2.35 (m, 1H), 2.05 (m, 1H), 1.5-1.1 (m, 5H). MS m/z 295 (M−1).

Separate example 3 into its enantiomers using the conditions described for the separation of example 1 into its enantiomers (examples 1A and 1B).

EXAMPLE 4

4-(4-Hydroxy-phenyl)-1,3,3a,4,5,9b-hexahydro-naphtho[1,2-c]furan-8-ol

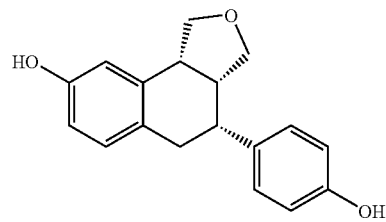

Example 4 is prepared from preparation 36 in a manner similar to example 1. TLC Rf=0.24 in 1:1 hexanes:ethyl acetate. $^1$H NMR (d-methanol): 7.13 (d, 2H, J=8.4 Hz), 6.99 (d, 1H, J=8.4 Hz), 6.77 (d, 2H, J=8.8 Hz), 6.62 (m, 2H), 4.17 (m, 1H), 3.68 (t, 1H, J=8.8 Hz), 3.55 (m, 3H), 3.04 (m, 3H), 2.69 (m, 1H).

Separate example 4 into its enantiomers using the conditions described for the separation of example 1 into its enantiomers (examples 1A and 1B).

EXAMPLE 5

9-(3-Fluoro-4-hydroxy-phenyl)-4b,5,6,7,8,80,10-octahydro-phenanthren-3-ol

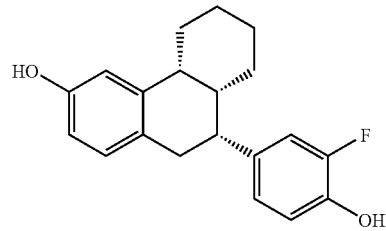

Example 5 is prepared from preparation 40 in a manner similar to example 1. ¹H NMR (d-methanol): 6.95 (m, 5H), 6.61 (m, 1H), 3.12 (m, 3H), 2.78 (dd, 1H, J=14.5, 3.5 Hz), 2.51 (d, 1H, J=14.1 Hz), 1.73 (m, 1H), 1.63 (m, 1H), 1.46 (m, 1H), 1.19 (m, 5H); MS m/z 313 (M+1), 311 (M−1).

EXAMPLE 6

9-(4-Hydroxy-phenyl)-4b,5,6,7,8,8a,9,10-octahydro-phenanthren-4-ol

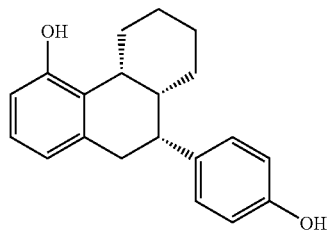

Example 6 is prepared from preparation 53 in a manner similar to example 1. ¹H NMR (d-methanol): 7.1 (d, 2H, J=6.4 Hz), 6.9 (t, 1H, J=6.9 Hz), 6.7 (m, 3H), 6.6 (d, 1H, J=7.9 Hz), 3.3 (m, 2H), 3.1 (m, 1H), 3.0 (m, 1H), 2.7 (dd, 1H, J=11.4, J=5.3 Hz), 2.1 (m, 1H), 1.5 (m, 2H), 1.3 (m, 3H), 1.1 (m, 2H).

Separate example 6 into its enantiomers using the conditions described for the separation of example 1 into its enantiomers (examples 1A and 1B).

EXAMPLE 7

9-(4-Hydroxy-phenyl)-4b,5,6,7,8,8a,9,10-octahydro-phenanthren-2-ol

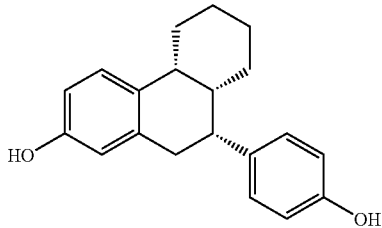

Example 7 is prepared from preparation 63 in a manner similar to example 1. ¹H ¹H NMR (DMSO): 9.18 (s, 1H), 9.02 (s, 1H), 7.17 (d, 1H, J=8.8 Hz), 7.12 (d, 2H, J=8.5 Hz), 6.71 (d, 2H, J=8.5 Hz), 6.60 (dd, 1H, J=8.8 and 2.4 Hz), 6.58 (d, 1H, J=2.4 Hz), 3.08 (m, 3H), 2.69 (dd, 1H, J=15.8 and 4.8 Hz), 2.42 (m, 1H), 1.91 (m, 1H), 1.65-1.55 (m, 2H), 1.38 (m, 1H), 1.16 (m, 1H), 1.02 (m, 3H).

Separate example 7 into its enantiomers using the conditions described for the separation of example 1 into its enantiomers (examples 1A and 1B).

EXAMPLE 8

9-(4-Hydroxy-phenyl)-6,6-dimethyl-4b,5,6,7,8,8a,9,10-octahydro-phenanthren-3-ol

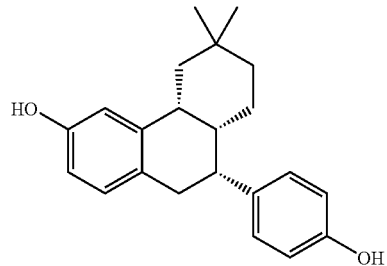

Example 8 is prepared from preparation 74 in a manner similar to example 1. (0.162 g, 46%): ¹H NMR (DMSO) δ 9.15 (s, 1H), 8.92 (s, 1H) 7.11-7.09 (d, 2H), 6.93-6.90 (d, 1H), 6.81 (s, 1H), 6.72-6.69 (d, 2H), 6.52-6.49 (dd, 1H), 3.17-3.12 (m, 2H), 3.0-2.96 (d, 1H), 2.63-2.57 (dd, 1H), 2.21-2.17 (d, 1H), 1.87-1.81 (m, 1H), 1.57-1.52 (dd, 1H), 1.28-1.21 (t, 2H), 1.08-1.03 (t, 2H), 0.86 (s, 3H), 0.44 (s, 3H), Mass spectrum (apci neg) m/z=321.3 (M−H), HPLC (25 to 95) R$_t$ (Purity at 220 nm)=2.82 min (100%).

Separate example 8 into its enantiomers using the conditions described for the separation of example 1 into its enantiomers (examples 1A and 1B).

EXAMPLE 9

9-(4-Hydroxy-phenyl)-7,7-dimethyl-4b,5,6,7,8,8a,9,10-octahydro-phenanthren-3-ol

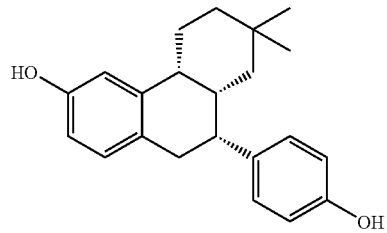

Example 9 is prepared from preparation 86 in a manner similar to example 1. (0.055 g, 20%): ¹H NMR (CDCl₃) δ 7.19-7.16 (d, 2H), 7.04-7.02 (d, 1H), 6.87 (s, 1H), 6.83-6.81 (d, 2H) 6.66-6.64 (dd, 1H), 4.56 (s, 1H), 4.49 (s, 1H), 3.15-3.13 (m, 3H), 2.85-2.82 (d, 1H), 2.25-2.22 (d, 2H), 1.97-1.89 (m, 1H), 1.3-1.25 (m, 2H), 1.11-1.07 (m, 2H), 0.82 (s, 3H), 0.73 (3, H), Mass spectrum (apci neg) m/z=321.3 (M−H), HPLC (5 to 95) R$_t$ (Purity at 220 nm)=3.2 min (100%).

Separate example 9 into its enantiomers using the conditions described for the separation of example 1 into its enantiomers (examples 1A and 1B).

EXAMPLE 10

4-(4-Hydroxy-phenyl)-2,3,3a,4,5,9b-hexahydro-1H-cyclopenta[a]naphthalene-6,9-diol

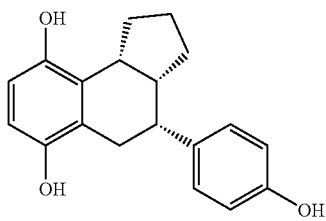

Example 10 is prepared from preparation 97 in a manner similar to example 1. (0.067 g, 40%): $^1$H NMR (CDCl$_3$) δ 7.19-7.17 (d, 2H), 6.82-6.79 (d, 2H), 6.55-6.54 (d, 2H), 4.59 (s, 1H), 4.37 (s, 1H), 3.55-3.49 (m, 1H), 3.08-3.02 (m, 1H), 2.98-2.93 (m, 1H), 2.78-2.71 (m, 1H), 2.65-2.57 (m, 1H), 2.43-2.35 (m, 1H), 1.48-1.25 (m, 5H).

Separate example 10 into its enantiomers using the conditions described for the separation of example 1 into its enantiomers (examples 1A and 1B).

EXAMPLE 11

6-(4-Chloro-phenyl)-4-(4-hydroxy-phenyl)-2,3,3a,4,5,9b-hexahydro-1H-cyclopenta[a]naphthalen-8-ol

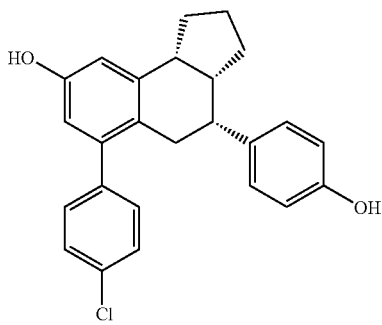

Example 11 is prepared from preparation 102 in a manner similar to Example 1. $^1$H NMR (CDCl$_3$): 7.34 (d, J=7.9 Hz, 2H), 7.25 (d, J=10.1 Hz, 2H), 7.04 (d, J=8.4 Hz, 2H), 6.74 (s, 1H), 6.72 (d, J=6.2 Hz, 2H), 6.56 (s, 1H), 3.4 (m, 1H), 2.95 (m, 1H), 2.8 (dd, J=15 and 13 Hz, 1H) 2.55 (m, 2H), 2.25 (m, 1H), 1.7-1.2 (m, 5H). MS m/z 389 (M−1).

EXAMPLE 12

8-Hydroxy-4-(4-hydroxy-phenyl)-2,3,3a,4,5,9b-hexahydro-1H-cyclopenta[a]naphthalene-6-carboxylic acid methyl ester

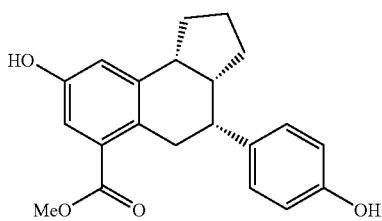

Example 12 is prepared from preparation 103 in a manner similar to Example 1. $^1$H NMR (DMSO-d$_6$) 9.43(s, 1H), 9.13 (s, 1H), 7.04 (d, J=7.9 Hz, 2H), 6.95 (s, 1H), 6.78 (s, 1H), 6.67 (d, J=8.3 Hz, 2H), 3.75 (s, 3H), 3.0 (m, 1H), 2.85 (m, 2H), 2.43(m, 2H), 2.1 (m, 1H), 1.5-1.1 (m, 5H). MS m/z 337 (M−1).

EXAMPLE 13

8-Hydroxy-4-(4-hydroxy-phenyl)-2,3,3a,4,5,9b-hexahydro-1H-cyclopenta[a]naphthalene-6-carboxylic acid

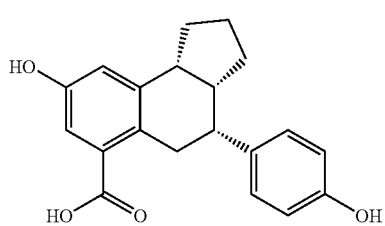

Combine 8-Hydroxy-4-(4-hydroxy-phenyl)-2,3,3a,4,5,9b-hexahydro-1H-cyclopenta[a]naphthalene-6-carboxylic acid methyl ester (0.013 g, 0.038 mmol), ethanol (3 ml), and NaOH (1.5 ml, 2N) and heat at 45° C. for 1.5 hours. Acidify with 1 N HCl and extract with ethyl acetate. Wash 1× with water, dry over anhydrous sodium sulfate and concentrate in vacuo to yield the titled compound (0.010 g, 84%) as a white residue. $^1$H NMR (CD$_3$OD) 7.1 (d, J=7.5 Hz, 2H), 7.08 (s, 1H), 6.8 (s, 1H), 6.7 (d, J=7.5 Hz, 2H), 3.4 (m, 1H), 3.15 (m, 1H), 3.0 (m, 2H), 2.55(m, 1H) 2.2 (m, 1H), 1.6-1.2. MS m/z 323 (M−1).

EXAMPLE 14

6-Bromomethyl-4-(4-hydroxy-phenyl)-2,3,3a,4,5,9b-hexahydro-1H-cyclopenta[a]naphthalen-8-ol

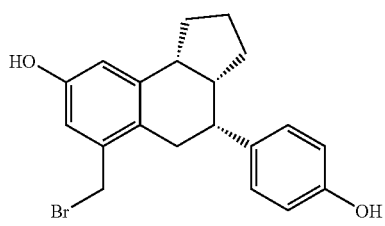

Combine [8-Methoxy-4-(4-methoxy-phenyl)-2,3,3a,4,5,9b-hexahydro-1H-cyclopenta[a]naphthalen-6-yl]-methanol (0.025 g, 0.074 mmol), boron tribromide (0.11 g, 0.44 mmol), and methylene chloride (1.5 ml) and stir 3 hours. Add water, ethyl acetate and 1N HCl. Rinse organic layer with water, dry over anhydrous sodium sulfate and remove solvent to yield the titled compound (0.023 g, 84%). $^1$H NMR (DMSO-d$_6$) 9.18(s, 1H), 9.14 (s, 1H), 7.1 (d, J=7.9 Hz, 2H), 6.7 (d, J=7.9 Hz, 2H), 6.62 (s, 1H), 6.56 (s, 1H), 4.68 (d, J=10.1 Hz, 1H), 4.58 (d, J=9.6 Hz, 1H), 3.4 (m, 1H presumed), 2.95 (m, 1H), 2.8 (m, 2H), 2.45(m, 1H) 2.1 (m, 1H), 1.6-1.1 (m, 5H). MS m/z 371 (M−2).

EXAMPLE 15

[8-Hydroxy-4-(4-hydroxy-phenyl)-2,3,3a,4,5,9b-hexahydro-1H-cyclopenta[a]naphthalen-6-yl]-acetonitrile

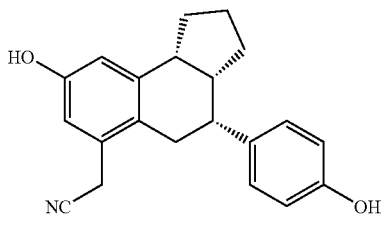

Combine 6-Bromomethyl-4-(4-hydroxy-phenyl)-2,3,3a,4,5,9b-hexahydro-1H-cyclopenta[a]naphthalen-8-ol (0.037 g, 0.1 mmol), KCN (0.010 g, 0.15 mmol), and 18-crown-6 (0.043 g, 0.16 mmol) and heat at 80° C. for 2 hours. Cool, add ice and extract with ethyl acetate. Wash organic layer with sodium bicarbonate solution sat., then water. Dry over anhydrous sodium sulfate and concentrate to a residue which yields, after separation on silica gel with 33% EtOAC/hexanes, the titled compound (0.022 g, 70%). $^1$H NMR (DMSO-d$_6$) 9.27(s, 1H), 9.18 (s, 1H), 7.13 (d, J=8.4 Hz, 2H), 6.73 (d, J=7.9 Hz, 2H), 6.66 (s, 1H), 6.59 (s, 1H), 3.95 (s, 2H), 3.4 (m, 1H presumed), 3.0 (m, 1H), 2.76 (m, 1H), 2.65 (m, 1H), 2.45(m, 1H) 2.15 (m, 1H), 1.6-1.2 (m, 5H). MS m/z 318 (M−1).

EXAMPLE 16

4-(4-Hydroxy-phenyl)-6-methoxymethyl-2,3,3a,4,5,9b-hexahydro-1H-cyclopenta[a]naphthalen-8-ol

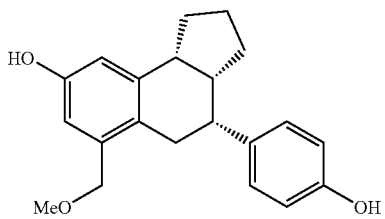

Combine Na (0.013 g, 0.53 mmol) and methanol (2 ml) at 0-5° C. and stir until solution forms. Add 6-Bromomethyl-4-(4-hydroxy-phenyl)-2,3,3a,4,5,9b-hexahydro-1H-cyclopenta[a]naphthalen-8-ol (0.037 g, 0.1 mmol) and stir for 3 hours. Remove solvent in vacuo. Take into ethyl acetate and 1N HCl. Separate organic layer and wash with water. Dry over anhydrous sodium sulfate and remove solvent in vacuo. The residue is chromatographed on silica gel with 25% ethyl acetate/hexanes to yield the titled compound (0.012 g, 37%). $^1$H NMR (DMSO-d$_6$): 9.16(s, 1H), 9.04 (s, 1H), 7.11 (d, J=7.9 Hz, 2H), 6.71 (d, J=8.8 Hz, 2H), 6.58 (s, 1H), 6.53 (s, 1H), 4.35 (dd, j=16 and 7 Hz, 2H), 3.4 (m, 1H presumed), 3.0 (m, 1H), 2.76 (m, 1H), 2.65 (m, 1H), 2.45(m, 1H) 2.15 (m, 1H), 1.6-1.2 (m, 5H). MS m/z 323 (M−1).

EXAMPLE 17

6-Azidomethyl-4-(4-hydroxy-phenyl)-2,3,3a,4,5,9b-hexahydro-1H-cyclopenta[a]naphthalen-8-ol

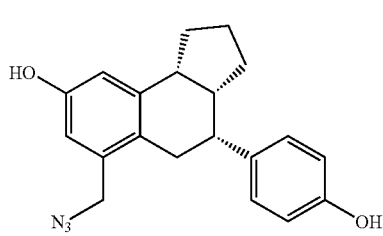

Combine 6-Bromomethyl-4-(4-hydroxy-phenyl)-2,3,3a,4,5,9b-hexahydro-1H-cyclopenta[a]naphthalen-8-ol (0.037 g, 0.1 mmol), LiN$_3$ (0.0213 g, 0.43 mmol), and DMF (1.5 ml) and heat at 90° C. for 3 hours. Cool, add ice and extract with ethyl acetate. Wash organic layer with 3× with water. Dry over anhydrous sodium sulfate and concentrate to a residue which yields after separation on silica gel with 20% EtOAC/hexanes, the titled compound (0.01 g, 34%). $^1$H NMR (CDCl$_3$) 7.2 (d, J=8.4 Hz, 2H), 6.85 (d, J=8.4 Hz, 2H), 6.73 (s, 1H), 6.68 (s, 1H), 4.35 (s, 2H), 3.45 (m, 1H), 3.15 (m, 1H), 2.95 (m, 1H), 2.85 (m, 1H) 2.55 (m, 1H), 2.25 (m, 1H), 1.7-1.2 (m, 5H). MS m/z 334 (M−1).

EXAMPLE 18

4-(4-Hydroxy-phenyl)-6-vinyl-2,3,3a,4,5,9b-hexahydro-1H-cyclopenta[a]naphthalen-8-ol (racemic)

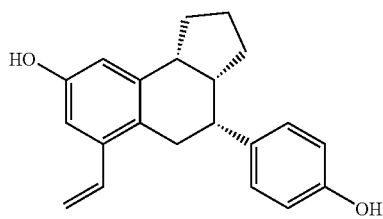

Combine BuLi (0.1 ml, 1.6M, 0.16 mmol), methyltriphenylphosphonium bromide (0.063 g, 0.175 mmol) and tetrahydrofuran (1.0 ml) and stir 15 minutes. Add 8-Hydroxy-4-(4-hydroxy-phenyl)-2,3,3a,4,5,9b-hexahydro-1H-cyclopenta[a]naphthalene-6-carbaldehyde (0.012 g, 0.04 mmol) in tetrahydrofuran (1.0 ml) and stir 30 minutes. Take into ethyl acetate and wash with ammonium chloride solution solution, then brine. Dry over anhydrous sodium sulfate and concentrate to a residue which yields after separation on silica gel with 33% EtOAC/hexanes, the titled compound (0.006 g, 50%). $^1$H NMR (CD$_3$OD) 7.15 (d, J=8.4, Hz, 2H), 7.04 (dd, J=11 and 6 Hz, 1H), 6.75 (m, 3H), 3.4 (m, 1H), 3.0 (m, 1H), 2.85 (m, 2H), 2.55(m, 1H) 2.2 (m, 1H), 1.6-1.2. MS m/z 305 (M−1).

EXAMPLE 19

9-(4-Hydroxy-phenyl)-4b,5,6,7,8,8a,9,10-octahydro-phenanthrene-1,3-diol (racemic)

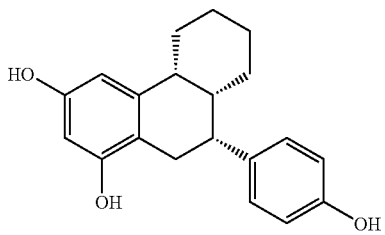

Example 19 is prepared from preparation 115 in a manner similar to Example 1. $^1$H NMR (DMSO-$d_6$): 9.17 (s, 1H), 9.06 (s, 1H), 8.83 (s, 1H), 7.12 (d, J=8.4 Hz, 2H), 6.73 (d, J=8.8 Hz, 2H), 6.27 (s, 1H), 6.17 (s, 1H), 3.05 (s, 1H), 2.95 (m, 1H), 2.65 (m, 2H), 2.3 (d, J=13 Hz, 1H), 1.9 (m, 1H), 1.55 (m, 2H), 1.38 (m, 1H), 1.2-0.9 (m, 4H). MS m/z 309 (M−1).

Separate example 19 into its enantiomers using the conditions described for the separation of example 1 into its enantiomers (examples 1A and 1B).

EXAMPLE 20

1-Bromomethyl-9-(4-hydroxy-phenyl)-4b,5,6,7,8,8a,9,10-octahydro-phenanthren-3-ol

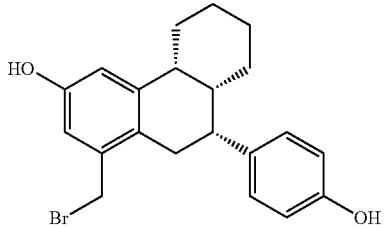

Example 20 is prepared from preparation 118 in a manner similar to example 14.

MS m/z 387, 385 (M$^+$).

Separate example 20 into its enantiomers using the conditions described for the separation of example 1 into its enantiomers (examples 1A and 1B).

EXAMPLE 21

9-(4-Hydroxy-phenyl)-1-methoxymethyl-4b,5,6,7,8,8a,9,10-octahydro-phenanthren-3-ol

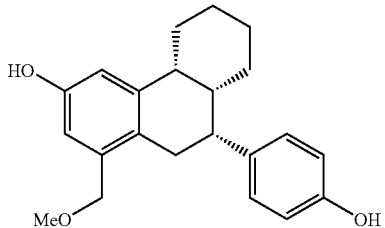

Example 21 is prepared from example 20 in a manner similar to example 16. $^1$H NMR (DMSO-$d_6$): 9.19 (s, 1H), 9.03 (s, 1H), 7.14 (d, J=8.4 Hz, 2H), 6.74 (m, 3H), 6.66 (s, 1H), 4.38 (dd, J=19 and 12 Hz, 2H), 3.15 (s, 1H), 3.0 (m, 1H), 2.9 (m, 1H), 2.65 (m, 1H), 2.4 (m, 1H), 1.9 (m, 1H), 1.7-0.9 (m, 7H). MS m/z 337 (M−1).

Separate example 21 into its enantiomers using the conditions described for the separation of example 1 into its enantiomers (examples 1A and 1B).

EXAMPLE 22

3-Hydroxy-9-(4-hydroxy-phenyl)-4b,5,6,7,8,8a,9,10-octahydro-phenanthrene-1-carboxylic acid methyl ester

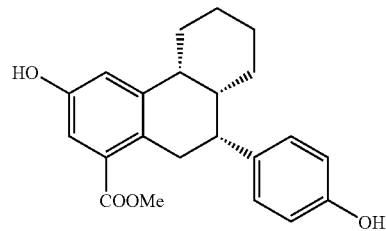

Example 22 is prepared from preparation 117 in a manner similar to example 1. $^1$H NMR (DMSO-$d_6$): 9.47 (s, 1H), 9.21 (s, 1H), 7.11 (d, J=8.4 Hz, 2H), 7.04 (s, 1H), 6.74 (d, J=8.4 Hz, 2H), 3.8 (s, 3H), 3.32 (m, 1h), 3.18 (m, 2H), 2.95 (m, 2H), 3.0 (m, 1H), 2.4 (m, 1H), 1.95 (m, 1H), 1.65 (m, 1H), 1.55 (m, 1H), 1.4 (m, 1H), 1.3-0.9 (m, 2H). MS m/z 351 (M−1).

Separate example 22 into its enantiomers using the conditions described for the separation of example 1 into its enantiomers (examples 1A and 1B).

EXAMPLE 23

1-Hydroxymethyl-9-(4-hydroxy-phenyl)-4b,5,6,7,8,8a,9,10-octahydro-phenanthren-3-ol

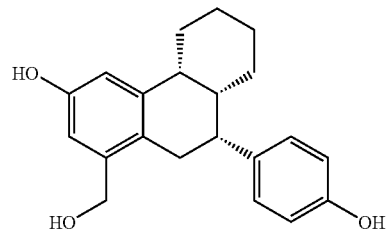

Example 23 is prepared from example 22 in a manner similar to preparation 104. $^1$H NMR (DMSO-$d_6$): 9.18 (s, 1H), 8.95 (s, 1H), 7.14 (d, J=8.8 Hz, 2H), 6.75 (m, 3H), 6.69 (s, 1H), 4.45 (m, 2H), 3.15 (m, 1H), 3.0 (m, 1H), 2.9 (m, 1H), 2.65 (m, 1H), 2.4 (m, 1H), 1.9 (m, 1H), 1.7-0.9 (m, 7H). MS m/z 323 (M−1).

Separate example 23 into its enantiomers using the conditions described for the separation of example 1 into its enantiomers (examples 1A and 1B).

EXAMPLE 24

[3-Hydroxy-9-(4-hydroxy-phenyl)-4b,5,6,7,8,8a,9,10-octahydro-phenanthren-1-yl]-acetonitrile

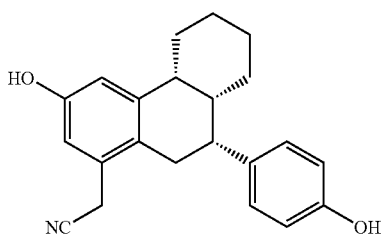

Example 24 is prepared from example 20 in a manner similar to example 15. $^1$H NMR (DMSO-$d_6$): 9.28 (s, 1H), 9.21 (s, 1H), 7.16 (d, J=8.4 Hz, 2H), 6.8 (s, 1H), 6.74 (m, 3H), 3.97 (s, 2H), 3.15 (m, 1H), 3.05 (m, 1H), 2.9 (m, 1H), 2.65 (m, 1H), 2.4 (m, 1H), 1.95 (m, 1H), 1.65 (m, 1H), 1.55 (m, 1H), 1.4 (m, 1H), 1.3-0.8 (m, 4H). MS m/z 332 (M−1).

Separate example 24 into its enantiomers using the conditions described for the separation of example 1 into its enantiomers (examples 1A and 1B).

EXAMPLE 25

3-Hydroxy-9-(4-hydroxy-phenyl)-4b,5,6,7,8,8a,9,10-octahydro-phenanthrene-1-carbonitrile (racemic)

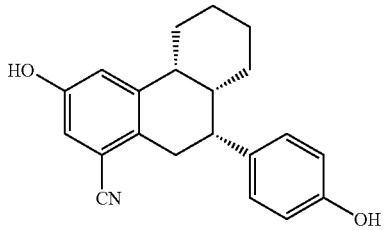

Combine 3-Methoxy-9-(4-methoxy-phenyl)-4b,5,6,7,8,8a,9,10-octahydro-phenanthrene-1-carbonitrile (0.066 g, 0.19 mol) and pyridine hydrochloride (6.5 g) and heat at 200-215° C. for 30 minutes. Cool to r.t. and dilute with 2N HCl and ethyl acetate. Wash organic layer with water and dry over anhydrous sodium sulfate. Remove solvent in vacuo and chromatograph on silica gel with 20% ethyl acetate/hexanes to yield Example 25 (0.03 g, 49%). $^1$H NMR (DMSO-$d_6$): 9.88 (s, 1H), 9.25 (s, 1H), 7.14 (m, 3H), 7.0 (s, 1H), 6.75 (d, J=8.4 Hz, 2H), 3.15 (m, 1H), 3.05 (m, 1H), 2.9 (m, 1H), 2.65 (m, 1H), 2.4 (m, 1H), 1.95 (m, 1H), 1.65 (m, 1H), 1.55 (m, 1H), 1.4 (m, 1H), 1.3-0.8 (m, 4H).

MS m/z 318 (M−1).

Separate example 25 into its enantiomers using the conditions described for the separation of example 1 into its enantiomers (examples 1A and 1B).

EXAMPLE 26

3-Hydroxy-9-(4-hydroxy-phenyl)-4b,5,6,7,8,8a,9,10-octahydro-phenanthrene-1-carboxylic acid amide

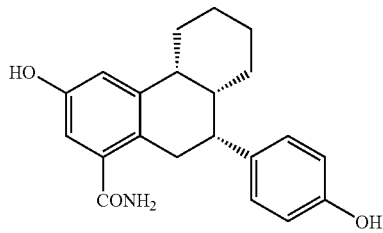

Example 26 is prepared from preparation 121 in a manner similar to example 1. $^1$H NMR (DMSO-$d_6$): 9.28 (s, 1H), 9.21 (s, 1H), 7.7 (s, 1H), 7.29 (s, 1H), 7.12 (d, J=8.4 Hz, 2H), 6.86 (s, 1H), 6.74 (d, J=7.9 Hz, 2H), 3.15 (m, 1H), 3.05 (m, 1H), 2.9 (m, 1H), 2.65 (m, 1H), 2.4 (m, 1H), 1.95 (m, 1H), 1.65 (m, 1H), 1.55 (m, 1H), 1.4 (m, 1H), 1.3-0.8 (m, 4H). MS m/z 336 (M−1).

EXAMPLE 27

2-Bromo-9-(4-hydroxy-phenyl)-4b,5,6,7,8,8a,9,10-octahydro-phenanthren-3-ol

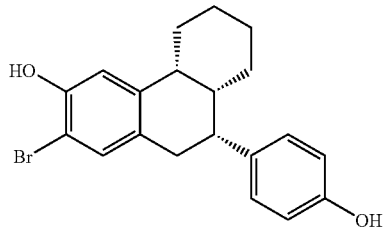

Example 27 is prepared from preparation 123 in a manner similar to example 1. $^1$H NMR (DMSO-$d_6$): 9.83 (s, 1H), 9.2 (s, 1H), 7.27 (s, 1H), 7.1 (d, J=8.8 Hz, 2H), 6.97 (s, 1H), 6.73 (d, J=8.4 Hz, 2H), 3.1 (m, 4H), 2.7 (dd, J=11 and 4 Hz, 1H), 2.34 (m, 1H), 1.92 (m, 1H), 1.8-0.8 (m, 6H). MS m/z 373, 371 (M, M−2).

EXAMPLE 28

1-[3-Hydroxy-9-(4-hydroxy-phenyl)-4b,5,6,7,8,8a,9,10-octahydro-phenanthren-2-yl]-ethanone

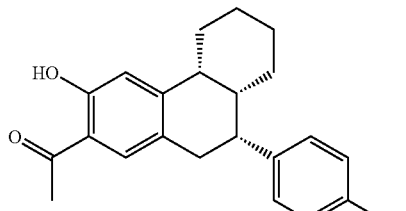

Example 28 is prepared from preparation 124 in a manner similar to example 1. $^1$H NMR (DMSO-d$_6$): 11.77 (s, 1H), 9.23 (s, 1H), 7.72 (s, 1H), 7.14 (d, J=8.8 Hz, 2H), 6.97 (s, 1H), 6.74 (d, J=8.8 Hz, 2H), 3.1 (m, 3H), 2.9 (dd, J=11, 1H), 2.64 (s, 3H), 2.34 (m, 1H), 1.92 (m, 1H), 2.5-0.8 (m, 7H). MS m/z 335 (M−1).

EXAMPLE 29

2-(1-Hydroxy-ethyl)-9-(4-hydroxy-phenyl)-4b,5,6,7,8,8a,9,10-octahydro-phenanthren-3-ol

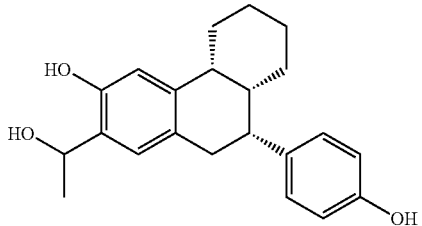

Combine 1-[3-Hydroxy-9-(4-hydroxy-phenyl)-4b,5,6,7,8,8a,9,10-octahydro-phenanthren-2-yl]-ethanone (0.013 g, 0.04 mmol) and NaBH$_4$ (0.016 g, 0.42 mmol) in ethanol (1.5 ml) and heat at 60° C. for 30 minutes. Remove solvent in vacuo and take into ethyl acetate, water, and sodium bicarbonate solution solution. Separate organic layer and wash with water. Dry over anhydrous sodium sulfate and remove solvent in vacuo to yield the titled compound (0.014 g, 100%). $^1$H NMR (CD$_3$0D): 7.16 (d, J=7.9 Hz, 2H), 7.1 (s, 1H), 6.78 (d, J=8.4 Hz, 2H), 5.12 (m, 1H), 3.2 (m, 3H), 2.8 (dd, J=10.5 and 7.5 Hz, 1H), 2.5 (m, 1H), 2.34 (m, 1H), 2.05 (m, 1H), 1.8-1.6 (m, 2H), 1.48 (m, 3H), 1.4-0.8 (m, 4H). MS m/z 337 (M−1).

EXAMPLE 30

9-(4-Hydroxy-phenyl)-4b,5,6,7,8,8a,9,10-octahydro-phenanthrene-2,3-diol

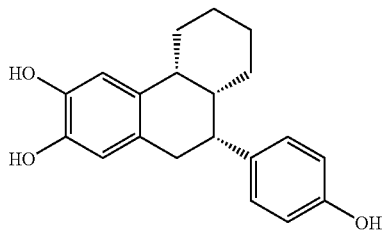

Example 30 is prepared from preparation 125 in a manner similar to example 1. $^1$H NMR (DMSO-d$_6$): 9.17 (s, 1H), 8.58 (s, 1H), 8.54 (s, 1H), 7.1 (d, J=8.4 Hz, 2H), 6.5 (m, 3H), 3.05 (m, 3H), 2.6 (d, J=12.3, 1H), 2.34 (m, 1H), 1.86 (m, 1H), 1.5 (m, 1H), 1.39 (m, 1H), 1.3-0.8 (m, 5H). MS m/z 309 (M−1).

Separate example 30 into its enantiomers using the conditions described for the separation of example 1 into its enantiomers (examples 1A and 1B).

EXAMPLE 31

9-(4-Hydroxy-phenyl)-2-methoxy-4b,5,6,7,8,8a,9,10-octahydro-phenanthren-3-ol

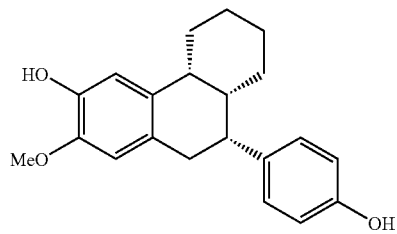

Combine 2-Bromo-9-(4-hydroxy-phenyl)-4b,5,6,7,8,8a,9,10-octahydro-phenanthren-3-ol (chiral) (0.033 g, 0.09 mmol), CuCl$_2$ (0.008 g, 0.06 mmol), 5 M NaOMe (in methanol, 1.5 ml), DMF (0.5 ml) and heat 15 hours at 110° C. Cool, add ethyl acetate and wash with 1N HCl, then water. Dry organic layer over anhydrous sodium sulfate and remove solvent in vacuo. Chromatograph over silica gel 2× first with 20% ethyl acetate/hexanes, then 5-20% ethyl acetate/hexanes to yield the titled compound (0.010 g, 100%). $^1$H NMR (CDCl$_3$): 7.21 (d, J=8.4 Hz, 2H), 7.0 (s, 1H), 6.85 (d, J=8.8 Hz, 2H), 6.69 (s, 1H), 3.91 (s, 3H), 3.2 (m, 4H), 2.85 (dd, J=4 and 11 Hz, 1H), 2.45 (d, J=14.9 Hz, 1H), 2.1-0.8 (m, 7H). MS m/z 323(M−1).

Separate example 31 into its enantiomers using the conditions described for the separation of example 1 into its enantiomers (examples 1A and 1B).

EXAMPLE 32

9-(4-Hydroxy-phenyl)-2-methyl-4b,5,6,7,8,8a,9,10-octahydro-phenanthren-3-ol

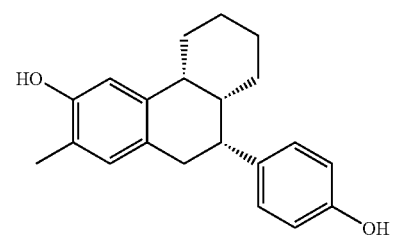

Example 32 is prepared from preparation 126 in a manner similar to example 1. $^1$H NMR (DMSO-d$_6$): 9.18 (s, 1H), 8.89 (s, 1H), 7.1 (d, J=8.4 Hz, 2H), 6.84 (s, 1H), 6.78 (s, 1H), 6.72 (d, J=8.8 Hz, 2H), 3.05 (m, 4H), 2.65 (dd, J=11 and 4 Hz, 1H), 2.35 (m, 1H), 2.08 (s, 3H), 1.9 (m, 1H), 1.7-0.9 (m, 6H). MS m/z 307 (M−1).

Separate example 32 into its enantiomers using the conditions described for the separation of example 1 into its enantiomers (examples 1A and 1B).

EXAMPLE 33

9-(4-Hydroxy-phenyl)-2-propyl-4b,5,6,7,8,8a,9,10-octahydro-phenanthren-3-ol

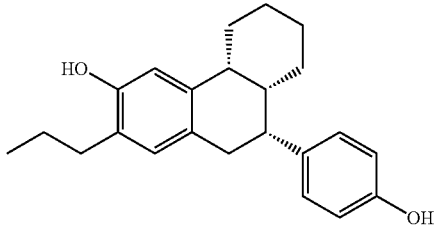

Example 33 is prepared from preparation 127 in a manner similar to example 1. $^1$H NMR (DMSO-d$_6$): 9.18 (s, 1H), 8.85 (s, 1H), 7.1 (d, J=8.8 Hz, 2H), 6.82 (s, 1H), 6.78 (s, 1H), 6.72 (d, J=8.4 Hz, 2H), 3.05 (m, 3H), 2.65 (dd, J=11 and 4 Hz, 1H), 2.45 (m, 2H), 2.35 (m, 1H), 2.08 (s, 3H), 1.95 (m, 1H), 1.8-0.95 (m, 6H), 0.92 (t, J=7.5 and 5.7 Hz, 3H). MS m/z 335 (M−1)

Separate example 33 into its enantiomers using the conditions described for the separation of example 1 into its enantiomers (examples 1A and 1B).

EXAMPLE 34

9-(4-Hydroxy-phenyl)-2-isopropyl-4b,5,6,7,8,8a,9,10-octahydro-phenanthren-3-ol

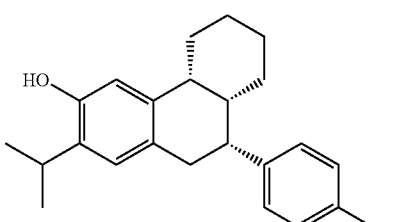

Example 34 is prepared from preparation 129 in a manner similar to example 1. $^1$H NMR (DMSO-d$_6$) 9.18 (s, 1H), 8.89 (s, 1H), 7.12 (d, J=8.4 Hz, 2H), 6.89 (s, 1H), 6.78 (s, 1H), 6.73 (d, J=8.8 Hz, 2H), 3.1 (m, 4H), 2.68 (dd, J=11 and 4 Hz, 1H), 2.45 (m, 2H), 2.33 (d, J=12.7 Hz, 1H), 1.9 (m, 1H), 1.6 (m, 2H), 1.4 (m, 1H), 1.25-0.9 (m, 8H).

MS m/z 335 (M−1).

Separate example 34 into its enantiomers using the conditions described for the separation of example 1 into its enantiomers (examples 1A and 1B).

EXAMPLE 35

5-(4-Hydroxy-phenyl)-1,2,3,4,4a,5,6,8,9,12b-decahydro-11-oxa-benzo[a]anthracen-10-one

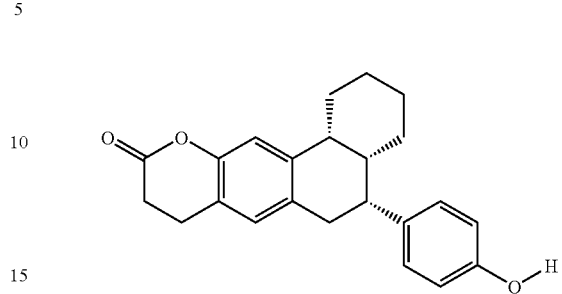

Example 35 is prepared from preparation 132 in a manner similar to example 1. $^1$H NMR (DMSO-d$_6$). 9.21 (s, 1H), 7.13 (d, J=8.4 Hz, 2H), 7.1 (s, 1H), 7.05 (s, 1H), 6.74 (d, J=8.4 Hz, 2H), 3.15 (m, 3H), 2.95 (m, 2H), 2.8 (m, 2H), 2.5 (m, 1H), 1.95 (m, 1H), 1.6 (m, 2H), 1.4 (m, 1H), 1.75-0.9 (m, 5H). MS m/z 347 (M−1).

EXAMPLE 36

3-[3-Hydroxy-9-(4-hydroxy-phenyl)-4b,5,6,7,8,8a,9,10-octahydro-phenanthren-2-yl]-N-methyl-propionamide

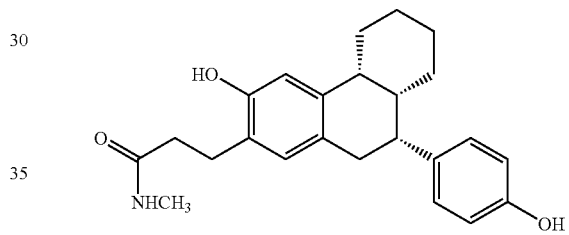

Combine 5-(4-Hydroxy-phenyl)-1,2,3,4,4a,5,6,8,9,12b-decahydro-11-oxa-benzo[a]anthracen-10-one (0.014 g, 0.04 mmol) and excess methylamine (40% in water) in tetrahydrofuran (1 ml). After 30 minutes, remove solvent in vacuo, dissolve in ethyl acetate and dry over anhydrous sodium sulfate. Remove solvent in vacuo to yield the titled compound (0.014 g, 92%). $^1$H NMR (DMSO-d$_6$) 9.19 (s, 1H), 9.02 (s, 1H), 7.11 (d, J=8.8 Hz, 2H), 6.83 (s, 1H), 6.79 (s, 1H), 6.73 (d, J=8.4 Hz, 2H), 3.1 (m, 3H), 2.7 (m, 3H), 2.58 (s, 3H), 2.35 (m, 2H), 1.9 (m, 1H), 1.6 (m, 2H), 1.4 (m, 1H), 1.75-0.9 (m, 5H). MS m/z 378 (M−1).

EXAMPLE 37

3-[3-Hydroxy-9-(4-hydroxy-phenyl)-4b,5,6,7,8,8a,9,10-octahydro-phenanthren-2-yl]-1-piperidin-1-yl-propan-1-one

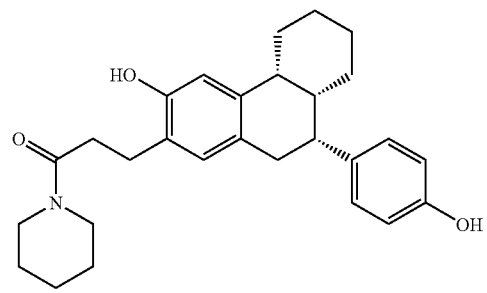

Example 37 is prepared from example 35 in a manner similar to example 36. ¹H NMR (DMSO-d₆). ¹H NMR (DMSO-d₆): 9.19 (s, 1H), 9.1 (s, 1H), 7.1 (d, J=8.8 Hz, 2H), 6.85 (s, 1H), 6.79 (s, 1H), 6.73 (d, J=8.4 Hz, 2H), 3.5 (m, 1H), 3.4 (m, 2H), 3.1 (m, 3H), 2.8-2.4 (m, 5H), 2.35 (m, 1H), 1.9 (m, 1H), 1.7-0.8 (m, 14H). MS m/z 432(M−1).

EXAMPLE 38

3-[3-Hydroxy-9-(4-hydroxy-phenyl)-4b,5,6,7,8,8a,9,10-octahydro-phenanthren-2-yl]-N,N-dimethyl-propionamide

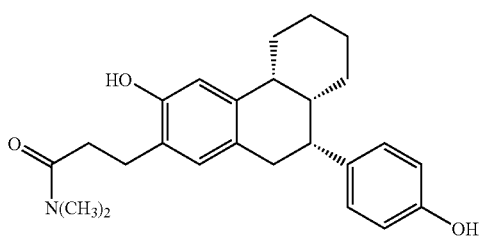

Example 38 is prepared from example 35 in a manner similar to example 36. ¹H NMR (DMSO-d₆): 9.15 (s, 1H), 9.07 (s, 1H), 7.09 (d, J=8.8 Hz, 2H), 6.83 (s, 1H), 6.75 (s, 1H), 6.69 (d, J=8.8 Hz, 2H), 3.0 (m, 3H), 2.95 (s, 3H), 2.8 (s, 3H), 2.65 (m, 3H), 2.55 (m, 3H), 2.3 (m, 1H), 1.8 (m, 1H), 1.75 (m, 1H), 1.65-0.8 (m, 5H). MS m/z 392(M−1).

EXAMPLE 39

3-[3-Hydroxy-9-(4-hydroxy-phenyl)-4b,5,6,7,8,8a,9,10-octahydro-phenanthren-2-yl]-propionamide

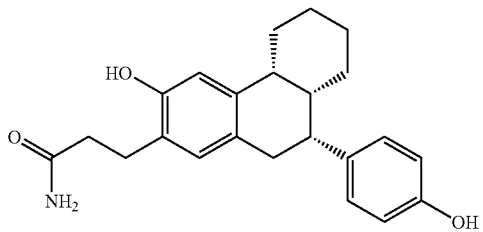

Example 38 is prepared from example 35 in a manner similar to example 36. ¹H NMR (DMSO-d₆): 9.14 (s, 1H), 8.98 (s, 1H), 7.28 (s, 1H), 7.07 (d, J=8.4 Hz, 2H), 6.81 (s, 1H), 6.75 (s, 1H), 6.69 (d, J=8.4 Hz, 2H), 3.0 (m, 3H), 2.63 (m, 3H), 2.3 (m, 3H), 1.9 (m, 1H), 1.7-0.8 (m, 7H). MS m/z 364(M−1).

EXAMPLE 40

9-(4-Hydroxy-phenyl)-2-(3-hydroxy-propyl)-4b,5,6,7,8,8a,9,10-octahydro-phenanthren-3-ol

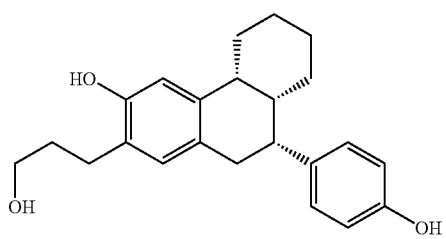

Combine 5-(4-Hydroxy-phenyl)-1,2,3,4,4a,5,6,8,9,12b-decahydro-11-oxa-benzo[a]anthracen-10-one (0.05 g, 0.143 mmol), lithium aluminum hydride 0.05 g, 1.43 mmol), and tetrahydrofuran (10 ml) and stir 1.5 hours. Add ethyl acetate followed by 1N HCl. Filter precipitate and wash organic layer water, dry over anhydrous sodium sulfate and remove solvent in vacuo. Chromatograph the residue on silica gel with ethyl acetate/hexanes 1/1 to yield Example 40 (0.032 g, 63%). ¹H NMR (DMSO-d₆): 9.14 (s, 1H), 8.84 (s, 1H), 7.07 (d, J=8.4 Hz, 2)H), 6.79 (s, 1H), 6.74 (s, 1H), 6.69 (d, J=8.4 Hz, 2H), 3.4 (q, J=7 and 5 Hz, 2H), 3.0 (m, 3H), 2.63 (m, 2H), 2.3 (m, 1H), 1.9 (m, 1H), 1.7-0.8 (m, 10H). MS m/z 351 (M−1).

Separate example 40 into its enantiomers using the conditions described for the separation of example 1 into its enantiomers (examples 1A and 1B).

EXAMPLE 41

2-(3-Dimethylamino-propyl)-9-(4-hydroxy-phenyl)-4b,5,6,7,8,8a,9,10-octahydro-phenanthren-3-ol

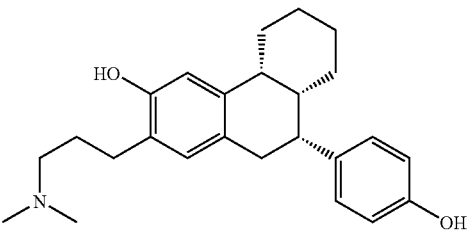

Combine 3-[3-Hydroxy-9-(4-hydroxy-phenyl)-4b,5,6,7,8,8a,9,10-octahydro-phenanthren-2-yl]-N,N-dimethyl-propionamide (0.009 g, 0.023 mmol), lithium aluminum hydride (0.04 mmol), and tetrahydrofuran (1 ml) and stir 3 hours. Add ethyl acetate and water. Dry organic layer over anhydrous sodium sulfate and remove solvent in vacuo. Chromatograph the residue over silica gel to yield Example 40 (0.0036 g, 42%). ¹H NMR (CD₃OD): 7.11 (d, J=8.4 Hz, 2H), 6.86 (s, 1H), 6.81 (s, 1H), 6.73 (d, J=8.4 Hz, 2H), 3.1 (m, 3H), 2.7 (dd, J=11 and 5 Hz, 1H), 2.6 (t, J=7 and 7.5 Hz, 2H), 2.45 (t, J=7.5 and 7 Hz, 3H), 2.35 (s, 6H), 2.0-0.8 (m, 10H). MS m/z 380 (M+1).

EXAMPLE 42

9-(4-Hydroxy-phenyl)-2-(3-methoxy-propyl)-4b,5,6,7,8,8a,9,10-octahydro-phenanthren-3-ol

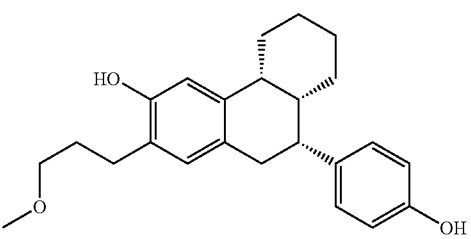

Combine Methanesulfonic acid 9-(4-methanesulfonyloxy-phenyl)-2-(3-methoxy-propyl)-4b,5,6,7,8,8a,9,10-octahydro-phenanthren-3-yl ester (0.044 g, 0.084 mmol), 5N KOH (2 Ml), and methanol (2 ml) and heat at 80° C. for 2 hours. Remove solvent in vacuo. Add ethyl acetate and 6N HCl. Wash organic layer with water, dry over anhydrous sodium sulfate and remove solvent in vacuo. Chromatograph the residue on silica gel with 25% ethyl acetate/hexanes to yield Example 42 (0.008 g, 26%). $^1$H NMR (CDCl$_3$): 7.17 (d, J=8.4 Hz, 2H), 6.91 (s, 1H), 6.87 (s, 1H), 6.8 (d, J=8.4 Hz, 2H), 3.4 (s, 4H), 3.15 (m, 3H), 2.7 (m, 3H), 2.45 (m, 1H), 2.1-1.0(m, 11H). MS m/z 365 (M−1).

EXAMPLE 43

2-(3-Bromo-propyl)-9-(4-hydroxy-phenyl)-4b,5,6,7,8,8a,9,10-octahydro-phenanthren-3-ol

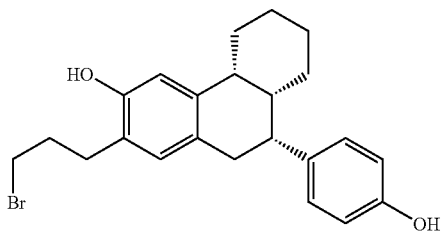

Example 43 is prepared from Example 40 in a manner similar to Example 1. $^1$H NMR (CDCl$_3$): 7.17 (d, J=8.4 Hz, 2H), 6.92 (s, 1H), 6.81 (d, J=8.8 Hz, 2H), 6.78 (s, 1H), 3.47 (t, J=6.7 and 6.6 Hz, 2H), 3.1 (m, 4H), 2.78 (m, 3H), 2.4 (m, 1H), 2.1-1.0(m, 9H).

MS m/z 365 (M−1).

EXAMPLE 44

2-Hydroxymethyl-9-(4-hydroxy-phenyl)-4b,5,6,7,8,8a,9,10-octahydro-phenanthren-3-ol

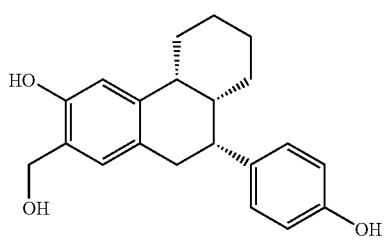

Example 44 is prepared from preparation 136 in a manner similar to preparation 104. NMR (CD$_3$OD): 7.12 (d, J=8.4 Hz, 2H), 7.04 (s, 1H), 6.83 (s, 1H), 6.74 (d, J=8.4 Hz, 2H), 4.61 (s, 2H), 3.25-3.0 (m, 4H), 2.75 (dd, J=4.8 and 11 Hz, 1H), 2.47 (d, J=14.6 Hz, 1H), 2.0 (m, 1H), 1.8-0.8 (m, 6H), MS m/z 337 (M−1).

EXAMPLE 45

9-(4-Hydroxy-phenyl)-2-methoxymethyl-4b,5,6,7,8,8a,9,10-octahydro-phenanthren-3-ol

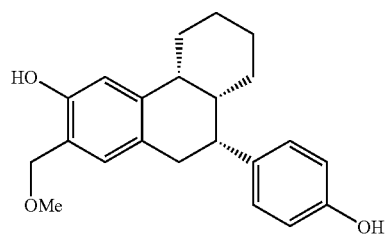

Combine 3-Hydroxy-9-(4-methoxy-phenyl)-4b,5,6,7,8,8a,9,10-octahydro-phenanthrene-2-carbaldehyde (0.098 g, 0.29 mmol), decaborane(14) (0.021 g, 0.16 mmol) and methanol (5 ml) and stir for 21 hours. Remove solvent in vacuo. Add ethyl acetate wash with 1N HCl then water. Dry over anhydrous sodium sulfate and remove solvent in vacuo. Chromatograph the residue on silica gel with 20% ethyl acetate/hexanes to yield Example 44 (0.037 g, 36%). $^1$H NMR (CD$_3$OD): 7.13 (d, J=8.4 Hz, 2H), 7.01 (s, 1H), 6.85 (s, 1H), 6.74 (d, J=8.8 Hz, 2H), 4.46 (s, 2H), 3.38 (s, 3H), 3.25-3.0 (m, 4H), 2.75 (dd, J=4.8 and 11 Hz, 1H), 2.45 (m, 1H), 2.0 (m, 1H), 1.8-0.8 (m, 6H), MS m/z 337 (M−1).

Separate example 45 into its enantiomers using the conditions described for the separation of example 1 into its enantiomers (examples 1A and 1B).

EXAMPLE 46

9-(4-Hydroxy-phenyl)-10-methyl-4b,5,6,7,8,8a,9,10-octahydro-phenanthren-3-ol

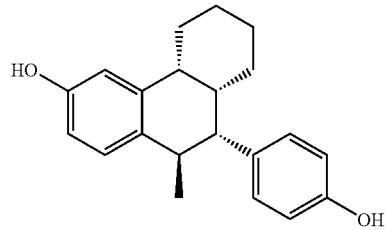

Example 46 is prepared from preparation 144 in a manner similar to example 1. TLC Rf=0.47 in 1:1 hexanes:ethyl acetate. $^1$H NMR (d-methanol): 7.22 (d, 1H, J=8.8 Hz), 7.11 (d, 2H, J=8.4 Hz), 6.83 (m, 1H), 6.78 (d, 2H, J=8.4 Hz), 6.64 (dd, 1H, J=8.4, 2.2 Hz), 3.24 (m, 1H), 2.73 (dd, 1H, J=11.7, 2.4 Hz), 2.48 (d, 1H, J=13.7 Hz), 1.83 (m, 1H), 1.63 (m, 2H), 1.41 (d, 2H, J=10.1 Hz), 1.15 (m, 7H); MS m/z 307(M−1).

Separate example 46 into its enantiomers using the conditions described for the separation of example 1 into its enantiomers (examples 1A and 1B).

EXAMPLE 47

6-Hydroxy-10-(4-hydroxy-phenyl)-1,2,3,4,4a,9,10,10a-octahydro-phenanthrene-9-carboxylic acid

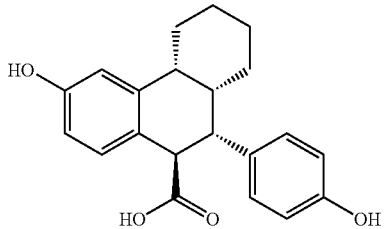

Example 47 is prepared from preparation 145 in a manner similar to example 1. TLC Rf=0.11 in 3:7 (10% methanol/ethyl acetate):(50% hexanes:DCM). ¹H NMR (DMSO): 7.18 (m, 3H), 6.91 (s, 1H), 6.77 (d, 2H, J=8.4 Hz), 6.65 (dd, 1H, J=8.4, 1.8 Hz), 4.26 (d, 1H, J=12.3 Hz), 3.47 (m, 2H), 3.31 (m, 1H), 2.52 (d, 1H, J=14.1 Hz), 1.96 (m, 1H), 1.68 (m, 2H), 1.43 (m, 2H), 1.11 (m, 2H); MS m/z 337 (M−1).

EXAMPLE 48

6-Hydroxy-10-(4-hydroxy-phenyl)-1,2,3,4,4a,9,10,10a-octahydro-phenanthrene-9-carboxylic acid methyl ester

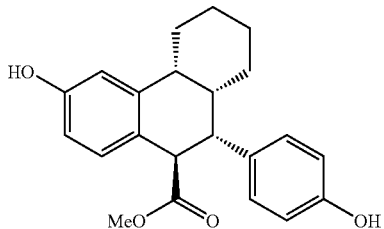

Combine 6-hydroxy-10-(4-hydroxy-phenyl)-1,2,3,4,4a,9,10,10a-octahydro-phenanthrene-9-carboxylic acid (0.903 g, 2.67 mmol), AcCl (2 mL), and methanol (20.0 mL), and reflux under nitrogen atmosphere. After 72 hours, concentrate reaction to dryness under vacuum, add ethyl acetate and water. Separate the organic phase and wash with brine. Dry the organic phase with anhydrous sodium sulfate and concentrate to yield the titled compound (0.980 g, 99%) as a brown solid. ¹H NMR (d-methanol): 7.15 (d, 2H, J=8.4 Hz), 7.04 (d, 1H, J=8.8 Hz), 6.91 (s, 1H), 6.77 (d, 2H, J=8.4 Hz), 6.64 (m, 1H), 4.32 (d, 1H, J=12.8 Hz), 3.58 (s, 3H), 3.45 (dd, 1H, J=12.6, 2.4 Hz), 3.34 (s, 1H), 2.52 (d, 1H, J=14.1 Hz), 1.97 (m, 1H), 1.68 (m, 2H), 1.44 (m, 2H), 1.11 (m, 3H); MS m/z 351 (M−1).

EXAMPLE 49

10-Bromomethyl-9-(4-hydroxy-phenyl)-4b,5,6,7,8,8a,9,10-octahydro-phenanthrene-3-ol

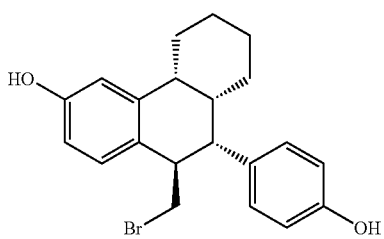

Example 49 is prepared from preparation 142 in a manner similar to example 1. ¹H NMR (d-methanol): 7.24 (d, 1H, J=8.4 Hz), 7.13 (d, 2H, J=8.4 Hz), 6.85 (m, 1H), 6.81 (d, 2H, J=8.4 Hz), 6.68 (dd, 1H, J=8.4, 2.6 Hz), 4.02 (dd, 1H, J=10.3, 2.9 Hz), 3.60 (d, 1H, J=11.5 Hz), 3.49 (m, 1H), 3.31 (dd, 1H, J=11.7, 2.9 Hz), 3.17 (s, 1H), 2.48 (d, 1H, J=13.7 Hz), 1.89 (m, 1H), 1.64 (m, 2H), 1.45 (m, 2H), 1.14 (m, 3H); MS m/z 385, 387 (M−1).

EXAMPLE 50

10-Bromomethyl-9-(4-hydroxy-phenyl)-4b,5,6,7,8,8a,9,10-octahydro-phenanthrene-3-ol

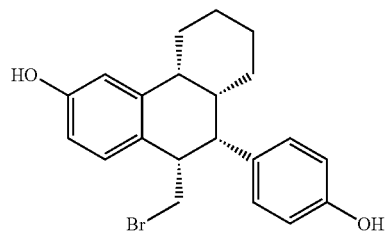

Example 50 is prepared from preparation 146 in a manner similar to example 1. ¹H NMR (d-methanol): 7.29 (d, 1H, J=8.4 Hz), 6.84 (m, 3H), 6.68 (dd, 1H, J=8.4, 2.2 Hz), 6.60 (d, 2H, J=8.8 Hz), 3.77 (dd, 1H, J=10.3, 7.3 Hz), 3.57 (dd, 1H, J=10.6, 4.4 Hz), 3.45 (t, 1H, J=6.4 Hz), 3.23 (dd, 1H, J=11.9, 6.6 Hz), 2.99 (m, 1H), 2.49 (m, 1H), 2.23 (m, 1H), 1.80 (m, 1H), 1.50 (m, 2H), 1.39 (m, 1H), 1.26 (m, 2H), 1.02 (m, 1H); MS m/z 385, 387(M−1).

EXAMPLE 51

[6-Hydroxy-10-(4-hydroxy-phenyl)-1,2,3,4,4a,9,10,10a-octahydro-phenanthrene-9-yl]-acetonitrile

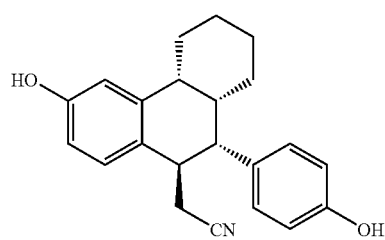

Example 51 is prepared from preparation 147 in a manner similar to example 1. TLC Rf=0.10 in 1:1 hexanes:ethyl acetate. ¹H NMR (d-methanol): 7.27 (d, 1H, J=8.4 Hz), 7.16 (d, 2H, J=8.4 Hz), 6.90 (s, 1H), 6.83 (d, 2H, J=7.9 Hz), 6.72 (d, 1H, J=8.4 Hz), 3.60 (d, 1H, J=11.9 Hz), 3.26 (s, 1H), 3.08 (m, 2H), 2.49 (m, 2H), 1.93 (m, 1H), 1.66 (m, 2H), 1.45 (m, 2H), 1.15 (m, 3H); MS m/z 332 (M−1).

Separate example 51 into its enantiomers using the conditions described for the separation of example 1 into its enantiomers (examples 1A and 1B).

EXAMPLE 52

9-(4-Hydroxy-phenyl)-10-pyrrolidin-1-ylmelthyl-4b,5,6,7,8,8a,9,10-octahydro-phenanthrene-3-ol

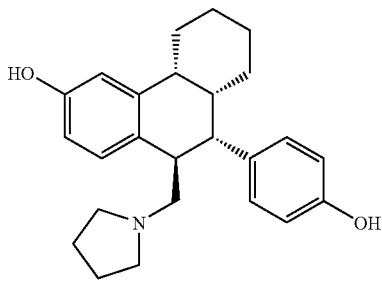

Example 52 is prepared from preparation 148 in a manner similar to example 1. TLC Rf=0.09 in 4% 2M NH$_3$ methanol: DCM. $^1$H NMR (d-methanol): 7.57 (d, 1H, J=8.4 Hz), 7.13 (d, 2H, J=8.4 Hz), 6.82 (s, 1H), 6.77 (d, 2H, J=8.8 Hz), 6.63 (dd, 1H, J=8.4, 2.2 Hz), 3.34 (m, 1H), 3.16 (m, 2H), 2.76 (dd, 1H, J=12.8, 5.7 Hz), 2.61 (dd, 1H, J=12.3, 2.6 Hz), 2.40 (m, 3H), 2.24 (m, 2H), 1.88 (m, 1H), 1.66 (m, 4H), 1.55 (m, 1H), 1.40 (m, 2H), 1.26 (m, 2H), 1.12 (m, 2H); MS m/z 378 (M+1).

Separate example 52 into its enantiomers using the conditions described for the separation of example 1 into its enantiomers (examples 1A and 1B).

EXAMPLE 53

10-Ethyl-9-(4-hydroxy-phenyl)-4b,5,6,7,8,8a,9,10-octahydro-phenanthrene-3-ol

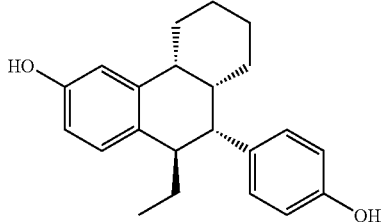

Example 53 is prepared from preparation 149 in a manner similar to example 1. TLC Rf=0.21 in 1:1 hexanes:ethyl acetate. $^1$H NMR (d-methanol): 7.19 (d, 1H, J=8.8 Hz), 7.12 (d, 2H, J=8.4 Hz), 6.84 (s, 1H), 6.78 (d, 2H, J=8.8 Hz), 6.65 (m, 1H), 3.36 (m, 1H), 3.16 (s, 1H), 3.03 (dd, 1H, J=12.1, 2.9 Hz), 2.48 (d, 1H, J=14.1 Hz), 1.88 (m, 2H), 1.60 (m, 3H), 1.41 (d, 2H, J=7.9 Hz), 1.18 (m, 3H), 0.58 (t, 3H, J=7.3 Hz).

EXAMPLE 54

10-Hydroxymethyl-9-(4-hydroxy-phenyl)-4b,5,6,7,8,8a,9,10-octahydro-phenanthren-3-ol

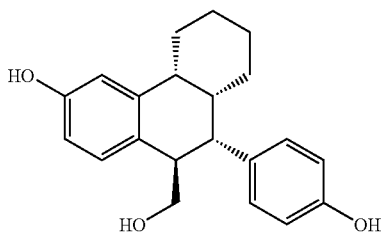

Combine [6-benzyloxy-10-(4-benzyloxy-phenyl)-1,2,3,4,4a,10,10a-octahydro-phenanthrene-9-yl]-methanol (0.071 g, 0.14 mmol), 10% Pd—C (0.005 g, 0.04 mmol), ethanol (10 mL), and tetrahydrofuran (2 mL), and stir under 50 psi of hydrogen atmosphere at room temperature. After 18 hours, filter reaction through celite using ethyl acetate, concentrate, and flash chromatograph eluting with 20% to 75% ethyl acetate/hexanes to yield the titled compound (0.027 g, 60%) as a white solid. TLC Rf=0.23 in 1:1 hexanes:ethyl acetate. $^1$H NMR (CDCl$_3$): 7.43 (d, 1H, J=8.4 Hz), 7.15 (d, 2H, J=8.8 Hz), 6.85 (s, 1H), 6.79 (d, 2H, J=8.4 Hz), 6.68 (dd, 1H, J=8.6, 2.0 Hz), 3.98 (dd, 1H, J=11.0, 2.2 Hz), 3.53 (dd, 1H, J=11.0, 3.5 Hz), 3.33 (m, 2H), 3.18 (m, 2H), 2.49 (d, 1H, J=13.2 Hz), 1.89 (m, 1H), 1.64 (m, 2H), 1.40 (s, 1H), 1.20 (m, 2H), 1.20 (m, 1H);

MS m/z 323 (M−1).

EXAMPLE 55

9-(4-Hydroxy-phenyl)-10-methoxymethyl-4b,5,6,7,8,8a,9,10-octahydro-phenanthren-3-ol

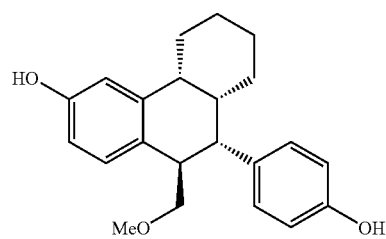

Combine 6-methoxy-9-methoxymethyl-10-(4-methoxyphenyl)-1,2,3,4,4a,9,10,10a-octahydro-phenanthrene (0.050 g, 0.14 mmol), sodium ethanethiolate (0.037 g, 0.44 mmol), and DMF (4 mL), and reflux under nitrogen atmosphere. After 18 hours, cool the reaction to room temperature and add ethyl acetate, wash with sat ammonium chloride solution (aq), then brine several times. Concentrate, and purify using reverse phase chromatography (5% to 95% 0.001% TFA buffer in acetonitrile/water) to yield the titled compound (0.015 g, 33%) as a white solid. TLC Rf=0.27 in 3:1 hexanes: ethyl acetate. $^1$H NMR (d-methanol): 7.42 (d, 1H, J=8.4 Hz), 7.13 (d, 2H, J=8.4 Hz), 6.84 (s, 1H), 6.79 (d, 2H, J=8.4 Hz), 6.65 (dd, 1H, J=7.9, 1.8 Hz), 3.70 (d, 1H, J=7.0 Hz), 3.35 (m, 3H), 3.17 (s, 3H), 3.07 (m, 1H), 2.48 (d, 1H, J=14.1 Hz), 1.87 (m, 1H), 1.64 (m, 2H), 1.41 (m, 2H), 1.16 (m, 3H).

EXAMPLE 56

1-[6-Hydroxy-10-(4-hydroxy-phenyl)-1,2,3,4,4a,9,10,10a-octahydro-phenanthren-9-yl]-ethanone

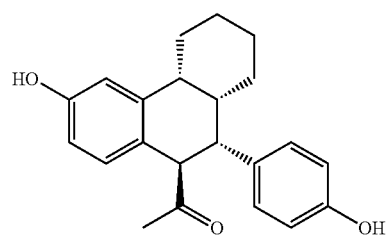

Example 56 is prepared from preparation 153 in a manner similar to example 1. $^1$H NMR (d-methanol): 7.16 (d, 2H, J=8.8 Hz), 6.96 (m, 1H), 6.83 (d, 1H, J=8.4 Hz), 6.77 (d, 2H, J=8.8 Hz), 6.64 (dd, 1H, J=8.4, 2.2 Hz), 4.26 (d, 1H, J=12.8 Hz), 3.35 (m, 2H), 2.53 (d, 1H, J=14.5 Hz), 1.98 (m, 1H), 1.90 (s, 3H), 1.74 (m, 1H), 1.61 (s, 1H), 1.44 (m, 2H), 1.12 (m, 3H); MS m/z 335 (M−1).

EXAMPLE 57

10-(1-Hydroxy-ethyl)-9-(4-hydroxy-phenyl)-4b,5,6,7,8,8a,9,10-octahydro-phenanthren-3-ol

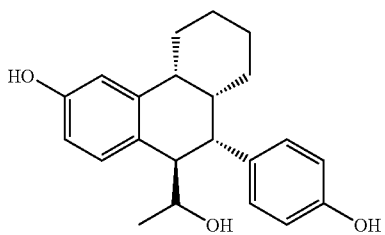

Combine 1-[6-hydroxy-10-(4-hydroxy-phenyl)-1,2,3,4,4a,9,10,10a-octahydro-phenanthren-9-yl]-ethanone (0.027 g, 0.08 mmol), NaBH$_4$ (0.010 g, 0.24 mmol), and ethanol (4 mL), and reflux under nitrogen atmosphere. After 72 hours, cool the reaction to room temperature, concentrate, and add ethyl acetate. Wash with sat ammonium chloride solution (aq), then brine, and purify using reverse phase chromatography (5% to 95% 0.001% TFA buffer in acetonitrile/water) to yield the titled compound (0.003 g, 11%) as a white solid. $^1$H NMR (d-methanol): 7.62 (d, 1H, J=8.4 Hz), 7.15 (m, 2H), 6.84 (s, 1H), 6.78 (m, 2H), 6.64 (m, 1H), 3.94 (m, 1H), 3.49 (d, 1H, J=11.5 Hz), 3.33 (m, 1H), 3.13 (s, 1H), 2.91 (dd, 1H, J=11.5, 3.5 Hz), 2.47 (m, 1H), 1.86 (m, 1H), 1.68 (m, 1H), 1.52 (m, 1H), 1.30 (m, 3H), 1.05 (m, 4H), 0.83 (d, 2H, J=6.2 Hz); MS m/z 337 (M−1).

EXAMPLE 58

9-(4-Hydroxy-phenyl)-10-methyl-4b,5,6,7,8,8a,9,10-octahydro-phenanthren-3-ol

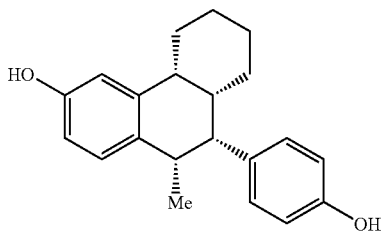

Example 58 is prepared from preparation 155 in a manner similar to example 1. TLC Rf=0.30 in 1:9 (10% methanol/ethyl acetate):(50% hexanes/DCM). $^1$H NMR (CDCl$_3$): 7.18 (d, 1H, J=8.4 Hz), 6.97 (d, 2H, J=8.4 Hz), 6.90 (d, 1H, J=2.6 Hz), 6.74 (m, 3H), 3.31 (m, 2H), 3.05 (m, 1H), 2.50 (m, 1H), 2.29 (m, 1H), 1.79 (m, 1H), 1.49 (m, 4H), 1.25 (m, 2H), 1.13 (d, 3H, J=6.6 Hz).

Separate example 58 into its enantiomers using the conditions described for the separation of example 1 into its enantiomers (examples 1A and 1B).

EXAMPLE 59

4-Amino-9-(4-hydroxy-phenyl)-4b,5,6,7,8,8a,9,10-octahydro-phenanthren-3-ol

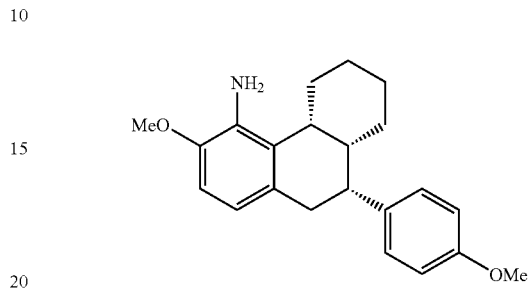

Example 59 is prepared from preparation 160 in a manner similar to example 1. (15.8 mg, 49%). $^1$H NMR (d-methanol): 7.14 (m, 2H), 7.03 (t, 1H, J=7.5 Hz), 6.87 (d, 1H, J=8.4 Hz), 6.76 (d, 2H, J=8.4 Hz), 3.43 (m, 1H), 3.32 (m, 1H), 3.04 (m, 1H), 2.84 (dd, 1H, J=16.3, 4.8 Hz), 2.25 (m, 1H), 1.97 (m, 1H), 1.73 (m, 1H), 1.48 (m, 4H), 1.21 (m, 2H); MS m/z 310(M+1).

Test Procedures

ER Binding Assay

The competition ER binding assay is run in a buffer containing 50 mM N-[2-hydroxyethyl]piperazine-N'-[2-ethane-sulfonic acid (Hepes) pH 7.5, 1.5 mM EDTA, 150 mM NaCl, 10% glycerol, 1 mg/mL ovalbumin, 5 mM DTT, 0.025 μCi per well of $^3$H-Estradiol (New England Nuclear #NET517 at 118 Ci/mmol, 1 mCi/mL), and 10 ng/well ER-α or ER-β Receptor (PanVera). Competing compounds are added at 10 different concentrations. Non-specific binding is determined in the presence of 1 μM of E2 (17-β Estradiol, Sigma, St. Louis, Mo.). The binding reaction (140 μL) is incubated for 4 hours at room temperature, then 70 μL of cold dextran coated charcoal (DCC) buffer is added to each reaction (DCC buffer is prepared by adding 0.75 g of charcoal [Sigma] and 0.25 g of dextran [Pharmacia] per 50 mL of assay buffer). The incubation plates are mixed for 8 minutes on an orbital shaker at 4° C. and then centrifuged at 3,000 rpm for 10 minutes at 4° C. An aliquot of 120 μl of the mix is transferred to another 96-well, white flat bottom plate (Costar) and 175 μl of Wallac Optiphase Hisafe 3 scintillation fluid is added to each well. The plates are sealed and then shaken vigorously on an orbital shaker. After an incubation of 2.5 hrs, the radioactivity is counted in a Wallac Microbeta counter. The IC$_{50}$ and percent inhibition at 10 μM are calculated. The K$_d$ for $^3$H-Estradiol is determined by saturation binding to ER-α and ER-β receptors. The IC$_{50}$ values for compounds are converted to K$_i$ values using the Cheng-Prusoff equation and the K$_d$ values are determined by saturation binding assay.

Preferred compounds bind to the ER-β receptor with a K$_i$ of less than 20 nM. More preferred compounds bind to the ER-β receptor with a K$_i$ of less than 1 nM. Compounds that are selective to binding to the ER-β receptor compared to the ER-α receptor bind to the ER-β receptor with a lower K$_i$ compared to the K$_i$ for the ER-α receptor.

As determined by the above assay, the compounds of examples 1-59 exhibit binding affinities (Ki) at the ER-α subtype in the range approximately 4→1000 nM and to the ER-β subtype in the range of approximately 0.2-500 nM.

ER Agonist Assay

The agonist activity of the compounds of the invention can be determined from assay(s) described in Harris, H. A.; Katzenellenbogen, J. A.; Katzenellenbogen, B. S. Endocrinology, 143, p. 4172-4177 (2002).

LNCaP Human PCa Xenograft Assay

ER-β agonists are evaluated for their effects on the growth of androgen-sensitive LNCaP human prostatic cancer (PCa) xenografts grown in intact sexually mature (5-6 weeks old) Hsd: Athymic Nude-nu (Athymic Nude) male mice. $2.0 \times 10^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in $mm^3$ are calculated in JMP using the following formula: L×W×H×0.5236. Tumor and body weight responses for individual mice are recorded on a weekly basis. When LNCaP tumor volumes enter log-phase expansion, lesions are measured every 3-4 days. Growth rates are determined using linear modeling of the log tumor values and time-to-treatment failure (tumor vol=1300-1500 $mm^3$) are determined using a linear extrapolation model (SAS; Cary, N.C.). Because of humane animal use considerations, animals are sacrificed when their tumor volumes approach 1200-1400 $mm^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at −80° C. for biomarker analysis.

Benign Prostatic Hypertrophy (BPH) Assay

A mouse BPH study is essentially performed as a modified version of the rat BPH study as described earlier (Eur J Endocrinol. 2004 April; 150(4):591-60313). Thirteen week CD-1 male mice are single caged and housed for 1 week and treated with vehicle or compounds at various daily doses, given orally in a 1% Carboxymethylcellulose (CMC)+0.25% Tween 80 in PBS, pH 6.8 formulation. At the end of the study, the animals are sacrificed using $CO_2$, followed by blood collection using cardiac puncture. The animals are then subjected to necropsy to collect intact ventral prostate, seminal vesicle and/or testes to measure organ wet weight changes between treatment groups. Significant lowering of ventral prostate weights compared to vehicle control is determined using the Dunnet's test. The plasma derived from these animals are used to measure hormone changes and subsequently compared to vehicle control. The prostate tissue is snap-cooled in RNA later™ solution, and total RNA is obtained using the RNeasy kit (Qiagen Corp.). Specific Taqman primers (see list below) for SGP-2 or clusterin, 18S ribosomal RNA (Applied Biosystems, Foster City, Calif., Catalog #4310893E) and smooth muscle myosin heavy chain (derived from Genebank sequence for rat NM_013607) are used to quantify biomarker changes in these prostate tissues using real time PCR.

```
PCR primers:
                                         (SEQ ID NO: 1)
mouse SGP-2 gi 192149 -61F CGCAGACCGGACTCCAGAT (SEQ ID NO: 2)
mouse SGP-2 gi 192149 -121R CCACGCACAGCAGGAGAAT mouse SGP-2 TaqMan" probe:
                                         (SEQ ID NO: 3)
mouse SGP-2 gi 192149 -81T CCAAGGAGGCCACGCCATGAA
```

While the exemplified compounds of the present invention demonstrate significant lowering of ventral prostate weights compared to vehicle control according to this test, preferred compounds demonstrate a significant lowering in prostate weight at doses of 10 mg/kg/day or less.

Therapeutic Methods of Use and Dosages

The various diseases and conditions described herein are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of Formula I.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of Formula I is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of Formula I can be administered in any form or mode which makes the compound bioavailable in a therapeutically effective amount, including oral, inhalation, and parenteral routes. For example, compounds of Formula I can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

Pharmaceutical compositions of the compounds of Formula I are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations typically contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of Formula I present in such compositions is such that a suitable dosage will be obtained. Preferred compositions and preparations can be determined by one of ordinary skill in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the Formula I or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

We claim:
1. A compound selected from the group consisting of:
   9-(4-Hydroxy-phenyl)-4b,5,6,7,8,8a,9,10-octahydro-phenanthren-3-ol;
   4-(4-Hydroxy-phenyl)-2,3,3a,4,5,9b-hexahydro-1H-cyclopenta[a]naphthalen-8-ol;
   9-(4-Hydroxy-phenyl)-4b,5,6,7,8,8a,9,10-octahydro-phenanthrene-1,3-diol;
   9-(4-Hydroxy-phenyl-1-methoxymethyl-4b,5,6,7,8,8a,9,10-octahydro-phenanthren-3-ol;
   1-Hydroxymethyl-9-(4-hydroxy-phenyl)-4b,5,6,7,8,8a,9,10-octahydro-phenanthren-3-ol;
   [3 -Hydroxy-9-(4-hydroxy-phenyl)-4b,5 ,6,7,8, 8a,9,10-octahydro-phenanthren- 1-yl]-acetonitrile;
   3-Hydroxy-9-(4-hydroxy-phenyl)-4b,5,6,7,8,8a,9,10-octahydro-phenanthren-1-carbonitrile;
   9-(4-Hydroxy-phenyl)-4b,5,6,7,8,8a,9,10-octahydro-phenanthrene-2,3-diol;
   9-(4-Hydroxy-phenyl)-2-methoxy-4b,5,6,7,8,8a,9,10-octahydro-phenanthren-3-ol;
   9-(4-Hydroxy-phenyl)-2-methoxymethyl-4b,5,6,7,8,8a,9,10-octahydro-phenanthren-3-ol;
   [6-Hydroxy-10-(4-hydroxy-phenyl)-1,2,3,4,4a,9,10,10a-octahydro-phenanthrene-9-yl]-acetonitrile;
   or a pharmaceutically acceptable salt thereof.

2. A pharmaceutical composition comprising a therapeutically effective amount of a compound, or a pharmaceutically acceptable salt thereof, of claim 1 together with a pharmaceutically acceptable carrier, diluent or excipient.

* * * * *

UNITED STATES PATENT AND TRADEMARK OFFICE
CERTIFICATE OF CORRECTION

PATENT NO.         : 8,093,302 B2                        Page 1 of 1
APPLICATION NO.    : 11/814806
DATED              : January 10, 2012
INVENTOR(S)        : Elizabeth Marie Thomas et al.

It is certified that error appears in the above-identified patent and that said Letters Patent is hereby corrected as shown below:

At Column 107, Line 27: In Claim 1, delete "phenyl-1" and insert -- phenyl)-1 --, therefor.

Signed and Sealed this
Twentieth Day of March, 2012

David J. Kappos
*Director of the United States Patent and Trademark Office*